US00RE39112E

(19) United States
(12) Reissued Patent
Asano et al.

(10) Patent Number: US RE39,112 E
(45) Date of Reissued Patent: May 30, 2006

(54) PURINE DERIVATIVES AND ADENOSINE A2 RECEPTOR ANTAGONISTS SERVING AS PREVENTIVES/REMEDIES FOR DIABETES

(75) Inventors: Osamu Asano, Ushiku (JP); Hitoshi Harada, Ushiku (JP); Yorihisa Hoshino, Tsukuba (JP); Seiji Yoshikawa, Ibaraki (JP); Takashi Inoue, Tsukuba (JP); Tatsuo Horizoe, Ushiku (JP); Nobuyuki Yasuda, Ushiku (JP); Kaya Ohashi, Tokyo (JP); Junsaku Nagaoka, Tsukuba (JP); Manabu Murakami, Tsukuba (JP); Seiichi Kobayashi, Lexington, MA (US)

(73) Assignee: Eisai Co., Ltd., Tokyo (JP)

(21) Appl. No.: 11/057,854

(22) PCT Filed: Dec. 24, 1998

(86) PCT No.: PCT/JP98/05870

§ 371 (c)(1),
(2), (4) Date: Jul. 5, 2000

(87) PCT Pub. No.: WO99/35147

PCT Pub. Date: Jul. 15, 1999

Related U.S. Patent Documents

Reissue of:
(64) Patent No.: 6,579,868
Issued: Jun. 17, 2003
Appl. No.: 09/582,840
Filed: Jul. 5, 2000

(30) Foreign Application Priority Data

Jan. 5, 1998 (JP) ..... 10-000526

(51) Int. Cl.

| | |
|---|---|
| ***C07D 473/34*** | (2006.01) |
| ***C07D 473/30*** | (2006.01) |
| ***C07D 473/00*** | (2006.01) |
| ***A61K 31/52*** | (2006.01) |
| ***A61K 31/522*** | (2006.01) |

(52) U.S. Cl. ..... 514/211.08; 514/211.15; 514/227.8; 514/234.2; 514/263.2; 514/263.22; 514/263.3; 514/263.4; 540/481; 540/492; 540/524; 544/61; 544/118; 544/264; 544/265; 544/277

(58) Field of Classification Search ..... 540/481, 540/492, 524; 514/263.4, 263.2, 227.8, 234.2, 514/211.08, 211.15, 263.3, 263.22; 544/61, 544/118, 264, 265, 277
See application file for complete search history.

(56) References Cited

U.S. PATENT DOCUMENTS 5,256,398 A * 10/1993 McAfee et al. ..... 424/9.1

(Continued)

FOREIGN PATENT DOCUMENTS

JP 5-222045 * 8/1993

(Continued)

OTHER PUBLICATIONS

Zhange, Metabolism 46, 273 (1997).*

(Continued)

*Primary Examiner*—Mark L. Berch
(74) *Attorney, Agent, or Firm*—Birch, Stewart, Kolasch & Birch, LLP

(57) ABSTRACT

The present invention provides a preventive or therapeutic agent of a new type for diabetes mellitus and diabetic complications on the basis of an adenosine A2 receptor antagonist action.

A purine compound represented by the formula (I), its pharmacologically acceptable salt or hydrates thereof has an adenosine A2 receptor antagonistic action and is useful for prevention or therapy of diabetes mellitus and diabetic complications. In addition, adenosine A2 receptor antagonists having different structures from those of the compounds described above, for example KW6002, are also effective for prevention or therapy of diabetes mellitus and diabetic complications.

(I)

In the formula, W is —$CH_2CH_2$—, or —CH═CH— or —C≡C—; $R^1$ is:

(in the formula, X is hydrogen atom, hydroxyl group, a lower alkyl group, a lower alkoxy group, etc.; and $R^5$ and $R^6$ are the same as or different from each other and each represents hydrogen atom, a lower alkyl group, a cycloalkyl group, etc.) and the like; $R^2$ is an amino group, etc. which maybe substituted with a lower alkyl group, etc.; $R^3$ is a cycloalkyl group, an optionally substituted aryl group, etc.; and $R^4$ is a lower alkyl group etc.

KW6002

22 Claims, No Drawings

U.S. PATENT DOCUMENTS

| | | | | | |
|---|---|---|---|---|---|
| 5,861,396 | A | * | 1/1999 | Niewohner et al. | 514/234.2 |
| 5,861,404 | A | * | 1/1999 | Niewohner et al. | 514/263.24 |
| 6,511,984 | B1 | * | 1/2003 | Elliott | 514/263.2 |

FOREIGN PATENT DOCUMENTS

| | | | |
|---|---|---|---|
| JP | 9-124648 | * | 5/1997 |
| WO | WO 9206976 A1 | * | 4/1992 |
| WO | WO 9701551 A1 | * | 1/1997 |
| WO | WO 9746560 A1 | * | 12/1997 |

OTHER PUBLICATIONS

Sonnenberg, Curr. Opinion Nephrol. Hypertens. 7, 551 (1998).*

Seyama, JACS 110, 2192 (1988).*

Zielenkiewicz et al., Journal of Thermal Analysis, vol. 43, pp. 775–779 □□(1995).*

Tanji et al., Chemical & Pharmaceutical Bulletin, vol. 36, No. 6, pp. 1935–1941.*

Legraverend et a;., Bioorganic & Medicinal Chemistry Letters, vol. 8, pp. 793–798 (1998).*

Camaion et al., Bioorganic & Medicinal Chemistry Letters, vol. 6, pp. 523–533 (1998).*

* cited by examiner

PURINE DERIVATIVES AND ADENOSINE A2 RECEPTOR ANTAGONISTS SERVING AS PREVENTIVES/REMEDIES FOR DIABETES

Matter enclosed in heavy brackets [ ] appears in the original patent but forms no part of this reissue specification; matter printed in italics indicates the additions made by reissue.

This application is the national phase under 35 U.S.C. §371 or PCT International Application No. PCT/JP98/05870 which has an International filing date of Dec. 24, 1998, which is designated the United States of America.

TECHNICAL FIELD TO WHICH THE INVENTION BELONGS

The present invention relates to a novel purine compound having an adenosine receptor antagonism and to a preventive or therapeutic agent for diabetes mellitus and diabetic complication comprising an adenosine receptor antagonist having a hypoglycemic action and a glucose tolerance improving action on the basis of an inhibiting action to [saccharogenesis] *glucose production* and a promoting action to [saccharide] *glucose* utilization at the periphery. More particularly, it relates to a preventive or therapeutic agent for diabetes mellitus and diabetic complications in which an adenosine receptor antagonist is an adenosine A2 receptor antagonist.

PRIOR ART

With regard to therapeutic agents for diabetes mellitus, various biguanide compounds and sulfonylurea compounds have been used. However, the biguanide compounds induce a lactic acidosis and, therefore, their use is limited while the sulfonylurea compounds often result in a severe hypoglycemia due to their strong hypoglycemic action and, therefore, their use is to be careful.

An object of the present invention is to provide a preventive or therapeutic agent for diabetes mellitus and diabetic complications on the basis of a new action mechanism which is different from that of conventional biguanide compounds and sulfonylurea compounds having several limitations in actual use.

DISCLOSURE OF THE INVENTION

The present inventors have carried out various investigations and, as a result, they have found that antagonists to adenosine receptors can be preventive or therapeutic agents of a new type for diabetes mellitus. Thus, hyperglycemia of spontaneous diabetic mice was relieved by an adenosine receptor antagonist. Such an action is presumed to be the results of inhibition of the gluconeogenic action and the glycogenolytic action, promoted by endogenous adenosine, from liver by an antagonist. Based upon such a finding, the present inventors have carried out an investigation for the compounds having excellent hypoglycemic action and glucose tolerance improving action as a preventive or therapeutic agent and have found novel purine compounds represented by the following formula (I). As a result of further investigation of their action mechanism in detail, they have found that, among the adenosine receptor antagonistic action, the adenosine A2 receptor antagonistic action is the real substance for showing the hypoglycemic and glucose tolerance improving action and have accomplished the present invention where adenosine A2 receptor antagonist is a preventive or therapeutic agent of a new type for diabetes and diabetic complications.

The novel purine compound according to the present invention is represented by the following formula (I).

A purine compound represented by the formula (I), its pharmacologically acceptable salt or hydrates thereof.

(I)

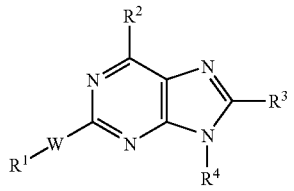

In the formula $R^1$ means:

1) formula:

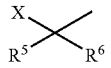

(in the formula, X represents hydrogen atom, hydroxyl group, an optionally substituted lower alkyl group, an optionally substituted lower alkoxy group, an optionally substituted aryl group, an optionally substituted heteoaryl group, an optionally substituted acyl group, an optionally substituted acyloxy group or an optionally substituted amino group; and $R^5$ and $R^6$ are the same as or different from each other and each represents hydrogen atom, an optionally substituted lower alkyl group, an optionally substituted saturated or unsaturated $C_{3-8}$ cycloalkyl group, an optionally substituted $C_{3-8}$cycloalkyl-$C_{2-6}$alkyl group, an optionally substituted aryl group, an optionally substituted heteroaryl group, an optionally protected carboxyl group or an optionally substituted four to six membered ring having at least one hetero atom. Alternatively, $R^5$ and $R^6$ may represent an oxygen atom or a sulfur atom together or may represent a ring being formed together with the carbon atom to which they are bonded which may have a hetero atom. This ring may be substituted.); or 2) a five- or six-membered aromatic ring which may have substituent group and hetero atom.

W represents a formula —$CH_2CH_2$—, —CH═CH— or —C≡C—.

$R^2$ represents hydrogen atom, an optionally substituted lower alkyl group, hydroxyl group or a formula —$NR^7R^8$ (in which $R^7$ and $R^8$ are the same as or different from each other and each represents hydrogen atom, hydroxyl group, an optionally substituted lower alkyl group, an optionally substituted acyl group, an optionally substituted $C_{3-8}$ cycloalkyl group, an optionally substituted aryl group or an optionally substituted heteroaryl group. Alternatively, $R^7$and $R^8$ may be a saturated ring which is formed together with a nitrogen atom to which they are bonded. This ring may further have a hetero atom or a substituent).

$R^3$ represents hydrogen atom, an optionally substituted $C_{3-8}$ cycloalkyl group, an optionally substituted aryl group, an optionally substituted heteroaryl group or an optionally substituted $C_{2-6}$ alkenyl group.

$R^4$ represents hydrogen atom, an optionally substituted lower alkyl group, an optionally substituted $C_{3-8}$ cycloalkyl group, an optionally substituted aryl group, an optionally substituted heteroaryl group, an optionally substituted $C_{2-6}$ alkenyl group, an optionally substituted $C_{2-6}$ alkynyl group or an optionally substituted cyclic ether.

However, the case where (1) W is —$CH_2CH$— and X is hydrogen atom and an alkyl group or where (2) W is —C≡C—, $R^3$ is hydrogen atom and $R^4$ is an optionally substituted cyclic ether is excluded.

There has been no report that an adenosine A2 receptor antagonist is effective for prevention and therapy of diabetes mellitus and diabetic complications.

The present invention provides a preventive or therapeutic agent for diabetes, a preventive or therapeutic agent for diabetic complications, a hypoglycemic agent, an improving agent for impaired glucose tolerance, a potentiating agent for insulin sensitivity obesity which comprises a purine compound of the formula (I), its pharmacologically acceptable salt or hydrates thereof as an active ingredient.

The present invention provides a method or a use by administering a pharmacologically or clinically effective amount of purine compound of the formula (I), its pharmacologically acceptable salt or hydrates thereof to a patient for prevention or therapy of diabetes mellitus, for prevention or therapy of diabetic complications, for prevention or therapy of a disease against which a purine compound of the formula (I), its pharmacologically acceptable salt or hydrates thereof is effective for its prevention or therapy, for hypoglycemia, for improvement of impaired glucose tolerance, for potentiation of insulin sensitivity, of for prevention and therapy of obesity.

The present invention provides a pharmaceutical composition containing a pharmacologically or clinically effective amount of a purine compound of the formula (I), its pharmacologically acceptable salt or hydrates thereof.

Adenosine is a nucleoside widely existing in living body and has a physiological action to a cardiovascular system, a central nervous system, a respiratory system, kidney, an immune system, etc. The action of adenosine is achieved via at least four receptors—A1, A2a, A2b and A3—in which G protein is participated (Fredholm, B. B. et al., Pharmacol. Rev., 46, 143–156, 1994.). In 1979, adenosine receptor was at first classified into A1 and A2 on the basis of their pharmacological action and participation in adenylate cyclase (Van Calker, D. et al., J. Neurochem., 33, 999–1003, 1979.). Then A2 receptor has classified into the subtypes of A2a and A2b on the basis of high and low affinity to adenosine and to adenosine A2 agonists, i.e. NECA and CGS-21680 (Burns, R. F. et al., Mol. Pharmacol., 29, 331–346, 1986.; Wan, W. et al., J. Neurochem., 55, 1763–1771, 1990.). Although gradually, physiological and pathological significance of those receptors has been clarified in a central nervous system, a circulatory system, etc.

With regard to [saccharometabolism,] *glucose metabolism,* the following reports have been available. In an experiment using skeletal muscles, adenosine lowers the insulin sensitivity due to an agonistic action to the A1 receptor suppressing the [incorporation of saccharide] *glucose uptake* while an A1 receptor antagonist increases the insulin sensitivity (Challis, R. A., Biochem. J., 221, 915–917, 1984; Challis, R. A. , Eur. J. Pharmacol. 226, 121–128, 1992.). In fat cells, adenosine enhances the sensitivity of insulin via an A1 receptor, whereby [incorporation of saccharide] *glucose uptake* is promoted (Vannucci, S. J., et al., Biochem. J., 228, 325–330, 1992). Further WO 95/18128 and WO 98/03507 disclose a therapeutic agent for diabetes mellitus comprising an A1 receptor antagonist. This, there have been many reports concerning an A1 receptor. With regard to an adenosine A2 receptor, there is a simple description in WO 97/01551 suggesting a therapeutic agent for diabetes mellitus comprising the A2a receptor antagonist although any group therefor is not mentioned at all. In Collis, M. G. et al., Trends Pharmacol. Sci., 14, 360–366, 1993., participation of the adenosine A2 receptor in the promotion of gluconeogenesis in hepatic cells is suggested but there is no specific description at all. On the contrary, WO 98/01459 describes a therapeutic agent for diabetes mellitus comprising the A2 receptor agonist but thee is no description for the adenosine A2 receptor antagonist at all. As such, the positioning of the adenosine A2 receptor antagonist as a therapeutic agent for diabetes mellitus has been in a chaotic state.

The adenosine A2 receptor antagonist of the present invention as a preventive or therapeutic agent for diabetes mellitus and for diabetic complications is selected, for example, from the following compounds 1) to 4).

1) Formula (I)

(I)

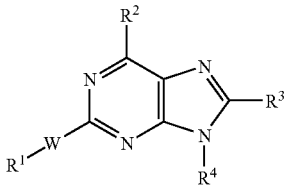

In the formula $R^1$ represents:

(1) formula:

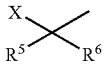

(in the formula X is hydrogen atom, hydroxyl group, an optionally substituted lower alkyl group, an optionally substituted lower alkoxy group, an optionally substituted aryl group, an optionally substituted heteroaryl group, an optionally substituted acyl group, an optionally substituted acyloxy group or an optionally substituted amino group; and $R^5$ and $R^6$ are the same as or different from each other and each represents hydrogen atom, an optionally substituted lower alkyl group, an optionally substituted saturated or unsaturated $C_{3-8}$ cycloalkyl group, an optionally substituted $C_{3-8}$ cycloalkyl-$C_{2-6}$ alkyl group, an optionally substituted aryl group, an optionally substituted heteroaryl group, an optionally protected carboxyl group or an optionally substituted four- to six-membered ring having at least one hetero atom. Alternatively, $R^5$ and $R^6$ represents an oxygen atom or a sulfur atom together or represents a ring which may have hetero atom being formed together with the carbon atom to which they are bonded. This ring may be substituted); or (2) a five- or six-membered aromatic ring which may have substituent group and hetero atom.

W represents formula —$CH_2CH_2$—, —CH═CH—, or —C≡C—.

$R^2$ represents hydrogen atom, an optionally substituted lower alkyl group, hydroxyl group or a formula —$NR^7R^8$ (in which $R^7$ and $R^8$ are the same as or different from each other and each represents hydrogen atom, a hydroxyl group, an optionally substituted lower alkyl group, an optionally substituted acyl group, an optionally substituted $C_{3-8}$ cycloalkyl group, an optionally substituted aryl group or an optionally substituted heteoaryl group. Alternatively, $R^7$ and $R^8$ represents a saturated ring which is formed together with a nitrogen atom to which they are bonded. This ring may further have hetero atom or substituent.)

$R^3$ represents hydrogen atom, an optionally substituted $C_{3-8}$ cycloalkyl group, an optionally substituted aryl group, an optionally substituted heteroaryl group or an optionally substituted $C_{2-6}$ alkenyl group.

$R^4$ represents hydrogen atom, an optionally substituted lower alkyl group, an optionally substituted $C_{3-8}$ cycloalkyl group, an optionally substituted aryl group, an optionally substituted heteroaryl group, an optionally substituted $C_{2-6}$ alkenyl group, an optionally substituted $C_{2-6}$ alkynyl group or an optionally substituted cyclic ether group.

However, the case where (1) W is —$CH_2CH_2$— and X is hydrogen atom and an alkyl group or where (2) W is —C≡C—, $R^3$ is hydrogen atom and $R^4$ is an optionally substituted cyclic ether is excluded.

That is, the present invention is the purine compound of the above formula (I), its pharmacologically acceptable salt or hydrates thereof.

Among these compounds, the preferred examples are those where W is ethylene group or ethylene group and the more preferred example is that where W is ethynylene group.

The purine compound of the present invention includes an ethynylenepurine compound represented by the formula (I'):

(I')

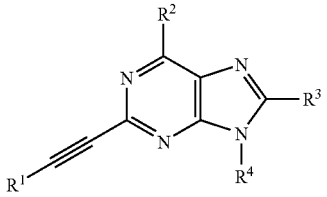

except the case where $R^3$ is hydrogen atom and $R^4$ is an optionally substituted cyclic ether.

2) A compound represented by the formula (VII):

(VII)

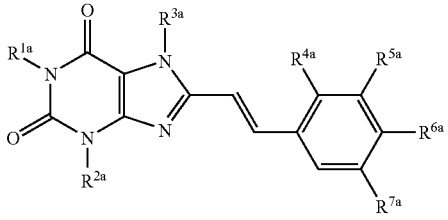

(in the formula, $R^{1\alpha}$ and $R^{2\alpha}$ are the same as or different from each other and each represents a $C_{1-4}$ lower alkyl group or allyl group; $R^{3\alpha}$ represents hydrogen atom or a $C_{1-3}$ lower alkyl group; and $R^{4\alpha}$, $R^{5\alpha}$, $R^{6\alpha}$ and $R^{7\alpha}$ are the same as or different from each other and each represents hydrogen atom, a halogen atom, a $C_{1-3}$ lower alkyl group, a $C_{1-3}$ lower alkoxy group, nitro group, amino group or hydroxyl group) or a pharmaceutically acceptable salt thereof.

Among those compounds, the preferred examples are those where $R^{1\alpha}$, $R^{2\alpha}$ and $R^{3\alpha}$ are the same as or different from each other and each represents a $C_{1-3}$ lower alkyl group and any of $R^{4\alpha}$, $R^{5\alpha}$, $R^{6\alpha}$ and $R^{7\alpha}$ is a $C_{1-3}$ lower alkoxy group, and the more preferred examples are those where $R^{1\alpha}$, $R^{2\alpha}$ and $R^{3\alpha}$ are the same as or different from each other and each represents a $C_{1-3}$ lower alkyl group and $R^{5\alpha}$ and $R^{6\alpha}$ are methoxy groups.

3) A compound represented by the formula (VII):

(VIII)

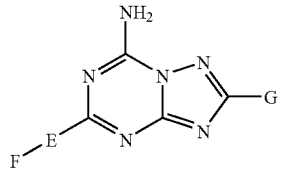

(in the formula, E represents an oxygen atom, a sulfur atom, $SO_2$ or NH; F represents a $C_{5-6}$ cycloalkyl group, a pyridyl group, a thizolyl group, a $C_{1-6}$ alkyl group, an optionally substituted phenyl group, an optionally substituted phenyl-$C_{1-2}$ alkyl group, a morphoinoethyl group, a furylmethyl group or a pyridylmethyl group; and G represents a furyl group, a thienyl group or an isoxazolyl group) or a pharmacologically acceptable salt thereof.

Among those compounds, the preferred examples are those where E is NH, F is 2-(4-hydroxyphenyl)ethyl group or 2-(morpholino)ethyl group and G is a furyl group.

4) A compound represented by the formula (IX):

(IX)

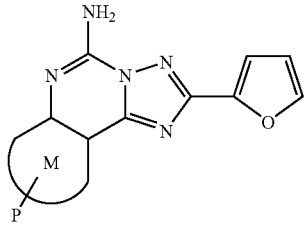

(in the formula, the ring M represents pyrazole or triazole; and P represents a phenyl-($C_{1-3}$)alkyl group optionally substituted with halogen atom, an alkyl group, an alkoxy group or cyano, or a $C_{1-6}$ alkyl group) or a pharmacologically acceptable salt thereof.

Among those compounds, the preferred example is that where the ring M is pyrazole and P is a phenethyl group.

5) A compound represented by the formula (X):

(X)

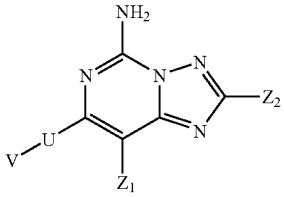

(in the formula, U represents an oxygen atom, a sulfur atom or NH group; V represents an optionally hydroxyl-substituted lower alkyl group, a phenyl or aralkyl group which may be substituted with a lower alkoxy group, a lower alkyl group, a halogen atom, hydroxyl group, etc. or a heteroaryl group; $Z_1$ represents hydrogen atom, a halogen atom or a lower alkyl group; and $Z_2$ represents a heteroaryl group such as a furyl group) or a pharmaceutically acceptable salt thereof.

Among those compounds, the preferred one is that where U is an oxygen atom, V is 2,6-dimethoxyphenyl group, $Z_1$ is hydrogen atom and $Z_2$ is a furyl group.

The present invention provides a preventive or therapeutic agent for diabetes, a preventive or therapeutic agent for diabetic complications, a hypoglycemic agent, an improving agent for impaired glucose tolerance, a potentiating agent for insulin sensitivity or obesity which comprises an adenosine A2 receptor antagonist, its pharmacologically acceptable salt or hydrates thereof as an active ingredient.

It is preferred that the above adenosine A2 receptor antagonist its adenosine A2a and/or A2b receptor antagonist.

Examples of those which are preferred as the adenosine A2a or A2b receptor antagonist of the present invention are those where the Ki value showing an affinity to the A2a receptor by the experimental method which will be mentioned later is not more than 0.5 μM, those where the $IC_{50}$ value showing the suppression of cAMP production stimulated by NECA in the A2b receptor is not more than 0.7 μM or those satisfying both of them. Examples of those which are more preferred are those where the Ki value showing an affinity to the A2a receptor by the experimental method which will be mentioned later is not more than 0.1 μM, those where the $IC_{50}$ value showing the suppression of cAMP production stimulated by NECA in the A2b receptor is not more than 0.5 μM or those satisfying both of them.

The present invention provides a method or a use by administrating a pharmacologically or clinically effective amount of an adenosine A2 receptor antagonist, its pharmacologically acceptable salt or hydrates thereof to a patient for prevention of therapy of diabetes mellitus, for prevention or therapy of diabetic complications, for prevention or therapy of a disease against which an adenosine A2 receptor antagonist, its pharmacologically acceptable salt or hydrates thereof is effective for its prevention or therapy, for hypoglycemia, for improvement of impaired glucose tolerance, for potentiation of insulin sensitivity, or for prevention and therapy of obesity.

The present invention provides a pharmaceutical composition containing a pharmacologically or clinically effective amount of an adenosine A2 receptor antagonist, its pharmacologically acceptable salt or hydrates thereof.

In the formula (I), the term "optionally substituted" used in an optionally substituted lower alkyl group, an optionally substituted lower alkoxy group, an optionally substituted cycloalkyl group, an optionally substituted aryl group, an optionally substituted heteroaryl group, etc. in the definitions for X, $R^2$, $R^3$, $R^4$, $R^5$, $R^6$, $R^7$ and $R^8$ represents that each of the groups may be substituted with a group selected, for example, from a hydroxyl group; a thiol group; a nitro group; a cyano group; a halogen atom such as a fluorine atom, a chlorine atom, a bromine atom and an iodine atom; a lower alkyl group such as methyl, ethyl, n-propyl and isopropyl; a lower alkoxy group such as methoxy, ethoxy, n-propoxy, isopropoxy and butoxy groups; a halogenated alkyl group such as a fluoromethyl group, a difluoromethyl group, a trifluoromethyl group and a 2,2,2-trifluoroethyl group; an alkylthio group such as methylthio group, an ethylthio group and an isopropylthio group; an acyl group such as an acetyl group, a propionyl group and a benzoyl group; a hydroxyalkyl group such as a hydroxymethyl group, a hydroxyethyl group and a hydroxypropyl group; an amino group; a monoalkylamino group such as a methylamino group, an ethylamino group and an isopropylamino group; a dialkylamino group such as a dimethylamino group and a diethylamino group; a cyclic amino group such as an aziridinyl group, an azetidinyl group, a pyrrolidinyl group, a piperidinyl group, a perhydroazepinyl group and a piperazinyl group; a carboxyl group; an alkoxycarbonyl group such as a methoxycarbonyl group, an ethoxycarbonyl group and a propylcarbonyl group; a carbamoyl group; an alkylcarbamoyl group such as a methylcarbamoyl group and a dimethylcarbamoyl group; an acylamino group such as an acetylamino group and a benzoylamino group; an unsubstituted or $C_{1-4}$ alkyl-substituted sulfamoyl group or an alkylsulfonyl group such as a methylsulfonyl group and an ethylsulfonyl group; an unsubstituted or substituted arylsulfonyl group such as a benzenesulfonyl group and a p-toluenesulfonyl group; an unsubstituted or substituted aryl group such as a phenyl group, a tolyl group and an anisolyl group, as unsubstituted or substituted heteroaryl group such as a pyrrole group, a pyrazolyl group, an imidazolyl group, a triazolyl group, a tetrazolyl group, a thiazolyl group, a pyridyl group, a pyrimidyl group and a pyrazinyl group; a carboxyalkyl group; an alkyloxycarbonylalkyl group such as a methoxycarbonylmethyl group, an ethoxycarbonylmethyl group and a methoxycarbonylethyl group; a carboxyalkoxy group such as a carboxymethoxy group; an arylalkyl group such as a benzyl group and a 4-chlorobenzyl group; a heteroarylalkyl group such as a pyridylmethyl group and a pyridylethyl group; an alkylenedioxy group such as a methylenedioxy group and an ethylenedioxy group; etc.

The halogen atom in the definitions for A and B is fluorine, chlorine, bromine or iodine.

The lower alkyl group in the definitions for X, $R^2$, $R^4$, $R^5$, $R^6$, $R^7$ and $R^8$ means a linear or branched alkyl group having 1–6 carbon atoms. Its examples are methyl group, ethyl group, n-propyl group, isopropyl group, n-butyl group, isobutyl group, sec-butyl group, tert-butyl group, n-pentyl group, 1,2-dimethylpropyl group, 1,1-dimethylpropyl group, 2,2-dimethylpropyl group, 2-ethylpropyl group, n-hexyl group, 1,2-dimethylbutyl group, 2,3-dimethylbutyl group, 1,3-dimethylbutyl group, 1-ethyl-2-methylpropyl group and 1-methyl-2-ethylpropyl group.

The lower alkoxy group in the definitions for X means a linear or branched alkoxy group having 1–6 carbon atoms. Its examples are methoxy group, ethoxy group, n-propoxy group, isopropoxy group, a n-butoxy group, sec-butoxy group, tert-butoxy group, n-pentyloxy group, 1,2-dimethylpropyloxy group, 1,1-dimethylpropyloxy group, 2,2-dimethylpropyloxy group, 2-ethylpropyloxy group, n-hexyloxy group, 1,2-dimethylbutyloxy group, 2,3-dimethylbutyloxy group, 1,3-dimethylbutyloxy group, 1-ethyl-2-methylpropyloxy group and 1-methyl-2-ethylpropyloxy group.

The cycloalkyl group in the definitions for X, $R^3$, $R^4$, $R^5$, $R^6$, $R^7$ and $R^8$ means a cycloalkyl group having 3–8carbons such as cyclopropyl group, cyclobutyl group, cyclopentyl group, cyclohexyl group, cycloheptyl group or cyclooctyl group.

The cycloalkylalkyl group in the definitions for X, $R^3$, $R^4$, $R^5$, $R^6$, $R^7$ and $R^8$ means a group where the above cycloalkyl group is bonded to any of the carbon atoms in the above lower alkyl group.

The lower alkenyl group in the definitions for $R^3$ and $R^4$ means a linear or branched alkenyl group having 2–6 carbon atoms such as vinyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group and 3-butenyl group.

The lower alkynyl group in the definition for $R^4$ represents a linear or branched alkynyl group having 2–6 carbon atoms such as ethynyl group, 1-propynyl group, 2-propynyl group, 1-butynyl group, 2-butynyl group, 3-butynyl group, 3-methyl-1-propynyl group and 2-methyl-3-propynyl group.

The acyl group in the definitions for X and $R^2$ represents is group defined from an aliphatic saturated monocarboxylic acid such as acetyl group, propionyl group, butyryl group, valeryl group, isovaleryl group and pivaloyl group; a group derived from an aliphatic unsaturated carboxylic acid such as acryloyl group, propioloyl group, methacrylolyl group, crotonoyl group and isocrotonoyl group; a group derived from a carbocyclic carboxylic acid such as benzoyl group, naphthoyl group, toluoyl group, hydroatropoyl group, atropoyl group and cinnamoyl group; a group derived from a heterocyclic carboxylic acid such as furoyl group, thenoyl group, nicotinoyl group and isonicotinoyl group; a group derived from a hydroxycarboxylic acid or an alkoxycarboxylic acid such as glycoloyl group, lactoyl group, glyceroyl group, tropoyl group, benzyloyl group, salicyloyl group, anisoyl group, vanilloyl group, piperoniloyl group and galloyl group; a group derived from various kinds of amino acids; etc.

The aryl group in the optionally substituted aryl group in the definitions for X, $R^3$, $R^4$, $R^5$, $R^6$, $R^7$ and $R^8$ represents phenyl group, 1-naphthyl group, 2-naphthyl group, anthracenyl group, etc.

The optionally substituted heteroaryl group in the definitions for X, $R^3$, $R^4$, $R^5$, $R^6$, $R^7$and $R^8$ represents a group derived from a monocyte or a condensed ring containing 1–4 of at least one selected from the group consisting of sulfur atom, oxygen atom and nitrogen atom. Its examples are pyrrolyl group, thienyl group, furyl group, thiazolyl group, oxazolyl group, isothiazolyl group, isoxazolyl group, imidazolyl group, pyrazolyl group, thiadiazolyl group, oxadiazolyl group, triazolyl group, tetrazolyl group, pyridyl group, pridazinyl group, pyrimidinyl group, pyrazinyl group, indolyl group, isoindolyl group, benzothienyl group, benzofuranyl group, isobenzofuranyl group, benzimidazolyl group, indazolyl group, benzotriazolyl group, benzothiazolyl group, benzoxazolyl group, quinolyl group, isoquinolyl group, cinnolinyl group, phthalazyl group, quinolxalyl group, naphthyrindinyl group, quinazolinyl group and imidazopyridinyl group.

The protective group in the optionally protected carboxyl group in the definitions for $R^5$ and $R^6$ is, for example, a lower alkyl group such as methyl group, ethyl group and tert-butyl group; a lower alkyl group substituted with an optionally substituted phenyl group such as p-methoxybenzyl, p-nitrobenzyl, 3,4-dimethoxybenzyl, diphenylmethyl, trityl and phenethyl groups; a halogenated lower alkyl group such as 2,2,2-trichloroethyl and 2-iodoethyl; a lower alkanoyloxy lower alkyl group such as pivaloyloxymethyl, acetoxymethyl, propionyloxymethyl, butyryloxymethyl, valeryloxymethyl, 1-acetoxyethyl, 2-acetoxyethyl, 1-pivaloyloxyethyl and 2-pivaloyloxyethyl; a higher alkanoyloxy lower alkyl group such as palmitoyloxyethyl, heptadecanoyloxymethyl and 1-palmitoyloxyethyl; a lower alkoxycarbonyloxy lower alkyl group such as methoxycarbonyloxymethyl, 1-butoxycarbonyloxyethyl and 1-(isopropoxycarbonyloxy) ethyl; a carboxy lower alkyl group such as carboxymethyl and 2-carboxyethyl; a heteroaryl group such as 3-phthalidyl; an optionally substituted benzoyloxy lower alkyl group such as 4-glycyloxybenzoyloxymethyl; a (substituted dioxolene) lower alkyl group such as (5-methyl-2-oxo-1,3-dioxolen-4-yl)methyl; a cycloalkyl-substituted lower alkanoyloxy lower alkyl group such as 1-cyclohexylacetyloxyethyl; a cycloalkyloxycarbonyloxy lower alkyl group such as 1-cyclohexyloxycarbonyloxyethyl; etc. That may be also in various acid amides. In short, any group may be a protective group for the carboxyl group so far as it is decomposed in vivo by certain means to give a carboxylic acid.

The term "a ring which is formed together with the nitrogen amino to which they are bonded" in the definitions for $R^7$, $R^8$, $R^{21}$ and $R^{22}$ represents aziridine, azetidine, pyrrolidine, piperdine, perhydroazepine, perhydroazocine, piperazine, homopiperazine, morpholine, thiomorpholine, etc. Such a ring may be substituted with a lower alkyl group, a halogen atom or acyl group, etc.

It goes without saying that, in the case of a compound having an asymmetric atom in the present invention, an optically active substance thereof is also covered by the present invention. The present invention further covers a hydrate.

Examples of a pharmacologically acceptable salt in the present invention are an inorganic salt such as hydrochloride, hydrobromide, sulfate and phosphate; an organic acid salt such as acetate, maleate, tartrate, methanesulfonate, benzenesulfonate and toluenesulfonate; and a salt with amino acid such as aspartic acid and glutamic acid.

A group of the compounds of the present invention is useful also from the viewpoint of low toxicity and high safety.

When the compound of the present invention is used for the above-mentioned diseases, it may be administered either orally or parenterally. It may be administered in a form of a pharmaceutical preparation such as tablets, powder, granules, capsules, syrup, troche, inhalant, suppository, injection, ointment, ophthalmic ointment, eye drops, nose drops, ear drops, poultice and lotion.

The dose significantly varies depending upon type of the disease, degree of the symptom, age, sex and sensitivity of the patient, etc. but, usually, administration is carried out in a dose of about 0.03–1000 mg, preferably 0.1–500 mg, and more preferably 0.1–100 mg per day to an adult either once daily or dividing into several times a day. In the case of an injection preparation, the dose is usually about 1 μg/kg to 3000 μg/kg, preferably about 3 μg/kg to 1000 μg/kg.

In the manufacture of a pharmaceutical preparation of the compound of the present invention, that is carried out by a conventional means using a common pharmaceutical carrier.

Thus, in the manufacture of a solid presentation for oral use, after addition of filler, binder, disintegrating agent, lubricant, coloring agent, corrective agents for taste and smell, antioxidant, etc. to the main ingredient, then the mixture is made into tablets, coated tablets, granules, powder, capsules, etc. by a conventional manners.

With regard to the above filler, its examples which may be used are lactose, corn starch, sucrose, glucose, sorbitol, crystalline cellulose, silicon dioxide, etc.

With regard to the binder, polyvinyl alcohol, polyvinyl ether, ethyl cellulose, methyl cellulose, gum arabic, tragacanth, gelatin, shellac, hydroxypropyl cellulose, hydroxypropylmethyl cellulose, calcium citrate, dextrin, pectin, etc. may be used for example while, with regard to the lubricant, magnesium stearate, talc, polyethylene glycol, silica, hydrogenated vegetable oil, etc. may be used for example.

With regard to the coloring agent, anything may be used so far as it is permitted to add to pharmaceuticals. With regard to the corrective agents for taste and smell, cocoa powder, menthol, aromatic acid, peppermint oil, borneol, cinnamon powder, etc. may be used. With regard to the antioxidant, anything may be used so far as it is permitted to add to pharmaceuticals such as ascorbic acid and $^{\alpha}$-tocopherol. It is of course possible that tables and granules are appropriately coated with sugar, gelatin and others as required.

On the other hand, in the manufacture of injection, eye drops, etc., it is possible to manufacture by a conventional means by adding, if necessary, pH adjusting agent, buffer, suspending agent, auxiliary solubilizer, stabilizer, isotonizating agent, antioxidant, preservative, etc. to the main ingredient. In that case, it is also possible to prepare a freeze-dried preparation, if necessary. The injection may be administered intravenously, subcutaneously or intramuscularly.

Examples of the above-mentioned suspending agent are methyl cellulose, polysorbate 80, hydroxyethyl cellulose, gum arabic, tragacanth, carboxymethyl cellulose sodium and polyoxyethylene sorbitan monolaurate.

Examples of the auxiliary solubilizer are polyoxyethylene hydrogenated castor oil, polysorbate 80, nicotinamide and polyoxyethylene sorbitan monolaurate.

With regard to the stabilizer, sodium sulfite, sodium metasulfite, ether, etc. may be used for example while, with regard to the preservative, methyl p-hydroxybenzoate, ethyl p-hydroxybenzoate, sorbic acid, phenol, cresol, chlorocresol, etc. may be used for example.

In the manufacture of the ointment, it can be manufactured by a conventional means by addition of stabilizer, antioxidant, preservative, etc. if necessary.

The novel purine compound of the present invention may be manufactured by combining the commonly known methods. As hereunder, main common manufacturing methods for a group of the compounds of the present invention will be given.

Manufacturing Method A

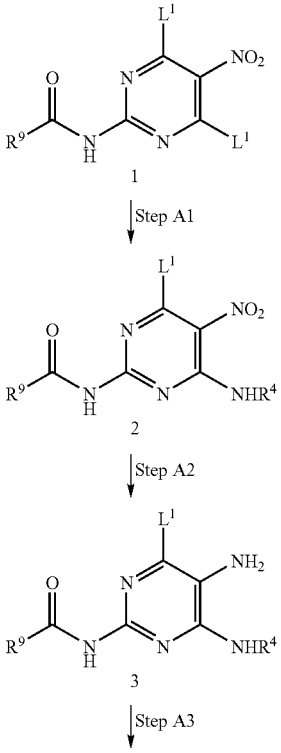

-continued

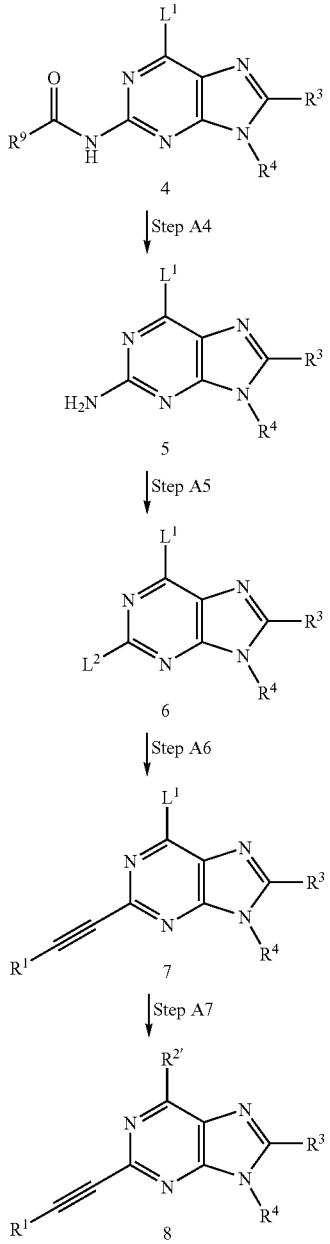

In the above formulae, $L^1$ and $L^2$ represent halogen atom; $R^{2'}$ represents —$NR^7R^8$ (wherein —$NR^7R^8$ has the meaning as defined above); $R^9$ represents a lower alkyl group; and $R^1$, $R^3$ and $R^4$ have the meaning as defined above.

Step A1

This is a step where 4,6-dihalo-5-nitro-2-pyrimidinylacetamide 1 which is a compound synthesized according to a known method is reacted with an amine compound in a solvent whereupon only one halogen is substituted with an amine compound to manufacture 4-aminopyrimidine compound 2.

There is no particular limitation for the solvent used therefor so far as it does not disturb the reaction and is able to dissolve the starting substance to some extent and its preferred examples are ether such as tetrahydrofuran, dioxane, dimethoxyethane and diethylene glycol dimethyl ether; and a halogenated hydrocarbon such as methylene chloride, chloroform and dichloroehtane. The reaction temperature varies depending upon the reactivity of the amine compound used and is preferably −20° C. to 50° C., and more preferably, about 0° C.

In this step, it is preferred to add an equimolar amount of acetic acid to suppress the production of a di-substituted substance.

Step A2

This is a step where a nitor group of the nitropyrimidine compound 2 is reduced by means of a catalytic reduction, a reduction with metal and metal salt, or a metal hydride to manufacture a pyrimidinylamine compound 3.

The catalytic reduction is carried out in a hydrogen atmosphere in the presence of a catalyst such as Raney Ni, Pd—C or $PrO_2$ under ordinary pressure or high pressure at room temperature or with warming. There is no particular limitation for the solvent used so far as it does not act as a catalyst poison and is able to dissolve the starting material to some extent and its suitable examples are methanol, ethanol, tetrahydrofuran, dioxane, acetic acid, dimethylformamide and a mixture thereof. Reduction with metal and metal salt is carried out using zinc dust-hydrochloric acid, stannous chloride-hydrochloride acid, iron-hydrochloric acid, etc. in a solvent of an alcohol such as anhydrous methanol or ethanol or dioxane and tetrahydrofuan. Reduction using a metal hydride is carried out in a solvent of methanol, ethanol or tetrahydrofuran using Pd-sodium borohydride, $NiCl_2(PPh_3)_2$— sodium borohydride, stannous chloride-sodium borohydride, etc.

Step A3

This is a step where an amino group and an aldehyde which are adjacent on a pyrimidine ring is condensed with an imidazole ring to manufacture a purine compound 4.

The reaction is carried out in such a manner that an amino group is condensed with an aldehyde compound to give Schiff base, and then it is treated with ferric chloride, etc. to result in a ring closure.

There is no particular limitation for the solvent used so far as it does not disturb the reaction and is able to dissolve the starting material to some extent and its preferred examples are alcohol such as methanol and ethanol; ether such as tetrahydrofuran, dioxane, dimethoxyethane and diethylene glycol dimethyl ether; and dimethylformamide. The reaction is carried out at 0 to 100° C., and preferably, at room temperature. It is preferred to add acetic acid during the manufacture to Schiff base.

Step A4

This is a step where an acyl group which is a protecting group of the amino group at position 2 of the above purine compound A is eliminated to manufacture a 2-aminopurine compound 5.

The reaction is carried out by means of a treatment with a mineral acid or an alkaline aqueous solution in a solvent such as methanol, ethanol, dioxane and tetrahydrofuran. Although the reaction proceeds even at room temperature, it is preferred to carry it out with heating.

This step may be completed in the above step A3 depending upon the reducing condition, and in that case, this step is omitted.

Step A5

This is a step where an amino group of the 2-aminopurine compound 5 is subjected to a Sandmeyer reaction to convert into a halogen atom to manufacture a 2,6-dihalopurine compound 6.

The reaction is carried out in such a manner that the amino group is diazotized with sodium nitrile or ester nitrous such as amyl nitrite and isoamyl nitrite to give a diazonium group and then the diazonium group is converted to a halogen atom using cuprous halide. When a nitride such as isoamyl nitrite is used in the diazotization, an acid is not particularly necessary but the amino group can be converted to a halogen atom by addition of cuprous halide and methylene halide in a solvent such as dioxane or tetrahydrofuran followed by heating. In the present invention, it is most preferred that cuprous iodide is used as a cuprous halide and diiodemethane is used as a methylene halide to convert into a 2-iodopurine compound.

Step A6

This is a step where a halogen atom at position 2 of the 2,6-dihalopurine compound f is selectively subjected to a coupling reaction with an ethynyl side chain to manufacture a 2-ethynylene-6-halopurine compound 7.

The reaction is carried out at room temperature or with heating in the presence of catalytic amounts of dichlorobistriphenylphosphine palladium (II) and cuprous iodide and a tertiary amine. Examples of the solvent used are ether such as tetrahydrofuran, dioxane, dimethoxyethane and diethylene glycol dimethyl ether; dimethylformamide; and 1-methylpyrrolidinone. Examples of the tertiary amine used are triethylamine, diisopropylethylamine, DBU and dimethylaniline. The reaction temperature is preferably 0 to 100° C., and more preferably, room temperature.

Step A7

This is a step where a halogen atom of the 2-ethynylene-6-halopurine compound 7 is reacted with an amine compound to manufacture a 6-amino-2-ethynylenepurine compound 8.

When the amine compound is gaseous or has a low boiling point, it is preferred that the reaction is carried out in a sealed tube or in an autoclave.

There is no particular limitation for the solvent used so far as it does not disturb the reaction and is able to dissolve the starting material to some extent and its preferred examples are alcohol such as methanol and ethanol; ether such as tetrahydrofuran, dioxane, dimethoxyethane and diethylene glycol dimethyl ether; halogenated hydrocarbon such as methylene chloride, chloroform and dichloroethane; dimethylformamide; and 1-methylpyrrolidinone.

The reaction temperature is preferably 0 to 150° C., and more preferably, 50 to 100° C.

Manufacturing Method B

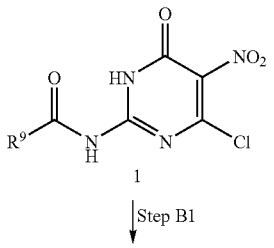

-continued

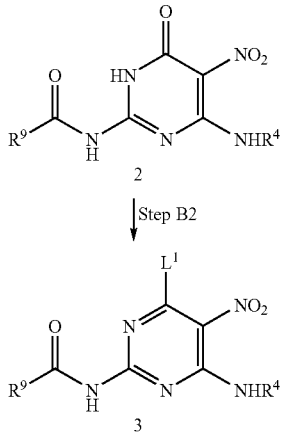

In the above formula, $L^1$, $R^1$, $R^{2'}$, $R^4$ and $R^9$ have the meanings as defined above.

This manufacturing method B is another method for the manufacture of the b 2-acylamino-6-halo-5-nitro-4-pyrimidinylamine compound 3 in the manufacturing method A.

Step B1

This is a step where 2-acylamino-4-chloro-5-nitro-6-pyrimidine compound 1 manufactured by a known method is reacted with an amine compound to manufacture 2-acylamino-4-(substituted amino)-5-nitro-6-pyrimidone compound 2.

There is no particular limitation for a solvent used so far as it does not disturb the reaction and is able to dissolve the starting material to some extent and its preferred examples are ether such as tetrahydrofuan, dioxane, dimethoxyethane and diethylene glycol dimethyl ether; and halogenated hydrocarbon such as methylene chloride, chloroform and dichloromethane. The reaction temperature varies depending upon the reactivity of the amine compound used and it is preferably −20° C. to 50° C., and more preferably, about 0° C.

Step B2

This is a step where an oxo group of the pyrimidone compound is converted into a halogen atom to manufacture 2-acylamino-6-halo-5-nitro-4-pyrimidinylamine compound 3.

The reaction is carried out in the absence of solvent or by suspending in a solvent such as acetonitrile, dioxane or tetrahydrofuran and by treating with a halogenating agent such as phosphorus oxychloride or phosphorus oxybromide with heating under reflux. The reaction is accelerated when tetraethylammonium chloride or dimethylformamide is added to the reaction system.

Manufacturing Method C

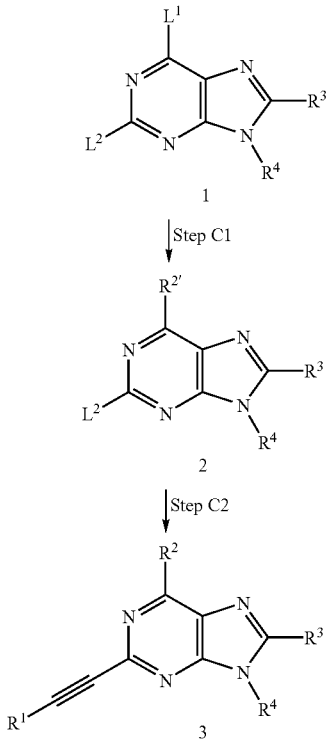

In the above formulae, $L^1$, $L^2$, $R^1$, $R^{2'}$, $R^3$ and $R^4$ have the meanings as defined above.

This manufacturing method C is that where $L^1$ at position 6 on a purine ring of the 2,6-dihalopurine compound 6 in the manufacturing method A is firstly aminated and then $L^2$ at position 2 is converted to an ethynylene group to manufacture the aimed compound.

Step C1

This is a step where a halogen atom at position 6 of the 2,6-dihalopurine compound 1 is reacted with an amine compound to manufacture a 6-amino-2-halopurine compound 2.

When the amine compound is gaseous or has a low boiling point, it is referred that the reaction is carried out in an autoclave.

There is no particular limitation for the solvent used so far as it does not disturb the reaction and is able to dissolve the starting material to some extent and its preferred examples are alcohol such as methanol and ethanol; ether such as tetrahydrofuran, dioxane, dimethoxyethane and diethylene glycol dimethyl ether; halogenated hydrocarbon such as methylene chloride, chloroform and dichloroethane, dimethylformamide; and 1-methylpyrrolidinone.

The reaction temperature is preferably 0 to 150° C., and more preferably, 50 to 100° C.

Step C2

This is a step where the aimed compound is prepared by the same operation as in the above-mentioned step A6.

The reaction is carried out at room temperature or with heating in the presence of catalytic amounts of dichlorobistriphenylphosphine palladium (II) and cuprous iodide and a tertiary amide. Examples of the solvent used are ether such as tetrahydrofuran, dioane, dimethoxyethane and diethylene glycol dimethyl ether; dimethylformamide; and 1-methylpyrrolidinone. Examples of the tertiary amine used are triethylamine, diisopropylethylamine, DBU and dimethylaniline. The reaction temperature is preferably 0 to 100° C. and, more preferably, room temperature.

Manufacturing Method D

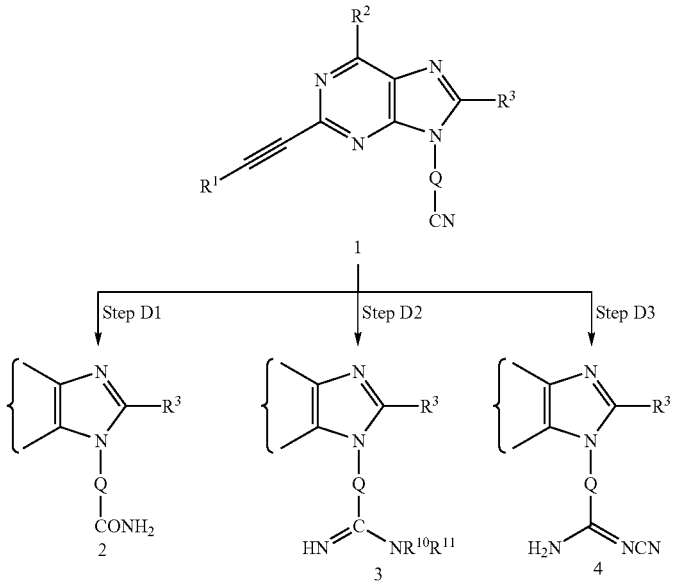

In the above formulae, Q is an alkylene group, an optionally substituted arylene group; an optionally substituted heteroarylene group; an optionally substituted alkylenearylene group; an optionally substituted alkyleneheteroarylene group; an optionally substituted arylenealkylene group; or an optionally substituted heteroarylenealkylene group and $R^1$, $R^2$ and $R^3$ having the meanings as defined above.

This manufacturing method D is a method where, in the case the compound 1 manufactured by the manufacturing method A or C has a cyano group, the cyano group is converted whereupon an amide compound, an amidine compound or an N-cyanoamidine compound is manufactured. Accordingly, when a cyano group is present on the substituents of $R^2$ and $R^3$, the above compounds can be manufactured in a similar manner.

Step D1

This is a step where an amide compound is manufactured from the cyano compound 1 manufactured by the manufacturing method A or C.

The reaction is carried out by treating with an aqueous solution of sodium hydroxide or potassium hydroxide in the presence of a peracid in a water-miscible solvent such as acetone, dioxane, tetrahydrofuran, methanol and ethanol. The reaction temperature is preferably from 0° C. to a refluxing temperature and, more preferably, room temperature.

Step D2

This is a step where an amidine compound is manufactured from the cyano compound 1 manufactured by the manufacturing method A or C.

It is possible to manufacture by various methods. For example, a mono-substituted substance may be manufactured by a method where a cyano compound 1 is heated to 200° C. or higher with an equimolar aromatic amine benezenesulfonate or p-toluenesulfonate; an N,N-disubstituted substance may be manufactured by a method where an amine compound is heated with a cyano compound 1 in the presence of a Lewis acid such as aluminum chloride; and an unsubstituted substance may be manufactured by a method where a cyano compound 1 is treated with an aluminum amide reagent ($MeAlClNH_2$) or by a method where it is converted into an imidate hydrochloride with hydrogen chloride-ethanol followed by treating with ammonia. Alternatively, the mono- or di-substituted substance may be manufactured by treating the imidate hydrochloride with a primary or secondary amine.

Step D3

This is a step where an $N^2$-cyanoamidine compound is manufactured from the cyano compound 1 manufactured by the manufacturing method A or C.

A cyano compound 1 is dissolved in dioxane or tetrahydrofuran, hydrogen sulfide is passed thereinto to saturate, the mixture is allowed to stand at room temperature to convert into thioamide, and then the thioamide is treated with iodomethane to give thiomidate. The thioimidate is treated with cyamide whereupon an N-cyanoamidine compound 4 is manufactured. When this operation is applied to a 2-iodo-6-purinylamine compound manufactured in the step C1 of the manufacturing method C and the firstly prepared 2-iodo-N-cyanoamidine compound is coupled with an alkyne reagent, a cyano compound 1 is manufactured in a similar manner.

Manufacturing Method E

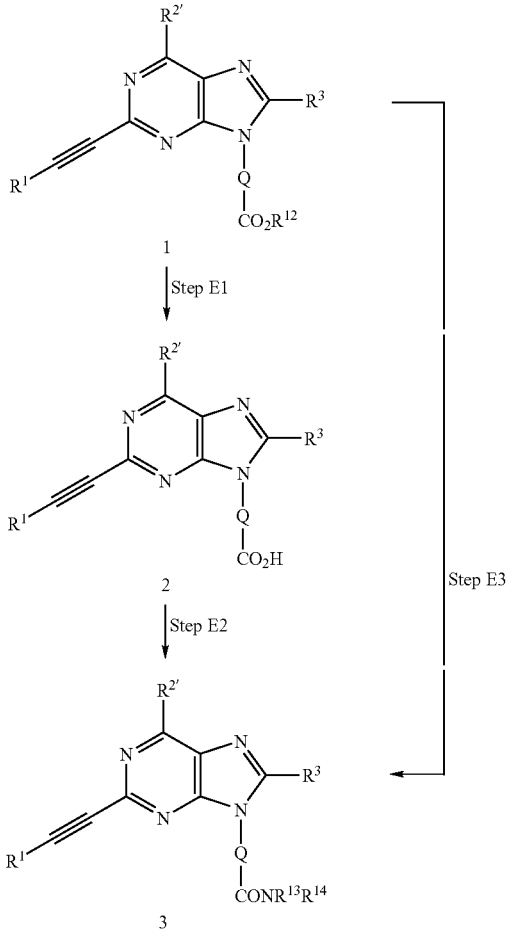

(in the formula, $R^{12}$ represents a protective group for a carboxyl group; $R^{13}$ and $R^{14}$ are the same as or different from each other and each represents hydrogen atom, an optionally substituted lower alkyl group, an optionally substituted aryl group or an optionally substituted heteroaryl group; and $R^1$, $R^{2'}$ and $R^3$ have the meanings as defined above.)

Step E1

This is a step where the protective group is eliminated by an acid or an alkali or by means of heating to manufacture a carboxylic acid compound 2.

Examples of the acid used are an aqueous solution of mineral acid such as hydrochloric acid and sulfuric acid while examples of an alkali are an aqueous solution of sodium hydroxide, potassium hydroxide and lithium hydroxide. With regard to a solvent, any solvent may be used so far as it does not participate in the reaction and that which is miscible with water such as methanol, ethanol, tetrahydrofuran and dioxane is preferred. Preferred reaction temperature is from room temperature to refluxing temperature.

When the protective group is tetrahydropyranyl group, it can be eliminated by heating at from 70 to 150° C.

Step E2

This is a step where the carboxylic acid compound 2 previously prepared is converted into a reactive derivative of the acid and made to react with a primary or secondary amine to manufacture an acid amide compound 3.

Examples of the reactive derivative of the acid are an acid halide such as acid chloride, a mixed acid anhydride such as ethoxycarbonyl chloride obtained by the reaction with chloroformate; and an activated ester such as p-nitrophenyl ester. Examples of the solvent are tetrahydrofuran, dioxane, dichloromethane, chloroform and dichloroethane. The reaction temperature is preferably from −10 to 50° C., and more preferably, from 0° C. to room temperature.

Step E3

This is a step where the ester compound 1 is reacted with an amine compound to directly manufacture an acid amide compound 3 without by way of a carboxylic acid compound 2.

With regard to a protective group $R^{12}$, a lower alkyl group such as a methyl group or an ethyl group is preferred. The reaction is carried out by heating in a sealed tube or in an autoclave. The reaction temperature is preferably from 50 to 100° C.

The above eliminating reaction and amidation reaction can be used for the case where $R^1$ or $R^3$ has a protected carboxyl group as well to manufacture a product.

Manufacturing Method F

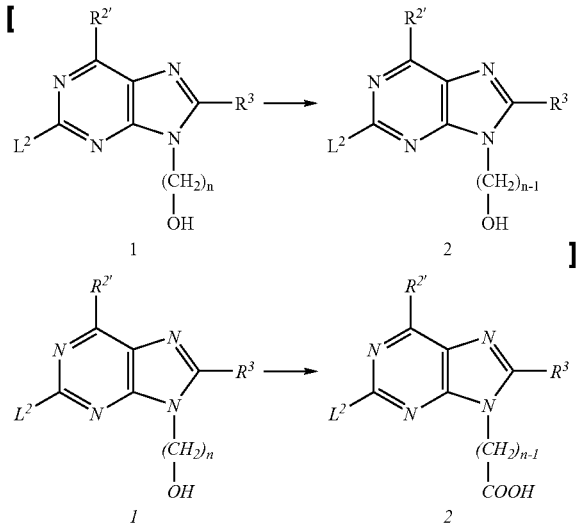

(in the formulae, n represents an integer of from 2 to 6 and $R^{2'}$, $R^3$, $R^{12}$, $R^{13}$ and $R^{14}$ have the meanings as defined above.)

Step F1

This is a step where a purine compound 1 having a hydroxyl-substituted alkyl group is oxidized to manufacture a carboxylic acid compound 2.

With regard to an oxidizing agent, ruthenium tetraoxide, permanganic acid, chromic acid, etc. may be used. With regard to a solvent, carbon tetrachloride, chloroform, methylene chloride, acetonitrile, pyridine, water or a mixed solvent thereof may be used. The reaction is carried out preferably at 0 to 50° C., and more preferably, at room temperature.

A carboxylic group of the carboxylic acid compound 2 manufactured as such is then protected and, after that, conversion into a 2-ethynylenepurine compound is carried out by the same operation as in the step A6 of the manufacturing method A.

When there is a hydroxyl-substituted alkyl group is present in $R^3$, the same method is applied whereupon a 2-ethynylenepurine compound having a carboxylic group in $R^3$ is manufactured by the same method.

Manufacturing Method G

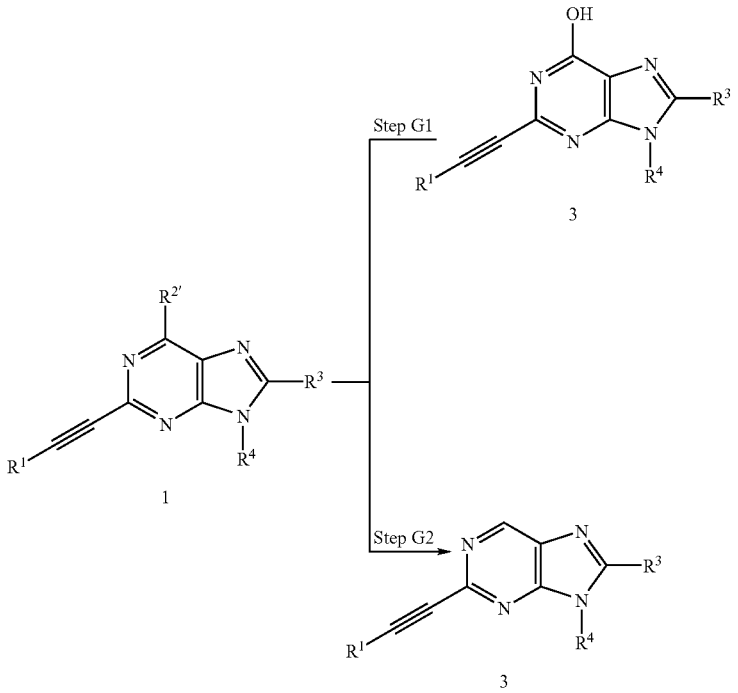

(in the formulae, $R^{2'}$ is an amino group or a halogen atom; and R1, $R^3$ and $R^4$ have the meaning as defined above.)

Step G1

This is a step where the amino group or the halogen atom at position 6 of the purine skeleton is hydrolyzed to manufacture a 6-hydroxypurine compound 2.

The hydrolysis is carried out in the presence of an acid or an alkali and it is preferred to carry out in the presence of an alkali. Examples of the alkali used are sodium hydroxide, potassium hydroxide, etc. The reaction is carried out at from 0 to 100° C.

Step G2

This is a step where the amino group at position 6 is diazotized and heated to eliminate the nitrogen whereupon a 6-unsubstituted purine compound is manufactured.

The reaction is carried out in such a manner that the amino group is diazotized with sodium nitrite or nitrous ester such as amyl nitrite, isoamyl nitrite, etc. in dioxane, tetrahydrofuran or an aqueous solvent thereof and then the diazonium group is eliminated by heating under refluxing.

Incidentally, a method for the manufacture of the compound represented by the formula (VII) is described in JP-A 6-16559 and JP-A-211856, J. Med. Chem., 36, 1333–1342, 1993, etc.; a method for the manufacture of the compound represented by the formula (VIII) is described in JP-A 5-97855 and WO 94/14812; a method for the manufacture of the compound represented by the formula (IX) is described in WO 95/01356 and Eur. J. Med. Chem., 28, 569–576, 1993.; and a method for the manufacture of the compound represented by the formula (X) is described in WO 98/42711.

Now, in order to explain the excellent effect of the purine compounds of the present invention, pharmacological experiments will be shown as hereunder.

Effects of Novel Purine Compounds

1) Suppressing Action to NECA-Stimulated [Saccharogenesis] *Glucose Production* in Hepatic Cells of Primary Culture of Rats Hepatic cells were separated by a collagenase perfusion method from liver of male rats of Wistar strain and subjected to a primary culture in a William's Medium E containing 5% of calf serum, $10^{-6}$ M of dexamethasone and 30 ng/ml of [pertussal] *pertussis* toxin. After one day, the hepatic cells were washed with a Krebs-Ringer Bicarbonate buffer (pH 7.4 (KRB)) containing 10 mM of HEPES and 0.1% of bovine serum albumin and incubated with KRB at 37° C. After 30 minutes, 0.1 μM of NECA (N-ethylcarboxamide adenosine) and a test compound were added thereto at the same time, the mixture was incubated for additional one hour and the amount of glucose released into an incubation medium was measured.

The result is shown in Table 1.

TABLE 1

Suppressing Action to NECA-Stimulated [Saccharogenesis] *Glucose Production* in Hepatic Cells of Primary Culture of Rats

| | |
|---|---|
| Example 8 (sulfate) | 0.49 |
| Example 19 | 0.47 |
| Example 31 | 0.13 |
| Example 64 (sulfate) | 0.73 |
| Example 89 | 0.43 |
| Example 133 | 0.20 |
| Example 169 | 0.48 |
| Example 170 | 0.50 |
| Example 171 | 1.01 |
| Example 208 | 0.27 |
| Example 210 | 0.52 |

TABLE 1-continued

| Suppressing Action to NECA-Stimulated [Saccharogenesis] *Glucose Production* in Hepatic Cells of Primary Culture of Rats | |
|---|---|
| Example 215 | 0.22 |
| Example 235 | 1.27 |

2) Action to Hyperglycemia of Spontaneous Diabetic Mice (KK-$A^y$/Ta Jcl) (Single Administration)

Animals: Five male KK-$A^y$/Ta Jcl mice for each group (purchased from Nippon Clair)

Preparation and Administration of Test Compound: A test compound in a dose as shown in Table 1 was suspended in a 0.5% aqueous solution of methyl cellulose and was orally administered in a [dose] *volume* of 10 ml/kg.

Collection of Blood Samples and Determination of Blood [Sugar:] *Glucose:* Blood was collected from tail vein immediately before adminstration of the test compound and also five hours after the administration and blood [sugar] *glucose* was determined.

Method: Tail vein of a mouse was injured by a razor without an anesthetization to bleed slightly. The blood (15 μl) was collected and immediately mixed with 135 μl of a 0.6 M perchloric acid. Glucose in the supernatant obtained by a centrifugal separation (at 1500 g for 10 minutes at 4° C. using a cooling centrifuge GS-6KR of Beckmann) was determined by a Glucose CII Test Wako (Wako Pure Chemicals).

The result for each experiment is shown in Table 2-1 to 2–3.

The result is shown in terms of "(% ratio of the blood [sugar] *glucose* after 5 hours from the administration to the blood [sugar] *glucose* before the administration)±(standard error)". The data were subjected to a one-way layout analysis of variance and then subjected to a multiple comparison of a Dunnett type. The case where $p<0.05$ was judged to be that a significant difference was available.

TABLE 2-1

| Action of spontaneous diabetic mice (KK-$A^7$/Ta Jcl) to hyperglycemia | | | |
|---|---|---|---|
| Test Compound | Dose (mg/kg) | $\frac{\text{Blood sugar level 5 hr after the administration}}{\text{Blood sugar level immediately before the administration}} \times 100$ | Significance |
| Solvent | | 72.4 ± 4.4 | |
| Example 8 (sulfate) | 10 | 47.8 ± 4.8 | ** |
| Example 19 | 10 | 51.8 ± 2.9 | ** |

(**; $p < 0.01$ vs. Solvent)

TABLE 2-2

| Action of spontaneous diabetic mice (KK-$A^7$/Ta Jcl) to hyperglycemia | | | |
|---|---|---|---|
| Test Compound | Dose (mg/kg) | $\frac{\text{Blood sugar level 5 hr after the administration}}{\text{Blood sugar level before the administration}} \times 100$ | Significance |
| Solvent | | 67.6 ± 2.4 | |
| Example 64 | 10 | 42.3 ± 4.8 | ** |
| Example 89 | 30 | 38.3 ± 4.4 | ** |

(**; $p < 0.01$ vs. Solvent)

TABLE 2-3

| Action of Spontaneous Diabetic Mice (KK-$A^7$/Ta Jcl) to hyperglycemia | | | |
|---|---|---|---|
| Test Compound | Dose (mg/kg) | $\frac{\text{Blood sugar level 5 hr after the administration}}{\text{Blood sugar level before the administration}} \times 100$ | Significance |
| Solvent | | 70.7 ± 4.6 | |
| Example 210 | 10 | 51.5 ± 4.6 | * |

(*; $p < 0.05$ vs. Solvent)

As such, the compounds of the present invention showed a clear effect to the pathological models. In addition, the compounds of the present invention showed an improving action in the investigation for impaired glucose tolerance in a glucose tolerance test and were confirmed to act not only in liver but also in periphery.

Now, representative compounds of the novel purine compounds according to the present invention will be illustrated and it goes without saying that the object is to facilitate the understanding of the present invention and that the present invention is not limited thereby.

EXAMPLE 1

3-{6-Amino-8-(3-fluorophenyl)-2-[2-(1-hydroxycyclohexyl)-1-ethynyl]-9H-9-purinyl}benzonitrile 1) $N^1$-[4-(3-Cyanoanilino)-5-nitro-6-oxo-1,6-dihydro-2-pyrimidinyl]acetamide To a solution of 2.54 g of 3-cyanoaniline in 25 ml of tetrahydrofuran were gradually added 1.23 ml of acetic acid at 0° C. To this solution were added 2 g of 4-chloro-5-nitro-6-oxo-1,6-dihydro-2-pyrimidinylacetamide at 0° C. and the mixture was stirred for 3.5 hours. The reaction solution was filtered and the solid collected thereby was washed with 10 ml each of water, methanol, tetrahydrofuran and ether successively. The resulting product was dried at room temperature to give 2.58 g of $N^1$-[4-(3-cyanoanilino)-5-nitro-6-oxo-1,6-dihydro-2-pyrimidinyl]acetamide. The yield was 96%.

NMR (400 MHz, [δ, $d_6$-DMSO);] δ, *DMSO-$d_6$*); 2.18 (s, 3H), 7.56–7.60 (m, 1H), 7.67–7.70 (m, 1H), 7.83–7.87 (m, 1H), 8.07 (s, 1H), 11.05 (s, 1H), 11.69 (br s, 2H).

2) $N^1$-[4-Chloro-6-(3-cyanoanilino)-5-nitro-2-pyrimidinyl] acetamide $N^1$-[4-(3-Cyanoanilino)-5-nitro-6-oxo-1,6-dihydro-2-pyrimidinyl]acetamide (2.5 g) was suspended in 50 ml of acetonitrile, then 2.64 g of tetraethylammonium chloride, 1 ml of N,N-dimethylaniline and 4.5 ml of phosphorus oxychloride were added and the mixture was heated under reflux for 5 hours. The reaction solution was returned to room temperature and added to ice-water and the mixture was stirred for 30 minutes. The resulting crystals were collected by filtration washed with water and dried to give 2.5 g of $N^1$-[4-chloro-6-(3-cyanoanilino)-5-nitro-2-pyrimidinyl] acetamide. The yield was 93%.

NMR (400 MHz, [δ, $d_6$-DMSO);] δ, *DMSO-$d_6$*) 2.18 (s, 3H), 7.56–7.60 (m, 1H), 7.67–7.70 (m, 1H), 7.83–7.87 (m, 1H), 8.07 (s, 1H), 11.05 (s, 1H), 11.69 (br s, 2H).

2) 3-[(2,5-Diamino-6-chloro-4-pyrimidinyl)amino] benzontrile $N^1$-[4-Chloro-6-(3-cyanoanilino)-5-nitro-2-pyrimidinyl] acetamide (2.37 g) was dissolved in 237 ml of ethanol, 8.04 g of stannous chloride was added and then 135 mg of sodium borohydride was added thereto with heating at 60° C. After stirring at 60° C. for 3 hours, the mixture was returned to room temperature and concentrated to dryness. The resulting residue was diluted with water and the resulting precipitates were collected by filtration and washed with water to give 3.2 g of crude crystals of 3-[(2,5-Diamino-6-chloro-4-pyrimidinyl)amino]benzonitrile. This was used for the next step without purification.

NMR (400 MHz, [δ, $d_6$-DMSO);] δ, *DMSO-$d_6$*); 4.24 (s, 2H), 6.08 (s, 2H), 7.38–7.42 (m, 1H), 7.44–7.49 (m, 1H), 7.97–8.02 (m, 1H), 8.31–8.34 (m, 1H), 8.62 (s, 1H).

4) 3-[2-Amino-6-chloro-8-(3-fluorophenyl)-9H-9-purinyl] benzonitrile

Crude crystals (3.2 g) of 3-[(2,5-diamino-6-chloro-4-pyrimidinyl)amino]benzonitrile were dissolved in 64 ml of methanol, then 3.2 ml of acetic acid and 1.7 ml of 3-fluorobenzaldehyde were added thereto and the mixture was stirred at room temperature for 2 hours. The reaction solution was concentrated and was subjected to an azeotropy with toluene for two times. The resulting residue after concentration was dissolved in ethanol, a solution of 1.72 g of ferric chloride in 10 ml of ethanol was added and the mixture was heated under reflux for 1 hour. The reaction solution was returned to room temperature, concentrated to dryness and added to ice-water and the resulting crystals were collected by filtration to give 2.6 g of the title compound, i.e., 3-[2-amino-6-chloro-8-(3-fluorophenyl)-9H-9-purinyl]benzonitrile.

NMR (400 MHz, [δ,] δ, $CDCl_3$); 5.09 (s, 2H), 7.06–7.10 (m, 1H), 7.11–7.15 (m, 1H), 7.18–7.28 (m, 2H), 7.40–7.44 (m, 1H), 7.53–7.57 (m, 1H), 7.62–7.64 (m, 1H), 7.70–7.73 (m, 1H).

5) 3-[6-Chloro-8-(3-fluorophenyl-2-iodo-9H-9-purinyl] benzonitrile

3-[2-Amino-6-chloro-8-(3-fluorophenyl)-9H-9-purinyl]-benzonitrile (2.6 g) was dissolved in 105 ml of tetrahydrofuran, then 2.9 ml of isoamyl nitrite, 5.8 ml of diiodomethane and 1.37 g of cuprous iodide were added thereto and the mixture was heated under reflux for 1 hour. After the resulting mixture was cooled to room temperature, it was filtered to remove unnecessary substances and washed with 100 ml of ethyl acetate. The filtrate was concentrated to dryness and purified by a silica gel column (50 g of silica gel). It was eluted with ethyl acetate and hexane (1:1). The fractions containing the aimed product were collected, concentrated and suspended in 100 ml of a mixed solvent of ethyl acetate and hexane (1:4), and the resulting precipitates were collected by filtration to give 1.7 g of 3-[(6-chloro-8-(3-fluorophenyl)-2-iodo-9H-9-purinyl]benzonitrile. The yield was 50%.

NMR (400 MHz, [δ,] δ, $CDCl_3$); 7.19–7.27 (m, 2H), 7.31–7.40 (m, 2H), 7.57–7.60 (m, 1H), 7.64–7.66 (m, 1H), 7.53–7.57 (m, 1H), 7.68–7.72 (m, 1H), 7.84–7.87 (m, 1H), 6) 3-{6-Chloro-8-(3-fluorophenyl)-2-[2-(1-hydroxycyclohexyl)-1-ethynyl]-9H-9-purinyl}benzonitrile 1-3-[6-Chloro-8-(3-fluorophenyl)-2-iodo-9H-9-purinyl] benzonitrile (2.1 g) was dissolved in 54 ml of dioxane, then 660 mg of 1-ethynylcyclohexanol, 310 mg of bis-triphenylphosphine palladium dichloride, 169 mg of cuprous iodide and 0.39 ml of trethylamine were added thereto and the mixture was stirred at room temperature in a nitrogen atmosphere for hours. The reaction solution was diluted with 100 ml of dichloromethane and washed with 100 ml of a saturated ethylenediaminetetraacetic acid. The organic layer was washed with 20 ml of brine and dried over anhydrous sodium sulfate. After the resulting solution was concentrated to dryness, the resulting residue was suspended in 100 ml of dichloromethane and the resulting crystals were collected by filtration to give 1.8 g of 3-{6-chloro-8-(3-fluorophenyl)-2-[2-(1-hydroxycyclohexyl)-1-ethynyl]-9H 9-purinyl}benzonitrile. The yield was 86%. NMR (400 MHz, [δ,] δ, $CDCl_3$); 1.27–1.40 (m, 1H), 1.57–1.78 (m, 7H), 2.01–2.08 (m, 2H), 2.13 (s, 1H), 7.18–7.24 (m, 1H), 7.25–7.28 (m, 1H), 7.32–7.40 (m, 2H), 7.55–7.58 (m, 1H), 7.66–7.72 (m, 2H), 7.83–7.86 (m, 1H).

7) 3-[6-Amino-8-(3-fluorophenyl)-2-[2-(1-hydroxyhexyl)-1-ethynyl]-9H-9-purinyl]benzonitrile 3-{6-Chloro-8-(3-fluorophenyl)-2-[2-(1-hydroxycyclohexyl)-1-ethynyl}-9H-9-purinyl]benzonitrile (2.0 g) was suspended in 200 ml of a 20% ammonia/ethanol and reacted at 100° C. in an autoclave for 8 hours. The resulting mixture was cooled to room temperature, concentrated to dryness and purified by a silica gel column (40 g of silica gel). It was eluted with dichloromethane containing 5% of methanol. The fractions containing the aimed product were collected, concentrate to dryness, suspended in 100 ml of a mixed solvent of ethyl acetate and hexane (1:1) and the resulting product was collected by filtration and washed with hexane to give 1.4 g of the title compound. The yield was 73%.

NMR (400 MHz, [δ, $d_6$-DMSO);] δ, *DMSO-$d_6$*); 1.26–1.41 (m, 1H), 1.46–1.75 (m, 7H); 1.99–2.07 (m, 2H), 2.32 (s, 1H), 5.81 (br s, 2H), 7.12–7.18 (m, 2H), 7.21–7.25 (m, 1H), 7.30–7.36 (m, 1H), 7.54–7.57 (m, 1H), 7.60–7.64 (m, 1H), 7.68–7.70 (m, 1H), 7.75–7.79 (m, 1H).

Compounds of Example 2 to Example 11 were synthesized by the same manner as in Example 1 using the corresponding material and they were all obtained as hydrochlorides by a conventional method.

EXAMPLE 2

1-{2-[6-Amino-8-(3-fluorophenyl)-9-phenyl-9H-2-purinyl]-1-ethynyl}1-cyclohexenol Hydrochloride NMR (400 MHz, [δ, $d_6$-DMSO);] δ, *DMSO-$d_6$*); 1.16–1.28 (m, 1H) 1.37–1.63 (m, 7H), 1.72–1.80 (m, 2H), 7.22–7.26 (m, 3H), 7.36–7.42 (m, 3H), 7.50–7.57 (m, 3H), 7.68 (br s, 1H). FAB MASS; 428 ($M^+$+1).

EXAMPLE 3

1-{2-[6-Amino-9-[4-(dimetylamino)phenyl]-8-(3-fluorophenyl)-9H-2-purinyl]-1-ethynyl}-1-cyclohexanol Dihydrochloride NMR (400 MHz, [δ, $d_6$-DMSO);] δ, *DMSO-$d_6$*); 1.20–1.28 (m, 1H), 1.38–1.62 (m, 7H), 1.74–1.82 (m, 2H), 2.98 (s, 6H), [6.87 (d, J=8.7 Hz, 2H), 7.14 (d, J=8.7 Hz, 2H),] *6.87 (d, J=8.7 Hz, 2H), 7.14 (d, J=8.7 Hz, 2H)*, 7.23–7.33 (m, 3H), 7.90–8.45 (m, 1H), m.p.; 255–260° C.; FAB MASS; 471 ($M^+$+1).

EXAMPLE 4

1-[6-Amino-8-(3-fluorophenyl)-9-(4-morpholinophenyl)-9H-2-purinyl]-1-ethynyl}-1-cyclohexanol Dihydrochloride NMR (400 MHz, [δ, $d_6$-DMSO);] δ, *DMSO-$d_6$*); 1.20–1.30 (m, 1H), 1.40–1.64 (m, 7H), 1.74–1.82 (m, 2H), 3.20 (br, 4H), 3.76 (br, 4H), [7.06 (d, J=9.2 Hz, 2H), 7.23 (d, J=9.2 Hz, 2H),] *7.06 (d, J=9.2 Hz, 2H)*, *7.23 (d, J=9.2 Hz, 2H)*, 7.24–7.34 (m, 3H), 7.39–7.45 (m, 1H). FAB MASS; 513 ($M^+$+1).

EXAMPLE 5

1-{2-[6-Amino-8-(3-fluorophenyl)-9-(4-methoxyphenyl)-9H-2-purinyl]-1-ethynyl}-1-cyclohexanol Hydrochloride NMR (400 MHz, [δ, $d_6$-DMSO);] δ, *DMSO-$d_6$*); 1.17–1.28 (m, 1H), 1.40–1.64 (m, 7H) 1.75–1.84 (m, 2H), 3.80 (s, 3H), [7.08 (d, J=8.3 Hz, 2H), 7.26–7.29 (m, 3H), 7.34 (d, J=8.3 Hz, 2H),] *7.08 (d, J=8.3 Hz, 2H)*, *7.26–7.29 (m, 3H)*, *7.34 (d, J=8.3 Hz, 2H)*, 7.39–7.45 (m, 1H), FAB MASS; 458 ($M^+$+1).

EXAMPLE 6

2-Amino-5-{6-amino-8-(3-fluorophenyl)-2-[2-(1-hydroxycyclohexyl)-1-ethynyl]-9H-9-purinyl}benzonitrile Dihydrochloride NMR (400 MHz, [δ, $d_6$-DMSO);] δ, *DMSO-$d_6$*); 1.16–1.30 (m, 1H), 1.35–1.64 (m, 7H), 1.72–1.85 (m, 2H), [6.85 (d, J=9.0 Hz, 1H),] *6.85 (d, J=9.0 Hz, 1H)*, 7.25–7.36 (m, 4H), 7.42–7.49 (m, 1H), [7.55 (d, J=2.4 Hz, 1H).] *7.55 (d, J=2.4 Hz, 1H)*. FAB MASS 458 ($M^+$+1).

EXAMPLE 7

4-{(6-Amino-8-(3-fluorophenyl)-2-[2-(1-hydroxycyclohexyl)-1-ethynyl]-9H-9-purinyl}benzonitrile Hydrochloride NMR (400 MHz, [δ, $d_6$-DMSO);] δ, *DMSO-$d_6$*); 1.17–1.28 (m, 1H), 1.36–1.64 (m, 7H), 1.73–1.81 (m, 2H), 7.18–7.20 (m, 1H), 7.27–7.32 (m, 2H), 7.39–7.45 (m, 1H), [7.64 (d, J=8.4 Hz, 2H), 8.04 (d, J=8.4 Hz, 2H).] *7.64 (d, J=8.4 Hz, 2H)*, *8.04 (d, J=8.4 Hz, 2H)*. FAB MASS; 453 ($M^+$+1).

EXAMPLE 8

1-{2-[6-Amino-9-ethyl-8-(3-fluorophenyl)-9H-2-purinyl]-1-ethynyl}-1-cyclobutanol Hydrochloride NMR (400 MHz, [δ, $d_6$-DMSO); 1.33 (t, J=7.2 Hz, 3H),] *1.33 (t, J=7.2 Hz, 3H)*, 1.78–1.90 (m, 2H), 2.20–2.36 (m, 2H), 2.40–2.50 (m, 2H), [4.39 (q, J=7.2 Hz, 2H),] *4.39 (q, J=7.2 Hz, 2H)*, 6.19 (s, 1H), 7.51–7.57 (m, 1H), 7.70–7.76 (m, 3H). FAB MASS; 352 ($M^+$+1); m.p.; 160–163° C.

EXAMPLE 9

1-[(6-Amino-9-ethyl-8-(3-fluorophenyl)-9H-2-purinyl]-3-ethyl-1-pentyn-3-ol Hydrochloride NMR (400 MHz, [δ, $d_6$-DMSO); 1.01 (t, J=7.2 Hz, 6H), 1.27 (t, J=7.2 Hz, 3H),] δ, *DMSO-$d_6$*); *1.01 (t, J=7.2 Hz, 6H)*, *1.27 (t, J=7.2 Hz, 3H)*, 1.60–1.75 (m, 4H), [4.30 (q, J=7.2 Hz, 2H),] *4.30 (q, J=7.2 Hz, 2H)*, 7.44–7.50 (m, 1H), 7.63–7.70 (m, 3H). FAB MASS; 368 ($M^+$+1); m.p.; 150–153° C.

EXAMPLE 10

4-[6-Amino-9-ethyl-8-(3-fluorophenyl)-9H-2-purinyl]-2-methyl-1-buthyn-2-ol Hydrochloride NMR (400 MHz, [δ, $d_6$-DMSO); 1.32 (t, J=7.2 Hz, 3H),] δ, *DMSO-$d_6$*); *1.32 (t, J=7.2 Hz, 3H)*, 1.52 (s, 6H), [4.39 (q, J=7.2 Hz, 2H),] *4.39 (q, J=7.2 Hz, 2H)*, 5.76 (s, 1H), 7.51–7.57 (m, 1H), 7.60–7.75 (m, 3H). FAB MASS; 340 ($M^+$+1); m.p.; 193–196° C.

EXAMPLE 11

Ethyl 3-{6-Amino-8-(3-fluorophenyl)-2-[2-(1-hydroxycyclohexyl)-1-ethynyl]-9H-9-purinyl}benzoate NMR (400 MHz, [δ,] δ, $CDCl_3$); 1.24–1.42 (m, 1H), [1.37 (t, J=7.1 Hz, 3H),] *1.37 (t, J=7.1 Hz, 3H)*, 1.47–1.55 (m, 1H), 1.46–1.78 (m, 6H), 1.97–2.08 (m, 2H), 2.48 (s, 1H), [4.37 (q, J=7.1 Hz, 2H),] *4.37 (q, J=7.1 Hz, 2H)*, 5.83 (br s, 2H), 7.06–7.12 (m, 1H), 7.17–7.21 (m, 1H), 7.22–7.31 (m, 2H), 7.48–7.53 (m, 1H), [7.58 (t, J=7.8 Hz, 1H),] *7.58 (t, J=7.8 Hz, 1H)*, 7.98–8.02 (m, 1H), 8.14–8.18 (m, 1H).

EXAMPLE 12

3-{6-Amino-8-(3-fluorophenyl)-2-[2-(1-hydroxycylohexyl)-1-ethynyl]-9H-9-purinyl}benzamide Hydrochloride 3-{6-Amino-8-(3-fluorophenyl)-2-[2-(1-hydroxycyclohexyl)-1-ethynyl]-9H-9-purinyl}benzonitrile (1.4 g) obtained in Example 1 was dissolved in 70 ml of methanol, then 1.55 ml of a 30% aqueous hydrogen peroxide and 1.55 ml of a 1N aqueous solution of sodium hydroxide were added thereto and the mixture was stirred for 4 hours. The resulting crystals were collected by filtration, washed with water and dried to give 1.14 g of a free compound of the title compound. The free compound was suspended in 30 ml of ethanol, 5 ml of a 6N aqueous solution of hydrochloric acid were added and the mixture was concentrated to dryness. The resulting residue was suspended in 50 ml of diethyl ether, filtered, washed and then dried to give 1.2 g of the title compound. The yield was 76%.

NMR (400 MHz, [δ, $d_6$-DMSO);] δ, *DMSO-$d_6$*); 1.15–1.28 (m, 1H), 1.25–1.63 (m, 7H), 1.72–1.80 (M, 2H), 7.22–7.30 (m, 3H), 7.37–7.43 (m, 1H), 7.54–7.58 (m, 1H), 7.60–7.64 (m, 1H), 7.77 (br s, 1H), 7.89–7.91 (m, 1H), 8.01–8.04 (m, 1H), 8.08 (s, 1H), FAB MASS; 471 ($M^+$+1).

Compounds of Examples 13 and 14 were obtained by the same manner as in Example 12.

EXAMPLE 13

4-{6-Amino-8-(3-fluorophenyl)-2-[2-(1-hydroxycyclohexyl)-1-ethynyl}-9H-9-purinyl] benzamide Hydrochloride NMR (400 MHz, [δ, $d_6$-DMSO);] δ, *DMSO-$d_6$*) 1.16–1.28 (m, 1H), 1.35–1.64 (m, 7H), 1.72–1.81 (m, 2H), 7.22–7.29 (m, 3H), 7.39–7.44 (m, 1H), [7.50 (d, J=8.2 Hz, 2H), 7.55 (s, 1H), 7.99 (d, J=8.2 Hz, 2H),] *7.50 (d, J=8.2 Hz, 2H)*, *7.55 (s, 1H)*, *7.99 (d, J=8.2 Hz, 2H)*, 8.13 (s, 1H. FAB MASS; 471 ($M^+$+1).

EXAMPLE 14

2-Amino-5-{6-amino-8-(3-fluorophenyl)-2-[2-(1-hydroxycyclohexyl--ethynyl}-9H-9-purinyl] benzamide Dihydrochloride NMR (400 MHz, [δ, $d_6$-DMSO);] δ, *DMSO-$d_6$*) 1.14–1.27 (m, 1H), 1.27–1.63 (m, 7H), 1.65–1.82 (m, 2H), 6.79–6.84 (m, 1H), 7.17–7.18 (m, 1H), 7.19 (br s, 1H), 7.24–7.30 (m, 1H), 7.33–7.38 (m, 2H), 7.42–7.48 (m, 1H), 7.60–7.63 (m, 1H), 7.72 (br s, 1H). FAB MASS; 486 ($M^+$+1).

EXAMPLE 15

1-{6-Amino-8-(3-fluorophenyl)-2-[2-(1-hydroxycyclohexyl)-1-ethynyl}9H-purinyl]benzoic Acid Hydrochloride An ethyl ester of Example 11 was dissolved in ethanol, a 1N aqueous solution of sodium hydroxide was added and the mixture was stirred at room temperature. After the reaction solution was concentrated, the resulting residue was dissolved in small amount of water, the solution was adjusted to pH 2 with 1N hydrochloric acid and the resulting crystals were collected by filtration and washed with water and ether to give the title compound.

NMR (400 MHz, [δ, $d_6$-DMSO);] δ, *DMSO-$d_6$*); 1.18–1.28 (m, 1H), 1.36–1.62 (m, 7H), 1.72–1.81 (m, 2H), 7.20–7.28 (m, 2H), 7.37–7.42 (m, 1H), 7.63–7.69 (m, 3H), 7.93–7.95 (m, 1H), 8.04–8.07 (m, 1H), FAB MASS; 472 ($M^+$+1).

EXAMPLE 16

4-{6-Amino-8-(3-fluorophenyl)-2-[2-(1-hydroxycyclohexyl)-1-ethynyl}-9H-9-purinyl] benzoic Acid Hydrochloride The title compound was obtained by the same manner as in Example 15.

NMR (400 MHz, [δ, $d_6$-DMSO);] δ, *DMSO-$d_6$*); 1.16–1.28 (m, 1H), 1.37–1.64 (m, 7H), 1.72–1.83 (m, 2H), 7.20–7.22 (m, 1H), 7.27–7.32 (m, 2H), 7.39–7.44 (m, 1H), [7.54 (d, J=8.4 Hz, 2H), 8.07 (d, J=8.4 Hz, 2H).] *7.54 (d, J=8.4 Hz, 2H), 8.07* (i d, J=8.4 Hz, 2H). FAB MASS; 472 ($M^+$+1).

EXAMPLE 17

3-{6-Amino-8-(3-fluorophenyl)-2-[2-(1-hydroxycyclohexyl)-1-ethynyl}-9H-9-purinyl] benzenecarboxamidine Dihydrochloride A cyano compound of Example 1 was treated with $MeAlClNH_2$ to give the title compound.

NMR (400 MHz, [δ,] δ,$CD_3OD$); 1.34–1.47 (m, 1H), 1.60–1.86 (m, 7H), 2.00–2.11 (m, 2H), 7.26–7.34 (m, 1H), 7.36–7.52 (m, 3H), 7.62–7.67 (m, 1H), 7.78–7.84 (m, 1H), 8.02–8.08 (m, 1H), 8.13–8.17 (m, 1H), FAB MASS; 470 ($M^+$+1).

EXAMPLE 18

$N^2$-Cyano-{3-{6-amino-8-(3-fluorophenyl)-2-[2-(1-hydroxycyclohexyl)-1-ethynyl]-9H-9-purinyl}benzene}carboxamidine Dihydrochloride 3-[6-Chloro-8-(3-fluorophenyl)-2-iodo-9H-9-purinyl] benzonitrile obtained in the fourth step of Example 1 was treated with ammonia to give 3-{6-amino-8-(3-fluorophenyl)-2-iodo-9H-9-purinyl}benzonitrile. This was treated with hydrogen sulfide to convert the cyano group to thioamide and then alkylated with iodomethane to give a methyl thioimidate. This was reacted with cyanamide to give $N^2$-cyano-{3-[6-amino-8-(3-fluorophenyl)-2-iodo-9H-9-purinyl]-benzene}carboxamidine. After that, like in the sixth step of Example 1, the resulting compound was dissolved in dioxane, then 1-ethynylcyclohexanol, bis-triphenylphosphine palladium dichloride, cuprous iodide and triethylamine were added thereto and the mixture was reacted at room temperature in a nitrogen atmosphere to give the title compound.

NMR (400 MHz, [δ,] δ, $CD_3OD$); 1.37–1.49 (m, 1H), 1.59–1.88 (m, 7H), 2.02–2.13 (m, 2H), 7.29–7.35 (m, 1H), 7.36–7.40 (m, 1H), 7.44–7.51 (m, 2H), [7.79 (t, J=8.1 Hz, 1H),] *7.79 (t, J=8.1 Hz, 1H),* 8.09–8.14 (m, 1H), 8.17–8.24 (m, 1H). FAB MASS; 495 ($M^+$+1).

EXAMPLE 19

1-{2-[6-Amino-8-(3-fluorophenyl)-9-methyl-9H-2-purinyl]-1-ethynyl}-1-cyclopentanol Sulfate 1) $N^1$-(4-Chloro-6-methylamino-5-nitro-2-pyrimidinyl) acetamide A mixed solution (reagent A) of 2 liters of a 40% aqueous solution of methylamine and 1.5 liters of acetic acid previously prepared at not higher than 10° C. was weighed and taken out in an amount of 1.8 liters and added dropwise into a solution of 1.5 kg of $N^1$-(4,6-dichloro-5-nitro-2-pyrimidinyl)acetamide in 15 liters of tetrahydrofuran with stirring under ice-cooling over 1 hour. The addition was carried out keeping the bulk temperature at 4° C. or lower. After the mixture was stirred for 30 minutes under ice-cooling, 450 ml of the reagent. A was further added. After further 30 minutes, 450 ml of the reagent A was added again followed by stirring for 40 minutes. Ice (4.5 kg) was added to the reaction mixture followed by adding 10 liters of cold water. The resulting crystals were collected by filtration and washed with 1 liter of water twice and with 1 liter of ether twice. Then it was dried at 50° C. for 6 hours to give 1253 g of $N^1$-(4-Chloro-6-methylamino-5-nitro-2-pyrimidinyl) acetamide. The yield was 85%.

NMR (400 MHz, [δ, $d_6$-DMSO);] δ, *DMSO-$d_6$*); 2.27 (s, 3H), [2.97 (d, J=4.4 Hz, 3H), 8.55 (d, J=4.4 Hz, 1H),] *2.97 (d, J=4.4 Hz, 3H), 8.55 (d, J=4.4 Hz, 1H),* 10.80 (s, 1H).

2) 6-Chloro-8-(3-fluorophenyl)-9-methyl-9H-2-purinylamine $N^1$-(4-Chloro-6-methylamino-5-nitro-2-pyrimidinyl) acetamide (2050 g) was suspended in 20 liters of methanol, 2 liters of acetic acid were added and 2 kg of Raney nickel (used after washing with water and methanol) were added and the mixture was stirred in hydrogen for 12 hours. The reaction solution was diluted with 20 liters of tetrahydrofuran and filtered through Celite. The residue was washed with methanol for three times (3×1 liter), then washed with a mixed solvent of methanol and tetrahydrofuran (1:1) and combined with the filtrate and the mixture was concentrated to dryness. The resulting residue was subjected to an azeotropy with toluene, the residue was dissolved in 20 liters of methanol, then 276 ml of acetic acid and 1 liter of 3-fluorobenzaldehyde were added and the mixture was stirred at room temperature for 12 hours. The reaction solution was concentrated and subjected to an azeotropy with toluene. Concentrated residue was suspended in 17 liters of ethanol, 3 liters of ethanol solution of 1.5 kg of anhydrous ferric chloride were added and the mixture was heated under reflux for 1 hour. The reaction solution was returned to room temperature and concentrated to dryness and the residue was diluted with 12 liters of ethyl acetate followed by washing with 12 liters of water and 4.5 liters of brine. The organic layer was concentrated to dryness, the residue was dissolved in 10 liters of tetrahydrofuran, 1.96 liters of a 1N hydrochloric acid were added thereto and the mixture was heated under reflux for 30 minutes. The reaction solution was cooled to room temperature, 10 kg of ice were added and the mixture was further diluted with 10 liters of water. The resulting crystals were collected by filtration and washed with water twice (2×1 liter) and with ether twice (2×1 liter) to give 1.0 kg of 6-chloro-8-(3-fluorophenyl)-9-methyl-9H-2-purinyl-amine. The overall yield was 47%.

NMR (400 MHz, [δ, $d_6$-DMSO);] δ, *DMSO-$d_6$);* 3.73 (s, 3H), 7.01 (s, 2H), 7.40–7.46 (m, 1H), 7.60–7.66 (m, 1H), 7.68–7.74 (m, 2H).

3) 6-Chloro-8-(3-fluorophenyl)-2-iodo-9-methyl-9H-purine

6-Chloro-8-(3-fluorophenyl)-9-methyl-9H-2-purinylamine (960 g) was dissolved in 9.6 liters of tetrahydrofuran and then 774.3 g of cuprous iodide and 1.49 liters of diodomethane were added thereto. Isoamyl nitrite (1.49 liters) was added dropwise during 1 hour into the mixture with heating under reflux. The reaction solution was heated under reflux for 15 minutes, cooled, diluted with 4 liters of ethyl acetate and then filtered through Celite followed by washing with ethyl acetate three times (3×2 liters). The filtrate and the washings were combined and washed with 8 liters of water and 8 liters of brine. The organic layer was dried over 2 kg of anhydrous sodium sulfate and concentrated to about 3 liters. The concentrated solution was diluted with 10 liters of hexane and the resulting crystals were filtered and washed with 1 liter of hexane. The crystals were then dried at 50° C. for 4 hours to give 1076 g of 6-chloro-8-(3-fluorophenyl)-2-iodo-9-methyl-9H-purine. The yield was 75%.

NMR (400 MHz, [δ, $d_6$-DMSO);] δ, *DMSO-$d_6$);* 3.89 (s, 3H), 7.49–7.56 (m, 1H), 7.66–7.72 (m, 1H), 7.76–7.82 (m, 2H).

4) 1-{2-[6-Chloro-8-(3-fluorophenyl)-9-methyl-9H-2-purinyl]-1-ethynyl}-1-cyclopentanol 6-Chloro-8-(3-fluorophenyl)-2-iodo-9-methyl-9H-purine (1076 g) was dissolved in 10 liters of tetrahydrofuran and 97.2 g of bistriphenylphosphine palladium dichloride, 26.4 g of cuprous iodide and 248 g of 1-ethynylcyclopentanol were added thereto. Into this mixture were added dropwise 331 ml of triethylamine within 15 minutes keeping the bulk temperature at not higher than 26° C. in a nitrogen atmosphere. After reacting at room temperature for 4 hours, the reaction solution was diluted with 10 liters of ethyl acetate and washed with 4 liters of a saturated ammonium chloride solution and 1 liter of brine. The organic layer was dried over 2 kg of anhydrous sodium sulfate and filtered followed by concentrating to an extent of 3 liters. The resulting residue was diluted with 4 liters of hexane-ethyl acetate (1:1), filtered and washed with 1 liter of hexane to give 732 g of 1-{2-[6-chloro-8-(3-fluorophenyl)-9-methyl-9H-2-purinyl]-1-ethynyl}-1-cyclopentanol. The yield was 88%.

NMR (400 MHz, [δ, $d_6$-DMSO);] δ, *DMSO-$d_6$);* 1.67–1.85 (m, 4H), 1.87–2.03 (m, 4H), 3.92 (s, 3H), 5.61 (s, 1H), 7.50–7.56 (m, 1H), 7.66–7.73 (m, 1H), 7.78–7.84 (m, 2H).

5) 1-{2-[6-Amino-8-(3-fluorophenyl)-9-methyl-9H-2-purinyl]-1-ethynyl}-1-cyclopentanol 1-{2-[6-Chloro-8-(3-fluorophenyl)-9-methyl-9H-2-purinyl)-1-ethynyl}-1-cyclopentanol (732 g) was dissolved in 16 liters of dimethoxyethane, 8 liters of a concentrated aqueous ammonia were added and the mixture was stirred at 70° C. for 5 hours using a sealed tube reactor. After the reaction solution was cooled in room temperature, it was diluted with 20 liters of ethyl acetate and washed with water twice (8 liters and 4 liters). The organic layer was concentrated to about 15 liters and the resulting residue was diluted with 15 liters of hexane, filtered and washed with hexane twice. Then it was dried at 50° C. for 2.5 hours to give 620 g of the product. The yield was 89%.

NMR (400 MHz, [δ, $d_6$-DMSO);] δ, *DMSO-$d_6$);* 1.62–1.78 (m, 4H), 1.79–1.95 (m, 4H), 3.78 (s, 3H), 5.41 (br s, 1H), 7.36–7.50 (m, 3H), 7.58–7.72 (m, 3H).

6) 1-{2-[6-Amino-8-(3-fluorophenyl)-9-methyl-9H-2-purinyl}-1-ethynyl]-1-cyclopentanol Sulfate 1-{2-(6-Amino-8-(3-fluorophenyl)-9-methyl-9H-2-purinyl]-1-ethynyl}-1-cyclopentanol (1.59 g) was suspended in 10 mL of methanol and 1 mL of a methanol solution of 440 mg of concentrated sulfuric acid was added dropwise thereinto at room temperature. The resulting solution was evaporated until the amount of the solution became about one half followed by adding 4 mL of ether thereto. The resulting crystals were collected by filtration, washed with ether and dried to give 1.79 g of the sulfate.

NMR (400 MHz, [δ, $d_6$-DMSO);] δ, *DMSO-$d_6$);* 1.62–1.80 (m, 4H), 1.82–1.98 (m, 4H), 3.80 (s, 3H), 7.40–7.46 (m, 1H), 7.60–7.72 (m, 3H), 8.01–8.03 (m, 1H).

A hydrochloride was prepared by a conventional method.

NMR (400 MHz, [δ, $d_6$-DMSO);] δ, *DMSO-$d_6$);* 1.66–1.82 (m, 4H), 1.87–2.00 (m, 4H), 3.86 (s, 3H), 7.43–7.50 (m, 1H), 7.63–7.70 (m, 1H), 7.71–7.77 (m, 2H). FAB MS; 352 ($M^+$+1); m.p.; 230–232° C.

The compounds of Examples 20–68, 70–201, 203 and 205 were prepared by the same manner as in Example 19 using the corresponding materials.

EXAMPLE 20

4-[-Amino-8-(2-furyl)-9-methyl-9H-2-purinyl]-3-butyn-1-ol Hydrochloride

NMR (400 MHz, [δ, $d_6$-DMSO); 2.58 (t, J=6.7 Hz, 2H), 3.59 (t, J=6.7 Hz, 2H), 3.88 (s, 3H), 6.77 (dd, J=1.7 Hz, 3.6 Hz, 1H), 7.25 (d, J=3.6 Hz, 1H), 8.00 (d, J=1.7 Hz, 1H).] δ, *DMSO-$d_6$); 2.58 (t, J=6.7 Hz, 2H), 3.59 (t, =6.7 Hz, 2H), 3.88 (s, 3H), 6.77 (dd, J=1.7 Hz, 3.6 Hz, 1H), 7.25 (d, J=3.6 Hz, 1H), 8.00 (d, J=1.7 Hz, 1H).* m.p.; 161–164° C.

EXAMPLE 21

8-(2-Furyl)-2-(1-hexynyl)-9-methyl-9H-6-purineamine Hydrochloride

NMR (400 MHz, [δ, $d_6$-DMSO); 2.62 (t, J=6.7 2H), 3.79 (t, J=6.7 2H),] *DMSO-$d_6$); 2.62 (t, J=6.7 2H), 3.79 (t, J=6.7 2H),* 3.98 (s, 3H), 6.60 (m, 1H), 7.10 (m, 1H), 7.62 (m, 2H). m.p.; 178–181° C.

EXAMPLE 22

N-[8-(2-Furyl)-9-methyl-2-(2-phenyl-1-thienyl)-9H-6-pyrinyl]-N-phenethylamine Hydrochloride NMR (400 MHz, [δ,] δ, $CDCl_3$); 3.10 (br, 2H), 4.12 (s, 3H), 3.98 (s, 3H), 4.19 (br, 1H), 4.38 (m, 2H), 6.68 (m, 1H), 6.72 (br, 1H), 7.20–7.53 (m, 9H). m.p.; 148–151° C.

EXAMPLE 23

4-[6-Amino-8-(2-furyl)-9-methyl-9H-2-piurinyl]-3-butyn-2-ol

NMR (400 MHz, [δ, $d_6$-DMSO); 1.36 (d, J=7.5 Hz, 3H),] δ, *DMSO-$d_6$); 1.36 (d, J=7.5 Hz, 3H),* 3.84 (s, 3H), 4.45–4.60 (m, 1H), [5.56 (d, J=7.5 Hz, 1H),] *5.56 (d, J=7.5 Hz, 1H),* 6.74 (m, 1H), [(7.20 (d, J=3.5 Hz, 1H),] *7.20 (d, J=3.5 Hz, 1H),* 7.46 (s, 2H), 7.98 (s, 1H).

EXAMPLE 24

1-[6-Amino-8-(2-furyl)-9-ethyl-9H-2-purinyl]-4-methyl-1-pentyn-3-ol

NMR (400 MHz, [δ, $d_6$-DMSO); 0.96 (t, J=7.5 Hz, 6H),] δ, *DMSO-$d_6$); 0.96 (t, J=7.5 Hz, 6H),* 1.76–1.86 (m, 1H), 3.84 (s, 3H), 4.20 (m, 1H), [5.52 (d, J=7.5 Hz, 1H), 6.76 (dd, J=1.5 Hz, 3.7 Hz, 1H), 7.20 (d, J=3.7 Hz, 1H),] *5.52* (d, J=7.5 Hz, 1H), *6.76* (*dd, J=1.5 Hz, 3.7 Hz, 1H*), *7.20* (*d, J=3.7 Hz, 1H*), 7.46 (br, 2H), 7.97 (m, 1H), m.p.; 148–152° C.

EXAMPLE 25

1-{2-[6-Amino-8-(2-furyl)-9-methyl-9H-2-purinyl]-1-ethynyl}-1-cyclopentanol Hydrochloride NMR (400 MHz, [δ, $d_6$-DMSO);] δ, *DMSO-$d_6$*); 1.62–1.98 (m, 8H), 3.88 (s, 3H), 4.20 (m, 1H), [6.77 (dd, J=1.6 Hz, 3.5 Hz, 1H), 7.23 (d, J=3.5 Hz, 1H), 7.99 (d, J=1.6 Hz, 1H).] *6.77* (*dd, J=1.6 Hz, 3.5 Hz, 1H*), *7.23* (*d, J=3.5 Hz, 1H*), *7.99* )*d, J=1.6 Hz, 1H*). m.p.; 168–172° C.

EXAMPLE 26

1-{2-[6-Amino-8-(2-furyl)-9-methyl-9H-2-purinyl-1-ethynyl}-1-cyclohexanol Hydrochloride NMR (400 MHz, [δ, $d_6$-DMSO);] δ, *DMSO-$d_6$*); 1.21–1.34 (m, 1H), 1.43–1.70 (m, 7H), 1.82–1.90 (m, 2H), 3.90 (s, 3H), 6.78–6.81 (m, 1H, 7.25–7.28 (m, 1H), 8.01–8.03 (m, 1H). FAB MS; 338 ($M^+$+1).

EXAMPLE 27

4-[6-Amino-8-(2-furyl)-9-methyl-9H-2-purinyl]-2-methyl-3-butyn-2-ol Hydrochloride NMR (400 MHz, [δ, $d_6$-DMSO);] δ, *DMSO-$d_6$*); 1.48 (s, 6H), 3.90 (s, 3H), 6.78–6.81 (m, 1H), 7.22–7.28 (m, 1H), 8.00–8.03 (m, 1H). ESI MS; 298.1 ($M^+$+1).

EXAMPLE 28

1-{2-[6-Amino-8-(2-furyl)-9-phenyl-9H-2-purinyl]-1-ethynyl}-1cyclopentanol Hydrochloride NMR (400 MHz, [δ, $d_6$-DMSO);] δ, *DMSO-$d_6$*); 1.60–1.72 (m, 4H), 1.77–1.90 (m, 4H), [6.04 (d, J=3.3 Hz, 1H), 6.53 (dd, J=1.9,3.3 Hz, 1H), 7.48–7.50 (m, 2H), 7.61–7.63 (m, 3H), 7.81 (d, J=1.9 Hz, 1H.] *6.04* (*d, J=3.3 Hz, 1H*), *6.53* (*dd, J=1.9,3.3 Hz, 1H*)*7.48–7.50* (*m, 2H*), *7.61–7.63* (*m, 3H*), *7.81* (*d, J=1.9 Hz, 1H*). FAB MS; 386 ($M^+$+1).

EXAMPLE 29

1-[6-Ethoxy-8-(2-furyl)-9-methyl-9H-2-purinyl]-4-methyl-1-pentyn-3-ol

NMR (400 MHz, [δ,] δ, $CDCl_3$;) 1.13 [((dd, J=6.8 and 1.6 Hz, 6H), 1.52 (t, J=7.1 Hz, 1H), 4.70 (q, J=7.1 Hz, 2H),] (*dd, J=6.8 and 1.6 Hz, 6H*), *1.52* (*t, J=7.1 Hz, 1H*), *4.70* (*q, J=7.1 Hz, 2H*), 6.62–6.64 (m, 1H), 7.33–7.35 (m, 1H), 7.64–7.66 (m, 1H). FAB MS; 341 ($M^+$+1).

EXAMPLE 30

1-{2-6-Amino-9-methyl-8-phenyl-9H-2-purinyl]-1-ethynyl}-1-cyclohexanol Hydrochloride NMR (400 MHz, [δ, $d_6$-DMSO);] δ, *DMSO-$d_6$*); 1.20–1.32 (m, 1H), 1.44–1.66 (m, 7H), 1.81–1.88 (m, 2H), 3.79 (s, 3H), 7.57–7.60 (m, 3H), 7.85–7.88 (m, 2H). FAB MS; 348 ($M^+$+1).

EXAMPLE 31

1-{2-[6-Amino-8-(3-fluorophenyl)-9-methyl-9H-2-purinyl]1-ethynyl}-1-cyclohexanol Hydrochloride NMR (400 MHz, [δ, $d_6$-DMSO);] δ, *DMSO-$d_6$*); 1.20–1.30 (m, 1H), 1.45–1.66 (m, 7H), 1.83–1.86 (m, 2H), 3.78 (s, 3H), 7.40–7.45 (m, 1H), 7.60–7.66 (m, 1H), 7.69–7.72 (m, 2H). FAB MS; 366. ($M^+$+1). m.p.; 230–232° C.

EXAMPLE 32

1-{2-[6-Amino-9-methyl-8-(2-thienyl)-9H-2-purinyl]-1-ethynyl}-1-cyclohexanol Hydrochloride NMR (400 MHz, [δ, $d_6$-DMSO);] δ, *DMSO-$d_6$*); 1.42–1.70 (m, 10H), 3.88 (s, 3H), 7.26–7.29 (m, 1H), 7.80–7.83 (m, 2H). m.p.; 171–175° C.

EXAMPLE 33

2-(4-Cyclohexyl-1-butynyl)-8-(2-furyl)-9-methyl-9H-6-purinamine Hydrochloride

NMR (400 MHz, [δ, $d_6$-DMSO);] δ, *DMSO-$d_6$*); 0.82–0.96 (m, 2H), 1.08–1.24 (m, 3H), 1.30–1.50 (m, 3H), 1.58–1.76 (m, 5H), [2.48 (t, J=7.3 Hz, 2H), 3.88 (s, 3H), 6.78 (dd, J=1.8 Hz, 3.7 Hz, 1H), 7.25 (d, J=3.7, 1H),] *2.48* (*t, J=7.3 Hz, 2H*), *3.88* (*s, 3H*), *6.78* (*dd, J=1.8 Hz, 3.7 Hz, 1H*), *7.25* (*d, J=3.7, 1H*), 8.00 (m, 1H). m.p.; 165–169° C.

EXAMPLE 34

1-[6-Amino-8-(2-furyl)-9-methyl-9H-2-purinyl]-4-methyl-1-pentyn-3-ol Hydrochloride NMR (400 MHz, [δ, $d_6$-DMSO); 0.97 (t, J=6.8 Hz, 6H),] δ, *DMSO-$d_6$*); *0.97* (*t, J=6.8 Hz, 6H*), 1.78–1.83 (m, 1H), 3.88 (s, 3H), [4.22 (d, J=6.4 Hz, 1H),] *4.22* (*d, J=6.4 Hz, 1H*), 6.78–6.79 (m, 1H), 7.20–7.23 (m, 1H), 7.99 (s, 1H). FAB MS; 312 ($M^+$+1).

EXAMPLE 35

1-[2-(6-Amino-8-cyclohexyl-9-methyl-9H-2-purinyl)-1-ethynyl]-1-cyclohexanol Hydrochloride NMR (400 MHz, [δ, $d_6$-DMSO);] δ, *DMSO-$d_6$*); 1.20–1.30 (m, 2H), 1.35–1.77 (m, 12H), 1.78–1.86 (m, 4H), 1.93–2.00 (m, 2H), 3.07–3.17 (m, 1H), 3.73 (s, 3H). FAB MS; 354 ($M^+$+1).

EXAMPLE 36

2-(2-Cyclohexyl-1-ethynyl)-8-(2-furyl)-9-methyl-9H-6-purinamine Hydrochloride

NMR (400 MHz, [δ, $d_6$-DMSO);] δ, *DMSO-$d_6$*); 1.24–1.88 (m, 8H), 2.60–2.74 (m, 1H), 3.88 (s, 3H), 6.78 (br, 1H), *[7.25 (d, J=3.3, 1H),] *7.25* (*d, J=3.3, 1H*), 8.00 (br, 1H). m.p.; 155–160° C.

EXAMPLE 37

1-}2-[6-Amino-9-methyl-8-(2-pyridinyl)-9H-2-purinyl]-1-ethynyl}-1-cyclohexanol Dihydrochloride NMR (400 MHz, [δ, $d_6$-DMSO);] δ, *DMSO-$d_6$*); 1.22–1.33 (m, 1H), 1.46–1.71 (m, 7H), 1.84–1.94 (m, 2H), 4.13 (s, 3H), 7.58–7.61 (m, 1H), 8.05–8.10 (m, 1H), 8.26–8.28 (m, 1H), 8.77–8.79 (m, 1H). FAB MS; 349 ($M^+$+1).

EXAMPLE 38

1-{2-[6-Amino-8-(4-chlorophenyl)-9-methyl-9H-2-purinyl]-1-ethynyl}-1-cyclohexanol Hydrochloride NMR (400 MHz, [δ, $d_6$-DMSO);] δ, *DMSO-$d_6$*); 1.19–1.30 (m, 1H), 1.42–1.65 (m, 7H), 1.80–1.88 (m, 2H), 3.77 (s, 3H), [7.64 (d, J=8.0 Hz, 2H), 7.88 (d, J=8.0 Hz, 2H).] *7.64 (d, J=8.0 Hz, 2H), 7.88 (d, J=8.0 Hz, 2H).* FAB MS; 382 ($M^+$+1) FAB.

EXAMPLE 39

1-[6-Amino-8-(2-furyl)-9-methyl-9H-2-purinyl]-3-isopropyl-4-methyl-1-pentyn-3-ol Hydrochloride NMR (400 MHz, [δ, $d_6$-DMSO); 0.96 (d, J=7.0 Hz, 6H), 1.01 (d, J=7.0 Hz, 6H),] δ, *DMSO-$d_6$*); 0.96 *(d, J=7.0 Hz, 6H), 1.01 (d, J=7.0* Hz, 6H), 1.86–1.94 (m, 2H), 3.87 (s, 3H), 6.78–6.80 (m, 1H), 7.22–7.26 (m, 1H), 8.01 (s, 1H). FAB MS; 354 ($M^+$+1).

EXAMPLE 40

1-[2-(6-Amino-9-benzo[b]furan-2-yl-9-methyl-9H-2-purinyl)-1-ethynyl]-1-cyclohexanol Hydrochloride NMR (400 MHz, [δ, $d_6$-DMSO);] δ, *DMSO-$d_6$); 1.20–1.68 (m, 8H), 1.80–1.88 (m, 2H), 3.99 (s, 3H), 7.32–7.46 (m, 2H), 7.66–7.81 (m, 3H). FAB MS; 388 ($M^+$+1).*

EXAMPLE 41

8-(2-Furyl)-9-methyl-2-[3-morpholino-1-propynyl)-9H-purinamine

NMR (400 MHz, [δ,] δ, $CDCl_3$); [2.70 (t, J=5.0 Hz,4H), 3.78 (t, J=5.0 Hz,4H),] *2.70 (t, J=5.0 Hz,4H), 3.78 (t, J=5.0 Hz,4H),* 3.79 (s, 2H), 4.02 (s, 3H), 5.99 (br s, 2H), 6.62–6.65 (m, 1H), 7.10–7.13 (m, 1H), 7.65–7.68 (m, 1H). FAB MS; 339 ($M^+$+1).

EXAMPLE 42

1-{2-[6-Amino-8-(3-fluorophenyl-4-methoxyphenyl)-9-methyl-9H-2-purinyl]-1-ethynyl}-1-cyclohexanol Hydrochloride NMR (400 MHz, [δ, $d_6$-DMSO);] δ, *DMSO-$d_6$); 1.20–1.30 (m, 1H), 1.42–1.68 (m, 7H), 1.80–1.88 (m, 2H), 3.79 (s, 3H), 3.92 (m, 3H), 7.34–7.39 (m, 1H), 7.66–7.76 (m, 2H). FAB MS; 396 ($M^+$+1).*

EXAMPLE 43

2-(3-Amino-4-methyl-7-1-pentynyl)-8-(2-furyl)-9-methyl-9H-6-purinamine Dihydrochloride NMR (400 MHz; [δ, $d_6$-DMSO); 1.05 (t, J=7.0 Hz, 6H),] δ, *DMSO-$d_6$); 1.05 (t, J=7.0 Hz, 6H),* 2.12–2.20 (m, 1H), 3.88 (s, 3H), 4.25–4.30 (m, 1H), 6.78–6.80 (m, 1H), 7.22–7.24 (m, 1H), 8.00 (s, 1H), 8.72 (br s, 2H). FAB MS; 311 ($M^+$+1).

EXAMPLE 44

4-{2-[6-Amino-8-(3-fluorophenyl)-9-methyl-9H-2-purinyl]-1-ethynyl}-tetrahydro-2H-4-pyranol Hydrochloride NMR (400 MHz, [δ, $d_6$-DMSO);] δ, *DMSO-$d_6$); 1.66–1.75 (m, 2H), 1.83–1.92 (m, 2H), 3.54–3.59 (m, 2H), 3.74–3.79 (m, 2H), 3.79 (s, 3H), 7.39–7.43 (m, 1H), 7.60–7.72 (m, 3H). FAB MS; 368 ($M^+$+1).*

EXAMPLE 45

Ethyl 3-{6-Amino-2-[2-(1-hydroxycyclohexyl)-1-ethynyl]-9-methyl-9H-8-purinyl}benzoate Hydrochloride NMR (400 MHz, [δ, $d_6$-DMSO);] δ, *DMSO-$d_6$); 1.20–1.30 (m, 1H),* [1.33 (t, J=7.1 Hz, 3H),] *1.33 (t, J=7.1 Hz, 3H),* 1.44–1.68 (m, 7H), 1.82–1.89 (m, 2H), 3.82 (s, 3H), [4.35 (q, J=7.1 Hz, 2H), 7.74 (t, J=7.7 Hz, 1H), 8.12–8.17 (m, 2H), 8.44 (d, J=0.7 Hz, 1H).] *4.35 (q, J=7.1 Hz, 2H), 7.74 (t, J=7.7 Hz, 1H), 8.12–8.17 (m, 2H), 8.44 (d, J=0.7 Hz, 1H).* FAB MS; 420 ($M^+$+1).

EXAMPLE 46

2-(3,3-Diphenyl-1-butynyl)-8-(3-fluorophenyl)-9-methyl-9H-6-purinylamine Hydrochloride NMR (400 MHz, [δ, $d_6$-DMSO);] δ, *DMSO-$d_6$); 3.79 (s, 1H), 7.24–7.28 (m, 2H), 7.33–7.37 (m, 4H), 7.39–7.45 (m, 1H), 7.56–7.59 (m, 4H), 7.60–7.65 (m, 1H), 7.69–7.73 (m, 2H). FAB MS; 450 ($M^+$+1).*

EXAMPLE 47

Ethyl 2-{6-Amino-8-(3-fluorophenyl)-2-[2-(1-hydroxycyclohexyl)-1-ethynyl]-9H-9-purinyl}acetate NMR (400 MHz, [δ, $d_6$-DMSO);] δ, *DMSO-$d_6$); 1.17–1.37 (m, 1H),* [1.21 (t, J=7.1 Hz, 3H),] *1.21 (t, J=7.1 Hz, 3H),* 1.46–1.76 (m, 7H), 1.99–2.14 (m, 2H), 3.70 (br s, 2H), [4.19 (q, J=7.1 Hz, 2H),] *4.19 (q, J=7.1 Hz, 2H),* 4.99 (s, 2H), 6.43 (br s, 2H), 7.17–7.26 (m, 1H), 7.34–7.51 (m, 3H).

EXAMPLE 48

1-{2-[6-Amino-8-(3-fluorophenyl)-9-(2-methoxyethyl)-9H-9-2-purinyl]-1-ethynyl}-1-cyclohexanol Hydrochloride NMR (400 MHz, [δ, $d_6$-DMSO);] δ, *DMSO-$d_6$); 1.20–1.30 (m, 1H), 1.42–1.67 (m, 7H), 1.82–1.88 (m, 2H), 3.07 (s, 3H),* [3.62 (t, J=5.3 Hz, 2H), 4.40 (t, J=5.3 Hz, 2H),] *3.62 (t, J=5.3 Hz, 2H), 4.40 (t, J=5.3 Hz, 2H),* 7.40–7.46 (m, 1H), 7.59–7.65 (m, 1H), 7.68–7.74 (m, 2H). FAB M; 410 ($M^+$+1).

EXAMPLE 49

1-2-[6-Amino-8-(3-fluorophenyl)-9-(2-hydroxyethyl)-9H-2-purinyl]-1-ethynyl}-1-cyclohexanol Hydrochloride NMR (400 MHz, [δ, $d_6$-DMSO);] δ, *DMSO-$d_6$); 1.21–1.32 (m, 1H), 1.42–1.68 (m, 7H), 1.81–1.89 (m, 2H),* [3.73 (t, J=5.3 Hz, 2H), 4.28 (t, J=5.3 Hz, 2H),] *3.73 (t, J=5.3 Hz, 2H), 4.28 (t, J=5.3 Hz, 2H),* 7.40–7.45 (m, 1H), 7.59–7.65 (m, 1H), 7.73–7.79 (m, 2H). FAB MS; 396 ($M^+$+1).

EXAMPLE 50

3-(6-Amino-2-[2-(1-hydroxycyclohexyl)-1-ethynyl]-9-methyl-9H-8-purinyl}benzonitrile Hydrochloride NMR (400 MHz, [δ, $d_6$-DMSO);] δ, *DMSO-$d_6$); 1.20–1.30 (m, 1H), 1.40–1.70 (m, 7H), 1.80–1.84 (m, 2H), 3.80 (s, 3H),* [7.78 (t, J=7.8 Hz, 1H), 8.02 (d, J=7.8 Hz, 1H), 8.18 (d, J=7.8 Hz, 1H),] *7.78 (t, J=7.8 Hz, 1H), 8.02 (d, J=7.8 Hz, 1H), 8.18 (d, J=7.8 Hz, 1H),* 8.32 (s, 1H). FAB MS; 373 ($M^+$+1).

EXAMPLE 51

1-[2-[6-Amino-8-(3-chlorophenyl)-9-methyl-9H-2-purinyl]-1-ethynyl}-1-cyclohexanol Hydrochloride NMR (400 MHz, [δ, $d_6$-DMSO);] δ, *DMSO-$d_6$); 1.20–1.30 (m, 1H), 1.42–1.64 (m, 7H), 1.80–1.89 (m, 2H),*

3.79 (s, 3H), 7.54–7.60 (m, 2H), 7.82–7.85 (m, 1H), 7.92 (br, 1H). FAB MS; 382 ($M^+$+1). m.p.; 194–199° C.

EXAMPLE 52

1-{2-[6-Amino-9-methyl-8-[3-(trifluoromethyl) phenyl-9H-2-purinyl]-1-ethynyl}-1-cyclohexanol Hydrochloride NMR (400 MHz, [δ, $d_6$-DMSO);] δ, *DMSO-$d_6$);* 1.20–1.30 (m, 1H), 1.42–1.70 (m, 7H), 1.80–1.89 (m, 2H), 3.81 (s, 3H), [7.82 (t, J=11.0 Hz, 1H), 7.93 (d, J=11.0 Hz, 1H), 8.19 (d, J=11.0 Hz, 1H),] *7.82 (t, J=11.0 Hz, 1H), 7.93 (d, J=11.0 Hz, 1H), 8.19 (d, J=11.0 Hz, 1H),* 8.21 (s, 1H). FAB MS; 416 ($M^+$+1).

EXAMPLE 53

1-{2-[6-Amino-8-(3,5-difluorophenyl)-9-methyl-9H-2-purinyl]-1-ethynyl}-1-cyclohexanol Hydrochloride NMR (400 MHz, [δ, $d_6$-DMSO);] δ, *DMSO-$d_6$);* 1.18–1.30 (m, 1H), 1.42–1.68 (m, 7H), 1.81–1.90 (m, 2H), 3.82 (s, 3H), 7.49–7.54 (m, 1H), 7.58–7.64 (m, 2H). FAB MS; 384 ($M^+$+1).

EXAMPLE 54

1-{2-[6-Amino-9-methyl-8-(3-methylphenyl)-9H-2-purinylp9 -1-ethynyl}-1-cyclohexanol Hydrochloride NMR (400 MHz, [δ, $d_6$-DMSO);] δ, *DMSO-$d_6$);* 1.08–1.31 (m, 1H), 1.42–1.71 (m, 7H), 1.82–1.92 (m, 2H), 2.40 (s, 3H), 3.81 (s, 3H), [7.41 (d, J=7.6 Hz, 1H), 7.48 (t, J=7.6 Hz, 1H), 7.67 (d, J=7.6 Hz, 1H),] *7.41 (d, J=7.6 Hz, 1H), 7.48 (t, J=7.6 Hz, 1H), 7.67 (d, J=7.6 Hz, 1H),* 7.69 (s, 1H). FAB MS; 362 ($M^+$+1).

EXAMPLE 55

1-{2-[6-Amino-8-(3-fluorophenyl)-9-(3-methoxyphenyl)-9H-2-purinyl]-1-ethynyl}-1-cyclohexanol Hydrochloride NMR (400 MHz, [δ, $d_6$-DMSO);] δ, *DMSO-$d_6$);* 1.20–1.30 (m, 1H), 1.44–1.68 (m, 7H), 1.83–1.91 (m, 2H), 3.83 (s, 3H), 7.18–7.20 (m, 1H), 7.41–7.42 (m, 1H), 7.43–7.46 (m, 1H), 7.51–7.55 (m, 1H). FAB MS; 378 ($M^+$+1).

EXAMPLE 56

1-{2-[6-Amino-8-(4-fluorophenyl)-9-methyl-9H-2-purinyl]-1-ethynyl}-1-cyclophexanol Hydrochloride NMR (400 MHz, [δ, $d_6$-DMSO);] δ, *DMSO-$d_6$);* 1.20–1.30 (m, 1H), 1.43–1.68 (m, 7H), 1.81–1.89 (m, 2H), 3.79 (s, 3H), 7.42–7.47 (m, 2H), 7.90–7.96 (m, 2H). FAB MS; 366 ($M^+$+1).

EXAMPLE 57

1-{2-[6-Amino-8-(3-dimethylamino)phenyl]-9-methyl-9H-2-purinyl}-1-ethynyl}-1-cyclohexanol Hydrochloride NMR (400 MHz, [δ, $d_6$-DMSO);] δ, *DMSO-$d_6$);* 1.18–1.30 (m, 1H), 1.42–1.70 (m, 7H), 1.80–1.92 (m, 2H), 3.05 (s, 6H), 3.85 (s, 3H), 7.32–7.70 (m, 4H). FAB MS; 391 ($M^+$+1).

EXAMPLE 58

1-{2-Amino-9-cyclopentyl-8-(3-fluorophenyl)-9H-2-purinyl]-1-ethylnyl}-1-cyclohexanol Hydrochloride NMR (400 MHz, [δ, $d_6$-DMSO);] δ, *DMSO-$d_6$);* 1.20–1.30 (m, 1H), 1.40–1.64 (m, 9H), 1.80–1.84 (m, 2H), 1.90–2.04 (m, 4H), 2.26–2.38 (m, 2H), 4.60–4.74 (m, 1H), 7.40–7.50 (m, 3H), 7.58–7.64 (m, 1H). FAB MS; 420 ($M^+$+1). m.p.; 196–200° C.

EXAMPLE 59

1-{2-[6-Amino-8-(2-fluorophenyl)-9-methyl-9H-2-purinyl]-1-ethynyl}1-cyclohexanol Hydrochloride NMR (400 MHz, [δ, $d_6$-DMSO);] δ, *DMSO-$d_6$);* 1.20–1.32 (m, 1H), 1.42–1.66 (m, 7H), 1.80–1.86 (m, 2H), 3.58 (s, 3H), 7.39–7.48 (m, 2H), 7.63–7.72 (m, 2H). FAB MS; 366 ($M^+$+1). m.p.; 151–155° C.

EXAMPLE 60

8-(3-Fluorophenyl)-9-methyl-2-[2-(3-pyridinyl)-1-ethynyl]-9H-6-purinamine Hydrochloride NMR (400 MHz, [δ, $d_6$-DMSO);] δ, *DMSO-$d_6$);* 3.81 (s, 3H), 7.40–7.51 (m, 2H), 7.60–7.76 (m, 4H), [7.90 (dt, J=7.8] *7.90 (dt, J=7.8* and 1.6 Hz, 1H), 8.64–8.67 (m, 1H). FAB MS; 345 ($M^+$+1).

EXAMPLE 61

3-{2-[6-Amino-8-(3-fluorophenyl)-9-methyl-9H-2-purinyl]-1-ethynyl}phenyl Hydrochloride NMR (400 MHz, [δ, $d_6$-DMSO);] δ, *DMSO-$d_6$);* 3.13 (s, 1H), 3.81 (s, 3H), 6.85–6.89 (m, 1H), 6.93–6.96 (m, 1H), 7.00–7.05 (m, 1H), [7.25 (t, J=8.0 Hz, 1H),] *7.25 (t, J=8.0 Hz, 1H),* 7.39–7.46 (m, 1H), 7.59–7.80 (m, 3H). FAB MS; 360 ($M^+$+1).

EXAMPLE 62

1-[6-Amino-8-(3-fluorophenyl)-9-methyl-9H-2-purinyl]-4-methyl-1-pentyl-3-ol Hydrochloride NMR (400 MHz, [δ, $d_6$-DMSO); 0.97 (dd, J=6.8 Hz, 7.7 Hz, 6H),] δ, *DMSO-$d_6$); 0.97 (d, J=6.8 Hz, 7.7 Hz, 6H),* 1.78–1.86 (m, 1H), 3.80 (s, 3H), [4.24 (dd, J=6.1 Hz, 1H),] *4.24 (d, J=6.1 Hz, 1H),* 7.40–7.45 (m, 1H), 7.60–7.66 (m, 1H), 7.69–8.30 (m, 2H). FAB MS; 340 ($M^+$+1). m.p.; 170–173° C.

EXAMPLE 63

1-[6-Amino-8-(3-fluorophenyl)-9-methyl-9H-2-purinyl]1-pentyn-3-ol Hydrochloride

NMR (400 MHz, [δ, $d_6$-DMSO); 0.97 (t, J=7.5 Hz, 3H),] δ, *DMSO-$d_6$); 0.97 (t, J=7.5 Hz, 3H),* 1.62–1.70 (m, 1H), 3.80 (s, 3H), 7.40–7.45 (m, 1H), 7.60–7.66 (m, 1H), 7.69–7.76 (m, 2H). FAB MS; 326 ($M^+$+1).

EXAMPLE 64

4-[6-Amino-8-(3-fluorophenyl)-9-methyl-9H-2-purinyl]-2-methyl-3-butyn-2-ol Hydrochloride NMR (400 MHz, [δ, $d_6$-DMSO);] δ, *DMSO-$d_6$);* 1.47 (s, 6H), 3.81 (s, 3H), 7.40–7.47 (m, 1H), 7.60–7.67 (m, 1H), 7.69–7.74 (m, 2H). FAB MS; 326 ($M^+$+1). m.p.; 181–182° C.

EXAMPLE 65

1-{2-[6-Amino-8-(3-fluorophenyl-9H-2-purinyl]-1-ethynyl}-1-cyclohexanol Hydrochloride NMR (400 MHz, [δ, $d_6$-DMSO);] δ, *DMSO-$d_6$);* 1.20–1.30 (m, 1H), 1.40–1.70 (m, 7H), 1.82–1.94 (m, 2H), 5.70 (s, 1H), 7.42–7.50 (m, 1H), 7.60–7.70 (m, 1H), 8.00–8.14 (m,2H). FAB MS; 353 ($M^+$+1).

EXAMPLE 66

1-{2-[6-Amino-8-(3-fluorophenyl)-9-propyl-9H-2-purinyl]-1-ethynyl}-1-cyclohexanol Hydrochloride NMR (400 MHz, [δ, $d_6$-DMSO); 0.70 (t, J=7.3 Hz, 3H),] δ, *DMSO-$d_6$); 0.70 (t, J=7.3 Hz, 3H),* 1.20–1.31 (m, 1H), 1.42–1.68 (m, 9H), 1.81–1.88 (m, 2H), [4.22 (t, J=7.3 Hz, 3H),] *4.22 (t, J=7.3 Hz, 3H),* 7.41–7.47 (m, 1H), 7.61–7.67 (m, 3H). FAB MS; 394 ($M^+$+1).

EXAMPLE 67

1-{2-[6-Amino-8-(3-fluorophenyl)-9-isopropyl-9H-2-purinyl]-1-ethynyl}-1-cyclohexanol Hydrochloride NMR (400 MHz, [δ, $d_6$-DMSO);] δ, *DMSO-$d_6$);* 1.20–1.31 (m, 1H), 1.42–1.68 (m, 7H), [1.59 (d, J=6.8 Hz, 6H), 1.82–1.91 (m, 2H), 4.61 (sept, J=6.8 Hz, 1H),] *1.59 (d, J=6.8 Hz, 6H), 1.82–1.91 (m, 2H), 4.61 (sept, J=6.8 Hz, 1H),* 7.45–7.54 (m, 3H), 7.45–7.54 (m, 3H), 7.63–7.68 (m, 1H). FAB MS; 394 ($M^+$+1).

EXAMPLE 68

$N^1$-Ethyl-4-[6-amino-8-(3-fluorophenyl)-2-[2-(1-hydroxycyclohexyl)-1-ethynyl]-9H-9-purinyl] butaneamide Hydrochloride NMR (400 MHz, [δ, $d_6$-DMSO); 0.91 (t, J=7.2 Hz, 3H),] δ, *DMSO-$d_6$); 0.91 (t, J=7.2 Hz, 3H),* 1.20–1.32 (m, 7H), 1.78–1.87 (m, 4H), [1.93 (t, J=7.1 Hz, 2H), 2.94 (dq, J=5.5, 7.2 Hz, 2H), 4.25 (t, J=7.1 Hz, 2H),] *1.93 (t, J=7.1 Hz, 2H), 2.94 (dq, J=5.5,7.2 Hz, 2H), 4.25 (t, J=7.1 Hz, 2H),* 7.40–7.45 (m, 1H), 7.58–7.65 (m, 3H), [7.72 (t, J=5.5 Hz, 1H).] *7.72 (t, J=5.5 Hz, 1H).* FAB MS; 465 ($M^+$+1).

EXAMPLE 69

$N^1$-Ethyl-4-[6-amino-8-(3-fluorophenyl)-2-[2-(1-hydroxycyclohexyl)-1-ethynyl]-9H-9-purinyl] propaneamide Hydrochloride NMR (400 MHz, [δ, $d_6$-DMSO); 0.90 (t, J=7.2 Hz, 3H),] δ, *DMSO-$d_6$); 0.90 (t, J=7.2 Hz, 3H),* 1.18–1.33 (m, 1H), 1.42–1.68 (m, 7H), 1.80–1.88 (m, 2H), [2.55 (t, J=7.5 Hz, 2H), 2.93 (dq, J=5.5, 7.2 Hz, 2H), 4.43 (t, J=7.5 Hz, 2H),] *2.55 (t, J=7.5 Hz, 2H), 2.93 (dq, J=5.5,7.2 Hz, 2H), 4.43 (t, J=7.5 Hz, 2H),* 7.39–7.45 (m, 1H), 7.58–7.66 (m, 3H), [7.90 (t, J=5.5 Hz, 1H).] *7.90 (t, J=5.5 Hz, 1H).* FAB MS; 451 ($M^+$+1).

EXAMPLE 70

1-[6-Amino-8-(3-fluorophenyl)-9-methyl-9H-2-purionyl]-3-isopropyl-4-methyl-1-pentyn-3-ol Hydrochloride NMR (400 MHz, [δ, $d_6$-DMSO); 0.98 (d, J=6.8 Hz, 6H), 1.04 (d, J=6.8 Hz, 6H),] δ, *DMSO-$d_6$); 0.98 (d, J=6.8 Hz, 6H), 1.04 (d, J=6.8 Hz, 6H),* 1.87–1.97 (m, 2H), 3.83 (s, 3H), 7.41–7.48 (m, 1H), 7.62–7.70 (m, 1H), 7.71–7.77 (m, 2H). FAB MS; 382 ($M^+$+1).

EXAMPLE 71

$N^1$-Isopropyl-4-[6-amino-8-(3-fluorophenyl)-2-[2-1-hydroxycyclohexyl)-1-ethynyl]-9H-9-purinyl}butaneamide Hydrochloride NMR (400 MHz, [δ, $d_6$-DMSO); 0.94 (d, J=7.6 Hz, 6H),] δ, *DMSO-$d_6$); 0.94* (d, J=7.6 Hz, 6H), 1.20–1.32 (m, 1H), 1.41–1.68 (m, 7H), 1.78–1.88 (m, 4H), [1.92 (t, J=7.1 Hz, 2H), 3.64–3.74 (m, 1H), 4.25 (t, J=7.6 Hz, 2H),] *1.92 (t, J=7.1* Hz, 2H), *3.64–3.74 (m, 1H), 4.25 (t, J=7.6 Hz, 2H),* 7.40–7.46 (m, 1H), 7.58–7.65 (m, 3H). FAB MS; 479 ($M^+$+1).

EXAMPLE 72

$N^1$-Ethyl-2-{6-amino-8-(3-fluorophenyl-2-[2-(1-hydroxycyclohexyl)-1-ethynyl]-9H-9-purinyl}butaneamide Hydrochloride NMR (400 MHz, [δ, $d_6$-DMSO); 0.98 (d, J=7.2 Hz, 3H),] δ, *DMSO-$d_6$); 0.98 (t, J=7.2 Hz, 3H),* 1.18–1.30 (m, 1H), 1.40–1.68 (m, 7H), [1.65 (t, J=7.3 Hz, 3H), 1.78–1.88 (m, 2H), 3.08 (dq, J=5.3, 7.2 Hz, 2H), 5.08 (q, J=7.3 Hz, 1H),] *1.65 (t, J=7.3 Hz, 3H), 1.78–1.88 (m, 2H), 3.08 (dq, J=5.3, 7.2 Hz, 2H), 5.08 (q, J=7.3 Hz, 1H),* 7.39–7.48 (m, 3H), 7.58–7.63 (m, 1H), [8.05 (t, J=5.3 Hz, 1H).] *8.05 (t, J=5.3 Hz, 1H).* FAB MS; 451 ($M^+$+1).

EXAMPLE 73

1-[6-Amino-8-(3-fluorophenyl)-9-methyl-9H-2-purinyl]-3-ethyl-1-pentyn-3-ol Hydrochloride NMR (400 MHz, [δ, $d_6$-DMSO); 1.00 (t, J=7.2 Hz, 6H),] δ, *DMSO-$d_6$); 1.00 (t, J=7.2 Hz, 6H),* 1.61–1.71 (m, 4H), 3.81 (s, 3H), 7.40–7.44 (m,1H), 7.61–7.67 (m, 1H), 7.69–7.74 (m, 2H). FAB MS; 354 ($M^+$+1).

EXAMPLE 74

$N^1$-Ethyl-2-{6-amino-8-(3-fluorophenyl)-2-[2-(1-hydroxycyclohexyl)-1-ethynyl]-9H-9-purinyl]-2-phenylacetamide Hydrochloride NMR (400 MHz, [δ, $d_6$-DMSO); 1.00 (t, J=7.1 Hz, 3H),] δ, *DMSO-$d_6$); 1.00 (t, J=7.1 Hz, 3H),* 1.19–1.30 (m, 1H), 1.40–1.68 (m, 7H), 1.78–1.88 (m, 2H), 3.09–3.20 (m, 2H), 6.47 (s, 1H), 7.00–7.04 (m, 2H), 7.13–7.24 (m, 6H), 7.29–7.35 (m, 1H), [8.39 (t, J=5.4 Hz, 1H).] *8.39 (t, J=5.4 Hz, 1H).* FAB MS; 513 ($M^+$+1).

EXAMPLE 75

8-(3-Fluorophenyl)-2-(3-methoxy-3-methyl-1-butynyl)-9-methyl-9H-6-purinamine Hydrochloride NMR (400 MHz, [δ, $d_6$-DMSO);] δ, *DMSO-$d_6$);* 1.50 (s, 6H), 3.34 (s, 3H), 3.83 (s, 3H), 7.41–7.48 (m, 1H), 7.60–7.68 (m, 1H), 7.70–7.76 (m, 2H). FAB MS; 340 ($M^+$+1).

EXAMPLE 76

N-{3-[6-Amino-8-(3-fluorophenyl)-9-methyl-9H-2-purinyl]-1,1-dimethyl-2-propynyl}-N'-ethylurea Hydrochloride NMR (400 MHz, [δ, $d_6$-DMSO); 1.25 (t, J=7.0 Hz, 3H),] δ, *DMSO-$d_6$); 1.25 (t, J=7.0 Hz, 3H),* 1.68 (s, 6H), [3.46 (q, J=7.0 Hz, 2H),] *3.46 (q, J=7.0 Hz, 2H),* 3.98 (s, 3H), 6.32 (s, 1H), 7.45–7.52 (m, 1H), 7.64–7.83 (m, 2H). FAB MS; 396 ($M^+$+1).

EXAMPLE 77

1-{2-(6-Amino-8-(3-fluorophenyl)-9-isobutyl-9H-2-purinyl]-1-ethynyl}-1-cyclohexanol Hydrochloride NMR (400 MHz, [δ, $d_6$-DMSO); 0.63 (d, J=6.6 Hz, 6H),] δ, *DMSO-$d_6$); 0.63 (d, J=6.6 Hz, 6H),* 1.19–1.33 (m, 1H), 1.40–1.67 (m, 9H), 1.79–1.91 (m, 3H), [4.13 (t, J=7.5 Hz, 2H),] *4.13 (t, J=7.5 Hz, 2H),* 7.38–7.45 (m, 1H), 7.58–7.68 (m, 3H). FAB MS; 408 ($M^+$+1).

EXAMPLE 78

2-{6-Amino-8-(3-fluorophenyl)-2-[2-(1-hydroxycyclohexyl)-1ethynyl]-9H-9-purinyl}ethyloxy N-Ethyl-carbamate Hydrochloride NMR (400 MHz, [δ, $d_6$-DMSO); 0.86 (t, J=7.2 Hz, 3H),] δ, *DMSO-$d_6$); 0.86 (t, J=7.2 Hz, 3H),* 1.19–1.32 (m, 1H), 1.41–1.70 (m, 7H), 1.80–1.92 (m, 2H), [2.80 (dq, J=5.5, 7.2 Hz, 2H), 4.19 (t, J=5.7 Hz, 2H). 4.44–4.52 (m, 2H), 6.96 (t, J=5.5 Hz, 1H),] *2.80 (dq, J=5.5,7.2 Hz, 2H),* 4.19 *(t, J=5.7 Hz, 2H), 4.44–4.52 (m, 2H), 6.96 (t, J=5.5* Hz, 1H), 7.40–7.48 (m, 1H), 7.58–7.66 (m, 3H). FAB MS; 467 ($M^+$+1).

EXAMPLE 79

1-{2-[6-Amiono-8-(3-fluorophenyl)-9-phenethyl-9H-2-purinyl]-1-ethynyl}-1-cyclohexanol Hydrochloride NMR (400 MHz, [δ, $d_6$-DMSO);] δ, *DMSO-$d_6$);* 1.25–1.72 (m, 8H), 1.87–1.90 (m, 2H), [2.97 (t, J=6.0 Hz, 2H), 4.52 (t, J=6.0 Hz, 2H),] *2.97 (t, J=6.0 Hz, 2H), 4.52 (t, J=6.0 Hz, 2H),* 6.81–6.85 (m, 2H), 7.10–7.21 (m, 4H). FAB MS; 456 ($M^+$+1).

EXAMPLE 80

$N^1$-Ethyl-3-{6-amino-8-(3-fluorophenyl)-2-[2-(1-hydroxycyclohexyl)-1-ethynyl}-9H-9-purinyl]-1-propanesulfonamide Hydrochloride NMR (400 MHz, [δ, $d_6$-DMSO);] δ, *DMSO-$d_6$);* 0.93–1.00 (m, 3H), 1.19–1.32 (m, 1H), 1.40–1.68 (m, 7H), 1.77–1.90 (m, 2H), 1.95–2.14 (m, 2H), 2.75–2.87 (m, 2H), 2.90–2.98 (m, 2H), 4.35–4.42 (m, 2H), 6.94–7.02 (m, 1H), 7.40–7.48 (m, 1H), 7.58–7.78 (m, 3H). FAB MS; 501 ($M^+$+1).

EXAMPLE 81

1-{2-[6-Amino-8-(3-fluorophenyl)-9-(2-hydroxypropyl)-9H-2-purinyl]-1-ethynyl}-1-cyclohexanol Hydrochloride NMR (400 MHz, [δ, $d_6$-DMSO);] δ, *DMSO-$d_6$);* 1.00–1.10 (m, 3H), 1.18–1.33 (m, 1H), 1.40–1.70 (m, 7H), 1.78–1.90 (m, 2H), 4.00–4.12 (m, 2H), 4.12–4.21 (m, 1H), 7.36–7.43 (m,1H), 7.56–7.63 (m, 1H), 7.71–7.80 (m, 2H). FAB MS; 410 ($M^+$+1).

EXAMPLE 82

1-{2-[6-Amino-9-(2-butynyl)-8-(3-fluorophenyl)-9H-2-purinyl]-1-ethynyl}-1-cyclohexanol Hydrochloride NMR (400 MHz, [δ, $d_6$-DMSO);] δ, *DMSO-$d_6$);* 1.20–1.68 (m, 8H), [1.75 (t, J=2.0 Hz, 3H), 1.80–1.88 (m, 2H), 5.00 (q, J=2.0 Hz, 2H),] *1.75 (t, J=2.0 Hz, 3H), 1.80–1.88 (m, 2H), 5.00 (q, J=2.0 Hz, 2H),* 7.40–7.45 (m, 1H), 7.62–7.78 (m, 3H). FAB MS; 404 ($M^+$+1).

EXAMPLE 83

1-{2-[6-Amino-8-(3-fluorophenyl)-9-(3-morpholinopropyl)-9H-2-purinyl]-1-ethynyl}-1-cyclohexanol Dihydrochloride NMR (400 MHz, [δ, $d_6$-DMSO);] δ, *DMSO-$d_6$);* 1.19–1.29 (m, 1H), 1.40–1.64 (m, 7H), 1.79–1.88 (m, 2H), 2.04–2.16 (m, 2H), 2.84–3.08 (m, 4H), 3.23–3.34 (m, 2H), 3.65–3.78 (m, 2H), 3.82–3.92 (m, 2H), 4.28–4.36 (m, 2H), 7.42–7.48 (m, 1H), 7.60–7.68 (m, 3H). FAB MS; 479 ($M^+$+1).

EXAMPLE 84

1-{3-{6-Amino-8-(3-fluorophenyl)-2-[2-(1-hydroxycyclohexyl)-1-ethynyl-9H-9-purinyl}propyl}2-pyrrolidinone Hydrochloride NMR (400 MHz, [δ, $d_6$-DMSO);] δ, *DMSO-$d_6$);* 1.22–1.34 (m, 1H), 1.44–1.72 (m, 7H), 1.78–1.93 (m, 6H), [2.14 (t, J=8.0 Hz, 2H), 3.08 (t, J=7.0 Hz, 2H), 3.19 ) t, J=7.0 Hz, 2H), 4.22 (t, J=7.0 Hz, 2H),] *2.14 (t, J=8.0 Hz, 2H), 3.08 (t, J=7.0 Hz, 2H), 3.19 (t, J=7.0 Hz, 2H), 4.22 (t, J=7.0 Hz, 2H),* 7.44–7.50 (m, 1H), 7.59–7.70 (m, 3H). FAB MS; 477 ($M^+$+1).

EXAMPLE 85

1-{2-[6-Amino-8-(3-fluorophenyl)-9-methyl-9H-2-purinyl]-1-ethynyl}-cyclopentanol Hydrochloride NMR (400 MHz, [δ, $d_6$-DMSO);] δ, *DMSO-$d_6$);* 1.44–1.66 (m, 8H), 1.76–1.84 (m, 2H), 1.94–2.02 (m, 2H), 3.80 (s, 3H), 7.38–7.44 (m, 1H), 7.58–7.66 (m, 1H), 7.64–7.44 (m, 2H). FAB MS; 380 ($M^+$+1).

EXAMPLE 86

$N^1$-Cyclopropyl-4-[6-amino-8-(3-fluorophenyl)-2-[2-(1-hydroxycyclohexyl)-1-ethynyl]-9H-9-purinyl] butaneamide Hydrochloride NMR (400 MHz, [δ, $d_6$-DMSO);] δ, *DMSO-$d_6$);* 0.25–0.30 (m, 2H), 0.50–0.56 (m, 2H), 1.20–1.34 (m, 1H), 1.40–1.70 (m, 7H), 1.78–1.94 (m, 6H), 2.43–2.54 (m, 1H), [4.26 (t, J=7.0 Hz, 2H),] *4.26 (t, J=7.0 Hz, 2H),* 7.41–7.47 (m, 1H), 7.60–7.68 (m, 3H), [7.81 (d, J=4.4 Hz, 1H).] *7.81 (d, J=4.4 Hz, 1H).* FAB MS; 477 ($M^+$+1).

EXAMPLE 87

1-{2-[6-Amino-8-(3-fluorophenyl)-9-methyl-9H-2-purinyl]-ethynyl}-4-methyl-1-cyclohexanol Hydrochloride NMR (400 MHz, [δ, $d_6$-DMSO); 0.89 (d, J=6.0 Hz, 3H),] δ, *DMSO-$d_6$); 0.89 (d, J=6.0 Hz, 3H),* 1.25–1.53 (m, 5H), 1.63–1.74 (m, 2H), 1.89–1.98 (m, 2H), 3.82 (s, 3H), 7.42–7.48 (m, 1H), 5.62–7.80 (m, 3H). FAB MS; 380 ($M^+$+1).

EXAMPLE 88

1-{9-[6-Amino-8-(3-fluorophenyl)-9-methyl-9H-2-purinyl]-1-ethynyl]-1,4-cyclohexanediol Hydrochloride NMR (400 MHz, [δ, $d_6$-DMSO);] δ, *DMSO-$d_6$);* 1.58–1.60 (m, 4H), 1.73–1.79 (m, 2H), 1.93–1.99 (m, 2H), 3.14 (s, 1H), 3.47–3.53 (m, 1H), 3.83 (s, 3H), 7.41–7.47 (m, 1H), 7.62–7.73 (m, 3H). FAB MS; 382 ($M^+$+1).

EXAMPLE 89

1-{2-[6-Amino-8-(3-fluorophenyl)-9-methyl-9H-2-purinyl]-1-ethynyl}-1-cyclobutanol Hydrochloride NMR (400 MHz, [δ, $d_6$-DMSO);] δ, *DMSO-$d_6$);* 1.74–1.85 (m, 2H), 2.16–2.27 (m, 2H), 2.34–2.43 (m, 2H), 3.81 (s, 3H), 7.39–7.47 (m, 1H), 7.56–7.77 (m, 3H). ESI MS; 338.0 ($M^+$+1). m.p.; 198–199° C.

EXAMPLE 90

1-{2-[6-Amino-8-(3,5-difluorophenyl)-9-methyl-9H-2-purinyl]-1-ethynyl}-1-cyclopentanol Hydrochloride NMR (400 MHz, [δ, $d_6$-DMSO);] δ, *DMSO-$d_6$);* 1.64–1.79 (m, 4H), 1.84–1.97 (m, 4H), 3.82 (s, 3H), 7.48–7.54 (m, 1H), 7.57–7.64 (m, 2H). FAB MS; 370 ($M^+$+1). m.p.; 255–258° C.

EXAMPLE 91

1-{2-{6-Amino-9-methyl-8-[3-(trifluoromethyl) phenyl]-9H-2-purinyl}-1-ethynyl}-1-cyclopentanol Hydrochloride NMR (400 MHz, [δ, $d_6$-DMSO);] δ, *DMSO-$d_6$);* 1.62–1.78 (m, 4H), 1.82–1.96 (m, 4H), 3.81 (s, 3H), 7.79–7.85 (m, 1H), 7.91–7.95 (m, 1H), 8.17–8.21 (m, 2H). FAB MS; 402 ($M^+$+1).

EXAMPLE 92

1-{2-[6-Amino-8-(3-fluorophenyl-9-(2-hydroxyethyl)-9H-2-purinyl]-1-ethynyl}-1-cyclopentanol Hydrochloride NMR (400 MHz, [δ, $d_6$-DMSO);] δ, *DMSO-$d_6$);* 1.72–1.80 (m, 4H), 1.84–1.98 (m, 4H), [3.73 (t, J=5.6 Hz, 2H), 4.27 (t, J=5.6 Hz, 2H),] *3.73 (t, J=5.6 Hz, 2H), 4.27 (t, J=5.6 Hz, 2H),* 7.38–7.45 (m, 1H), 7.58–7.64 (m, 1H), 7.71–7.80 (m, 2H). FAB MS; 382 ($M^+$+1).

EXAMPLE 93

1-{2-[6-Amino-8-(2,5-difluorophenyl)-9-methyl-9H-2-purinyl]-1-ethynyl}-1-cyclopentanol Hydrochloride NMR (400 MHz, [δ, $d_6$-DMSO);] δ, *DMSO-$d_6$);* 1.56–1.77 (m, 4H), 1.77–1.95 (m, 4H), 3.60 (s, 3H), 7.45–7.63 (m, 3H). ESI MS; 370 ($M^+$+1).

EXAMPLE 94

1-{2[6-Amino-8-(2,3-difluorophenyl)-9-methyl-9H-2-purinyl}-1-ethynyl}-1-cyclopentanol Hydrochloride NMR (400 MHz, [δ, $d_6$-DMSO);] δ, *DMSO-$d_6$);* 1.64–1.79 (m, 4H), 1.83–1.96 (m, 4H), 3.63 (s, 3H), 7.40–7.45 (m, 1H), 7.52–7.56 (m, 1H), 7.66–7.74 (m, 1H). FAB MS; 371 ($M^+$+1).

EXAMPLE 95

3-[6-Amino-2-[2-(1-hydroxycyclopenyl)-1-ethynyl]-9-methyl-9H-8-purinyl]phenol Hydrochloride NMR (400 MHz, [δ, $d_6$-DMSO);] δ, *DMSO-$d_6$);* 1.63–1.79 (m, 4H), 1.83–1.97 (m, 4H), 3.76 (s, 3H), 6.94–6.98 (m, 1H), 7.21–7.27 (m, 2H), [7.37 (t, J=7.9 Hz, 1H).] *7.37 (t, J=7.9 Hz, 1H).* FAB MS; 350 ($M^+$+1).

EXAMPLE 96

1-{2-[6-Dimethylamino-8-(3-fluorophenyl)-9-methyl-9H-2-purinyl]-1-ethynyl}-1-cyclopentanol NMR (400 MHz, [δ,] δ, $CDCl_3$); 1.76–1.97 (m, 4H), 2.03–2.13 (m, 2H), 2.13–2.22 (m, 2H), 2.22 (s, 1H), 3.58 (br s, 6H), 3.88 (s, 3H), 7.17–7.23 (m, 1H), 7.46–7.57 (m, 3H).

EXAMPLE 97

1-{2-[8-(3-Fluorophenyl)-9-methyl-6-methylamino-9H-2-purinyl]-1-ethynyl}-1-cyclopentanol NMR (400 MHz, [δ,] δ, $CDCl_3$); 1.72–1.96 (m, 4H), 2.02–2.12 (m, 2H), 2.14–2.22 (m, 2H), 2.26 (s, 1H), 3.25 (br s, 3H), 3.89 (s, 3H), 5.87 (br s, 1H), 7.20–7.25 (m, 1H), 7.44–7.56 (m, 3H).

EXAMPLE 98

1-{2-[6-Benzylamino-8-(3-fluorophenyl)-9-methyl-9H-purinyl]-1-ethynyl}-1-cyclopentanol Hydrochloride NMR (400 MHz, [δ, $d_6$-DMSO);] δ, *DMSO-$d_6$);* 1.64–1.80 (m, 4H), 1.86–1.97 (m, 4H), 3.81 (s, 3H), 4.72 (br s, 2H), 7.20–7.25 (m, 1H), 7.28–7.37 (m, 4H), 7.39–7.45 (m, 1H), 7.60–7.66 (m, 1H), 7.68–7.75 (m, 2H), 8.53 (br s, 1H).

EXAMPLE 99

1-{2-[8-(3-Fluorophenyl)-6-[(2-hydroxyethyl) amino]-9-methyl-9H-2-purinyl]-1-ethynyl}-1-cyclopentanol Hydrochloride NMR (400 MHz, [δ, $d_6$-DMSO);] δ, *DMSO-$d_6$);* 1.65–1.82 (m, 4H), 1.84–2.02 (m, 4H), 3.59 (br s,4H), 3.82 (s, 3H), 7.41–7.47 (m, 1H), 7.61–7.67 (m, 1H), 7.70–7.76 (m, 2H), 7.98 (br s, 1H).

EXAMPLE 100

1-{2-[6-Cyclopentylamino-8-(3-fluorophenyl)-9-methyl-9H-2-purinyl]-1-ethynyl}-1-cyclopentanol NMR (400 MHz, [δ, $d_6$-DMSO);] δ, *DMSO-$d_6$);* 1.50–1.64 (m, 4H), 1.65–1.81 (m, 6H), 1.82–2.00 (m, 6H), 3.80 (s, 3H), 4.55 (br s, 1H), 7.40–7.46 (m, 1H), 7.61–7.67 (m, 1H), 7.70–7.75 (m, 2H), 8.06 (br s, 1H).

EXAMPLE 101

3-{6-Amino-8-(3-fluorophenyl)-2-[2-(1-hydroxycyclopentyl)-1-ethynyl]-9H-9-purinyl}-1,2-propanediol Hydrochloride NMR (400 MHz, [δ, $d_6$-DMSO);] δ, *DMSO-$d_6$);* 1.60–1.80 (m, 4H), 1.82–1.98 (m, 4H), 3.30–3.40 (m, 2H), 3.80–4.00 (m, 1H), [4.13 (dd, J=9.6,14.5 Hz, 1H), 4.32 (dd, J=3.5,14.5 Hz, 1H).] *4.13 (dd, J=9.6,14.5 Hz, 1H), 4.32 (dd, J=3.5,14.5 Hz, 1H),* 7.37–7.44 (m, 1H), 7.56–7.64 (m, 1H), 7.74–7.86 (m, 2H). FAB MS; 412 ($M^+$+1).

EXAMPLE 102

4-{2-[6-Amino-8-(3-fluorophenyl)-9-methyl-9H-2-purinyl]-1-ethynyl}-1-methyl-4-piperidinol Dihydrochloride NMR (400 MHz, [δ, $d_6$-DMSO);] δ, *DMSO-$d_6$);* 2.04–2.30 (m, 4H), 2.72 and [2.81 (d×2,J=6.0 Hz, 3H).] *2.81*

(*d×2,J=6.0 Hz, 3H*), 3.05 . 3.49 (m, 4H), 3.80 and 3.82 (s×2,3H), 7.39–7.47 (m, 1H), 7.59–7.74 (m, 3H). FAB MS; 381 ($M^+$+1).

EXAMPLE 103

1-{4-[2-[6-Amino-8-(3-fluorophenyl)-9-methyl-9H-2-purinyl]-1-ethynyl]4-hydroxypiperidino}-1-ethanone Hydrochloride NMR (400 MHz, [δ, $d_6$-DMSO);] δ, *DMSO-$d_6$);* 1.50 and 1.93 (m, 4H), 1.97–2.00 (s×2,3H), 3.14 and 3.79 (s×2, 3H), 3.25–3.69 (m, 4H), 7.39–7.45 (m, 1H), 7.59–7.72 (m, 3H). FAB MS; 409 ($M^+$+1).

EXAMPLE 104

4-{2-[6-Amino-8-(3-fluorophenyl)-9-methyl-9H-2-purinyl]-1-ethynyl}-4-piperidinol Dihydrochloride NMR (400 MHz, [δ, $d_6$-DMSO);] δ, *DMSO-$d_6$);* 1.95–2.18 (m, 4H), 3.02–3.20 (m, 4H), 3.80 (s, 3H), 7.38–7.46 (m, 1H), 7.58–7.76 (m, 3H). FAB MS; 449 ($M^+$+1).

EXAMPLE 105

2-{6-Amino-2-[2-(1-hydroxycyclopentyl)-1-ethynyl]-9-methyl-9H-8-purinyl}-6-fluorophenol Hydrochloride NMR (400 MHz, [δ, $d_6$-DMSO);] δ, *DMSO-$d_6$);* 1.60–1.80 (m, 4H), 1.80–1.95 (m, 4H), 3.66–3.73 (m, 3H), 6.94–7.03 (m, 1H), 7.35–7.47 (m, 2H). FAB MS; 368 ($M^+$+1).

EXAMPLE 106

3-[6-Amino-8-(3-fluorophenyl)-9-methyl-9H-2-purinyl]-1-phenyl-2-propyn-1-ol

NMR (400 MHz, [δ, $d_6$-DMSO);] δ, *DMSO-$d_6$);* 3.77 (s, 3H), [5.60 (d, J=6.0 Hz, 1H), 6.26 (d, J=6.0 Hz, 1H),] *5.60 (d, J=6.0 Hz, 1H), 6.26 (d, J=6.0 Hz, 1H),* 7.29–7.33 (m, 1H), 7.36–7.43 (m, 3H), 7.47 (br s, 2H), 7.50–7.53 (m, 2H), 7.58–7.64 (m, 1H), 7.66–7.71 (m, 2H). FAB MS; 374 ($M^+$+1).

EXAMPLE 107

1-{2-[6-Amino-8-(3-fluoro-2-methylphenyl)-9-methyl-9H-2-purinyl]1-ethynyl}-1-cyclopentanol Hydrochloride NMR (400 MHz, [δ, $d_6$-DMSO);] δ, *DMSO-$d_6$);* 1.62–1.79 (m, 4H), 1.83–1.96 (m, 4H), [2.13 (d, J=2.0 Hz, 3H),] *2.13 (d, J=2.0 Hz, 3H),* 3.50 (s, 3H), 7.33–7.42 (m, 3H). FAB MS; 366 ($M^+$+1).

EXAMPLE 108

1-{2-[6-Amino-9-methyl-8-(1,3-thiazol-2-yl)-9H-2-purinyl]-1-ethynyl}-cyclopentanol Hydrochloride NMR (400 MHz, [δ, $d_6$-DMSO);] δ, *DMSO-$d_6$);* 1.61–1.78 (m, 4H), 1.81–1.97 (m, 4H), 4.09 (s, 3H), [7.99 (d, J=3.2 Hz, 1H), 8.11 (d, J=3.2 Hz, 1H).] *7.99 (d, J=3.2 Hz, 1H), 8.11 (d, J=3.2 Hz, 1H).* FAB MS; 341 ($M^+$+1).

EXAMPLE 109

$N^1$-Ethyl-(1R,3R)-3-{6-amino-8-(3-fluorophenyl)-2-[2-(1-hydroxycyclopentyl)-1-ethynyl]9H-9-purinyl}cyclopentanone-1-carboxamide Hydrochloride NMR (400 MHz, [δ, $d_6$-DMSO); 1.01 (t, J=7.2 Hz, 3H),] δ, *DMSO-$d_6$); 1.01 (t, J=7.2 Hz, 3H),* 1.64–2.22 (m, 12H), 2.44–2.68 (m, 2H), [3.08 (dq, J=2.7, 7.2 Hz, 2H),1Θ *3.08 (dq, J=2.6, 7.2 Hz, 2H),* 4.60–4.71 (m, 1H), 7.43–7.49 (m, 1H), 7.50–7.55 (m, 2H), 7.61–7.68 (m, 1H), [7.83 (t, J=2.6 Hz, 1H).] *7.83 (t, J=2.6 Hz, 1H).*

EXAMPLE 110

1-{2-[6-Amino-8-(3,5-difluorophenyl)-9-methyl-9H-2-purionyl]-1-ethynyl}-1-cyclobutanol Hydrochloride NMR (400 MHz, [δ, $d_6$-DMSO);] δ, *DMSO-$d_6$);* 1.76–1.86 (m, 2H), 2.20–2.32 (m, 2H), 2.36–2.46 (m, 2H), 3.85 (s, 3H), 7.46–7.55 (m, 1H), 7.56–7.67 (m, 2H). FAB MS; 356 ($M^+$+1).

EXAMPLE 111

1-{2-[-6-Amino-9-cyclopropyl-8-(3-fluorophenyl-9H-2-purinyl]-1-ethynyl}-1-cyclopentanol Hydrochloride NMR (400 MHz, [δ, $d_6$-DMSO);] δ, *DMSO-$d_6$);* 0.67–0.72 (m, 2H), 1.01–1.07 (m, 2H), 1.62–1.80 (m, 4H), 1.84–1.97 (m, 4H), 3.65–3.73 (m, 1H), 7.36–7.42 (m, 1H), 7.75–7.81 (m, 2H). FAB MS; 378 ($M^+$+1).

EXAMPLE 112

8-(3-Fluorophenyl)-9-methyl-2-(3-phenyl-1-propynyl)-9H-6-purinamine Hydrochloride NMR (400 MHz, [δ, $d_6$-DMSO);] δ, *DMSO-$d_6$);* 3.79 (s, 3H), 3.91 (s, 2H), 7.24–7.29 (m, 1H), 7.34–7.44 (m, 5H), 7.59–7.65 (m, 1H), 7.67–7.72 (m, 2H). FAB MS; 358 ($M^+$+1).

EXAMPLE 113

1-{2-[8-(3,5-Difluorophenyl)-9-methyl-6-(phenethylamino)-9H-2-purinyl]-1-ethynyl}-1-cyclopentanol Hydrochloride NMR (400 MHz, [δ, $d_6$-DMSO);] δ, *DMSO-$d_6$);* 1.60–1.78 (m, 4H), 1.78–1.98 (m, 4H), [2.93 (t, J=7.2 Hz, 2H),] *2.93 (t, J=7.2 Hz, 2H),* 3.60–3.75 (m, 2H), 3.80 (s, 3H), 7.14–7.21 (m, 1H), 7.22–7.32 (m, 4H), 7.44–7.52 (m, 1H), 7.54–7.64 (m, 2H), 8.05–8.12 (m, 1H). FAB MS; 474 ($M^+$+1).

EXAMPLE 114

1-{2-[8-(3,5-Difluorophenyl)-9-methyl-6-methylamino-9H-2-purinyl]-1-ethynyl}-1-cyclopentanol NMR (400 MHz, [δ,] δ, $CDCl_3$); 1.75–1.94 (m 4H), 2.03–2.12 (m, 2H), 2.12–2.22 (m, 2H), 3.25 (br s, 3H), 3.90 (s, 3H), 5.82 (br s, 1H), 6.95–7.00 (m, 1H), 7.29–7.36 (m, 2H).

EXAMPLE 115

1-{2-[6-Ethylamino-8-(3-fluorophenyl)-9-methyl-9H-2-purinyl]-1-ethynyl}-1-cyclopentanol NMR (400 MHz, [δ, $d_6$-DMSO); 1.19 (d, J=7.2 Hz, 3H),] δ, *DMSO-$d_6$); 1.19 (t, J=7.2 Hz, 3H),* 1.65–1.81 (m, 4H), 1.84–1.98 (m, 4H), 3.50 (br s, 2H), 3.80 (s, 3H), 5.44 (s, 1H), 7.38–7.45 (m, 1H), 7.59–7.66 (m, 1H), 7.67–7.73 (m, 2H), 7.95 (br s, 1H). FAB MS; 380 ($M^+$+1).

EXAMPLE 116

1-{2-[8-(3-Fluorophenyl)-9-methyl-6-propylamino-9H-2-purinyl]-1-ethynyl}-1-cyclopentanol NMR (400 MHz, [δ, $d_6$-DMSO); 0.91 (t, J=7.2 Hz, 3H), 1.62 (sex, J=7.2 Hz, 2H),] δ, *DMSO-$d_6$); 0.91 (t, J=7.2 Hz, 3H), 1.62 (sex, J=7.2 Hz, 2H),* 1.66–1.81 (m, 4H), 1.84–2.00 (m, 4H), 3.43 (br s, 2H), 3.80 (s, 3H), 5.44 (s, 1H), 7.38–7.45 (m, 1H), 7.59–7.67 (m, 1H), 7.68–7.74 (m, 2H), 7.91–7.98 (m, 1H). FAB MS; 394 ($M^+$+1).

EXAMPLE 117

1-{2-[8-(3-Fluorophenyl)-6-isobutylamino-9-methyl-9H-2-purinyl]-1-ethynyl}-1-cyclopentanol NMR (400 MHz, [δ,] δ, $CDCl_3$); [1.02 (d, J=6.8 Hz, 6H),] *1.02 (d, J=6.8 Hz, 6H),* 1.68–1.92 (m, 4H), [1.97 (sept, J=6.8 Hz, 6H),] *1.97 (sept, J=6.8 Hz, 6H),* 2.02–2.22 (m, 4H), 3.51 (br s, 2H), 3.88 (s, 3H), 5.89 (br s, 1H), 7.18–7.25 (m, 1H), 7.45–7.57 (m, 1H), 7.45–7.57 (m, 3H). FAB MS; 408 ($M^+$+1).

EXAMPLE 118

1-[2-(6-Amino-9-methyl-8-phenyl-9H-2-purinyl)-1-ethynyl]-1-cyclopentanol Hydrochloride NMR (400 MHz, [δ, $d_6$-DMSO);] δ, *DMSO-$d_6$);* 1.66–1.83 (m, 4H), 1.87–2.00 (m, 4H), 3.83 (s, 3H), 7.59–7.65 (m, 3H), 7.86–7.92 (m, 2H). FAB MS; 334 ($M^+$+1).

EXAMPLE 119

3-[6-Amino)-8-(3-fluorophenyl)-9-methyl-9H-2-purinyl]-2-propyn-1-ol Hydrochloride NMR (400 MHz, [δ, $d_6$-DMSO);] δ, *DMSO-$d_6$);* 3.79 (s, 3H), 4.30 (s, 2H), 7.38–7.44 (m, 1H), 7.59–7.65 (m, 1H), 7.66–7.72 (m, 2H).

EXAMPLE 120

1-{2-[6- Amino-8-(3-fluorophenyl)-9-methyl-9H-2-purinyl}-1-ethynyl]-2-methoxy-1-cyclohexanol NMR (400 MHz, [δ, $d_6$-DMSO);] δ, *DMSO-$d_6$);* 1.13–2.00 (m, 8H), [3.07 (d, J=9.6,4.0 Hz, 1H),] *3.07* (d, J=9.6,4.0 Hz, 1H), 3.39 (s, 3H), 3.80 (s, 3H), 5.69 (s, 1H), 7.39–7.45 (m, 1H), 7.48 (br s, 2H), 7.60–7.75 (m, 3H). ESI MS; 396 ($M^+$+1). m.p.; 281–283° C.

EXAMPLE 121

1-{2-[6-Amino-8-(3-fluorophenyl)-9-methyl-9H-2-purinyl]-1-ethynyl}-2-methoxy-1-cyclohexanol NMR (400 MHz, [δ, $d_6$-DMSO);] δ, *DMSO-$d_6$);* 1.12–1.92 (m, 8H), 3.20–3.25 (m, 1H), 3.40 (s, 3H), 3.80 (s, 3H), 5.33 (s, 1H), 7.38–7.45 (m, 1H), 7.48 (br s, 2H), 7.60–7.74 (m, 3H). ESI MS; 396 ($M^+$+1). m.p.; 195–197° C.

EXAMPLE 122

1-{2-[6-Amino-8-(3-fluorophenyl)-9-methyl-9H-2-purinyl]-1-ethynyl}-2-cyclopenten-1-ol NMR (400 MHz, [δ, $d_6$-DMSO);] δ, *DMSO-$d_6$);* 2.00–2.12 (m, 1H), 2.30–2.38 (m, 3H), 3.79 (s, 3H), 3.80 (s, 3H), 5.78 (s, 1H), 5.80–5.84 (m, 1H), 5.94–5.98 (m, 1H), 7.39–7.46 (m, 1H), 7.47 (br s, 2H), 7.59–7.74 (m, 3H). ESI MS; 350 ($M^+$+1). m.p.; 191–193° C.

EXAMPLE 123

1-{2-[6-Amino-8-(2,5-difluorophenyl)-9-methyl-9H-2-purinyl]-1-ethynyl}-1-cyclobutanol Hydrochloride NMR (400 MHz, [δ, $d_6$-DMSO);] δ, *DMSO-$d_6$);* 1.74–1.88 (m, 2H), 2.18–2.30 (m, 2H), 2.36–2.45 (m, 2H), 3.65 (m, 3H), 7.53–7.59 (m, 2H), 7.60–7.65 (m, 1H). FAB MS; 356 ($M^+$+1). m.p.; 149–152° C.

EXAMPLE 124

1-[6-Amino-8-(3,5-difluorophenyl)-9-methyl-9H-2-purinyl]-3-ethyl-1-pentyn-3-ol Hydrochloride NMR (400 MHz, [δ, $d_6$-DMSO); 1.01 (t, J=7.2 Hz, 6H),] δ, *DMSO-$d_6$); 1.01 (t, J=7.2 Hz, 6H),* 1.61–1.75 (m, 4H), 3.85 (s, 3H), 7.51–7.57 (m, 1H), 7.60–7.67 (m, 2H). ESI MS; 372 ($M^+$+1). m.p.; 207–210° C.

EXAMPLE 125

1-{2-[6-Amino-9-methyl-8-(2,3,5-trifluorophenyl)-9H-2-purinyl]-1-ethynyl}-1-cyclopentanol NMR (400 MHz, [δ, $d_6$-DMSO);] δ, *DMSO-$d_6$);* 1.65–1.82 (m, 4H), 1.83–1.98 (m, 4H), 3.65 (m, 3H), 5.44 (s, 1H), 7.50–7.60 (m, 3H), 7.81–7.90 (m, 1H). ESI MS; 388 ($M^+$+1). m.p.; 214–217° C.

EXAMPLE 126

1-{2-[6-Amino-9-methyl-8-(2,3,5-trifluorophenyl)-9H-2-purinyl]-1-ethynyl}-1-cyclobutanol NMR (400 MHz, [δ, $d_6$-DMSO);] δ, *DMSO-$d_6$);* 1.73–1.86 (m, 2H), 2.17–2.27 (m, 2H), 2.34–2.43 (m, 2H), 3.65 (s, 3H), 6.00 (S, 1H), 7.50–7.62 (m, 3H), 7.81–7.90 (m, 1H). ESI MS; 374 ($M^+$+1). m.p.; 231–234° C.

EXAMPLE 127

1-{2-[6-Amino-8-(2,3-difluorophenyl)-9-methyl-9H-2-purinyl]-1-ethynyl}-1-cyclobutanol NMR (400 MHz, [δ, $d_6$-DMSO);] δ, *DMSO-$d_6$);* 1.73–1.86 (m, 2H), 2.17–2.27 (m, 2H), 2.34–2.43 (m, 2H), 3.63 (s, 3H), 6.00 (S, 1H), 7.40–7.47(m, 1H), 7.52–7.60 (m, 3H), 7.66–7.74 (m, 1H). ESI MS; 356 ($M^+$+1). m.p.; 225–229° C.

EXAMPLE 128

1-[-6-Amino-8-(3-fluorophenyl)-9-methyl-9H-2-purinyl]-3,4-dimethyl-1-pentyn-3-ol Hydrochloride NMR (400 MHz, [δ, $d_6$-DMSO); 1.01 (dd, J=17.0 and 17.0,6H),] δ, *DMSO-$d_6$); 1.01 (dd, J=17.0 and 17.0,6H),* 1.24 (br s, 1H), 1.41 (s, 3H), 1.73–1.86 (m, 1H), 3.81 (s, 3H). ESI MS; 354.1 ($M^+$+1). m.p.; 191–192° C.

EXAMPLE 129

1-[6-Amino-8-(3-fluorophenyl)-9-methyl-9H-2-purionyl]-3,4,4-trimethyl-1-pentyn-1-ol Hydrochloride NMR (400 MHz, [δ, $d_6$-DMSO);] δ, *DMSO-$d_6$);* 1.04 (s,9H), 1.44 (s, 3H), 3.83 (s, 3H), 7.42–7.48 (m, 1H), 7.58–7.77 (m, 3H). ESI MS; 368.1 ($M^+$+1). m.p.; 193–194° C.

EXAMPLE 130

1-{2-[6-Amino-8-(3-fluorophenyl)-9-methyl-9H-2-purinyl]-1-ethynyl}-4-phenyl-1-cycloheanol Hydrochloride NMR (400 MHz, [δ, $d_6$-DMSO);] δ, *DMSO-$d_6$);* 1.60–2.14 (m, 9H), 2.41–2.49 (m, 1H), 3.81 (s, 3H), 7.16–7.76 (m, 8H). ESI MS; 442 ($M^+$+1). m.p.; 247–249° C.

EXAMPLE 131

1-{2-[6-Amino-9-methyl-8-(5-methyl-2-furyl)-9H-2-purinyl]-1-ethynyl}-1-cycloheanol Hydrochloride NMR (400 MHz, [δ, $d_6$-DMSO);] δ, *DMSO-$d_6$);* 1.60–1.80 (m, 4H), 1.82–1.99 (m, 4H), 2.41 (s, 3H), 3.87 (s, 3H), 4.23 (br, 3H), 6.41 (s, 1H), 7.19 (s, 1H). ESI MS; 38 ($M^+$+1). m.p.; 184–186° C.

EXAMPLE 132

1-[6-Amino-8-(3-fluorophenyl)-9-propyl-9H-2-purinyl]-3-ethyl-1-pentyn-3-ol Hydrochloride NMR (400 MHz, [δ, $d_6$-DMSO); 0.72 (t, J=7.6 Hz, 3H), 1.01 (t, J=7.6 Hz, 6H),] δ, *DMSO-$d_6$); 0.72 (t, J=7.6 Hz, 3H), 1.01 (t, J=7.6 Hz, 6H),* 1.58–1.73 (m, 6H), [4.24 (t, J=7.6 Hz, 2H),] *4.24 (t, J=7.6 Hz, 2H),* 7.42–7.49 (m, 1H), 7.63–7.69 (m, 3H). ESI MS; 382 ($M^+$+1). m.p.; 144–147° C.

EXAMPLE 133

1-{2-[6-Amino-9-ethyl-8-(3-fluorophenyl)-9H-2-purinyl]-1-ethynyl}-1-cyclopentanol Hydrochloride NMR (400 MHz, [δ, $d_6$-DMSO); 1.29 (t, J=7.2 Hz, 3H,] δ, *DMSO-$d_6$); 1.29 (t, J=7.2 Hz, 3H),* 1.66–1.82 (m, 4H), 1.86–2.02 (m, 4H), [4.31 (q, J=7.2 Hz, 2H),] *4.31 (q, J=7.2 Hz, 2H),* 7.46–7.52 (m, 1H), 7.64–7.72 (m, 3H). FAB MS; 366 ($M^+$+1). m.p.; 188–191° C.

EXAMPLE 134

2-{2-[6-Amino-8-(2-fluorophenyl)-9-methyl-9H-2-purinyl]-1-ethynyl}-1,2,3-propanetriol Hydrochloride NMR (400 MHz, [δ, $d_6$-DMSO);] δ, *DMSO-$d_6$);* 3.17 (s, 2H), [3.50 (d, J=10.8 Hz, 2H), 3.55 (d, J=10.8 Hz, 2H),] *3.50 (d, J=10.8 Hz, 2H), 3.55 (d, J=10.8 Hz, 2H),* 3.82 (s, 3H), 7.40–7.47 (m, 1H), 7.61–7.75 (m, 3H). ESI MS; 358 ($M^+$+1). m.p.; 233–235° C.

EXAMPLE 135

1-{2-[6-Amino-8-(3,5-difluorophenyl)-9-ethyl-9H-2-purinyl]-1-ethynyl}-1-cyclopentanol Hydrochloride NMR (400 MHz, [δ, $d_6$-DMSO); 1.26 (t, J=18.0 Hz, 3H),] δ, *DMSO-$d_6$); 1.26 (t, J=18.0 Hz, 3H),* 1.64–1.80 (m, 4H), 1.84–1.98 (m, 4H), [4.29 (q, J=18.0 Hz, 2H),] *4.29 (q, J=18.0 Hz, 2H),* 7.50–7.58 (m, 3H). ESI MS; 384.0 ($M^+$+1). m.p.; 217–218° C.

EXAMPLE 136

1-[6-Amino-8-(3,5-difluorophenyl)-9-ethyl-9H-2-purinyl]-3-ethyl-1-pentyn-3-ol Hydrochloride NMR (400 MHz, [δ, $d_6$-DMSO); 1.01 (t, J=18.0 Hz, 6H), 1.25 (t, J=18.0 Hz, 3H),] δ, *DMSO-$d_6$); 1.01 (t, J=18.0 Hz, 6H), 1.25 (t, J=18.0 Hz, 3H),* 1.58–1.74 (m, 4H), [4.30 (q, J=17.4 Hz, 2H),] *4.30 (q, J=17.4 Hz, 2H),* 7.47–7.60 (m, 3H). ESI MS; 386.2 ($M^+$+1). m.p.; 204–205° C.

EXAMPLE 137

1-{2-[6-Amino-8-(3,5-difluorophenyl)-9-ethyl-9H-2-purinyl]-1-ethynyl}-1-cyclobutanol Hydrochloride NMR (400 MHz, [δ, $d_6$-DMSO); 1.62 (t, J=18.0 Hz, 3H),] δ, *DMSO-$d_6$); 1.62 (t, J=18.0 Hz, 3H),* 1.76–1.88 (m, 2H), 2.18–2.29 (m, 2H), 2.36–2.44 (m, 2H), [4.30 (q, J=18.0 Hz, 2H),] *4.30 (q, J=18.0 Hz, 2H),* 7.49–7.59 (m, 3H). ESI MS; 370.0 ($M^+$+1). m.p.; 234–235° C.

EXAMPLE 138

4-[6-Amino-8-(3,5-difluorophenyl)-9-ethyl-9H-2-purinyl]2-methyl-3-butyn-2-ol Hydrochloride NMR (400 MHz, [δ, $d_6$-DMSO); 1.25 (t, J=17.6 Hz, 3H),] δ, *DMSO-$d_6$); 1.25 (t, J=17.6 Hz, 3H),* 1.48 (s, 6H), [4.29 (q, J=17.4 Hz, 2H),] *4.29 (q, J=17.4 Hz, 2H),* 7.49–7.58 (m, 3H). ESI MS; 358.0 ($M^+$+1).

EXAMPLE 139

1-{2-[6-Amino-9-cyclopropyl-8-(3,5-difluorophenyl)-9H-2-purinyl]1-ethynyl}-1-cyclopentanol Hydrochloride NMR (400 MHz, [δ, $d_6$-DMSO);] δ, *DMSO-$d_6$);* 0.70–0.78 (m, 2H), 1.02–1.11 (m, 2H), 1.64–1.82 (m, 4H), 1.84–1.99 (m, 4H), 3.67–3.74 (m, 1H), 7.45–7.53 (m, 1H), 7.65–7.73 (m, 2H). ESI MS; 396.1 ($M^+$+1). m.p.; 265–266° C.

EXAMPLE 140

1-{-[6-Amino-9-cyclopropyl-8-(3,5-difluorophenyl)-9H-2-purinyl]-1-ethynyl}-1-cyclobutanol Hydrochloride NMR (400 MHz, [δ, $d_6$-DMSO);] δ, *DMSO-$d_6$);* 0.70–0.78 (m, 2H), 1.02–1.11 (m, 2H), 1.72–1.86 (m, 2H), 2.16–2.28 (m, 2H), 2.30–2.46 (m, 2H), 3.65–3.74 (m, 1H), 7.43–7.53 (m, 1H), 7.64–7.74 (m, 2H). ESI MS; 382.1 ($M^+$+1). m.p.; 228° C.

EXAMPLE 141

4-[6-Amino-9-cyclopropyl-8-(3,5-difluorophenyl)-9H-2-purinyl]-2-methyl-3-butyn-2-ol Hydrochloride NMR (400 MHz, [δ, $d_6$-DMSO);] δ, *DMSO-$d_6$);* 0.70–0.77 (m, 2H), 1.03–1.11 (m, 2H), 1.48 (s, 6H), 3.66–3.76 (m, 1H), 7.44–7.53 (m, 1H), 7.65–7.73 (m, 2H). ESI MS; 370.1 ($M^+$+1). m.p.; 245° C.

EXAMPLE 142

1-[6-Amino-9-cyclopropyl-8-(3-fluorophenyl)-9H-purinyl]-3-ethynyl-1-pentyn-3-ol Hydrochloride NMR (400 MHz, [δ, $d_6$-DMSO);] δ, *DMSO-$d_6$);* 0.70–0.75 (m, 2H), 0.97–1.10 (m, 8H), 1.60–1.79 (m, 4H), 3.67–3.73 (m, 1H), 7.39–7.45 (m, 1H), 7.59–7.66 (m, 1H), 7.77–7.84 (m, 2H). FAB MS; 380 ($M^+$+1). m.p.; 145–148° C.

EXAMPLE 143

4-[6-Amino-9-cyclopropyl-8-(3-fluorophenyl)-9H-2-purinyl]-2-methyl-3-butyn-2-ol Hydrochloride NMR (400 MHz, [δ, $d_6$-DMSO);] δ, *DMSO-$d_6$);* 0.70–0.75 (m, 2H), 1.00–1.10 (m, 2H), 1.49 (s, 6H), 3.67–3.73 (m, 1H), 7.38–7.45 (m, 1H), 7.59–7.66 (m, 1H), 7.77–7.84 (m, 2H). ESI MS; 352 ($M^+$+1). m.p.; 143–145° C.

EXAMPLE 144

1-[6-Amino-8-(3,5-difluorophenyl)-9-propyl-9H-2-purinyl]-3-ethynyl-1-pentyn-8-ol Hydrochloride NMR (400 MHz, [δ, $d_6$-DMSO); 0.72 (t, J=7.6 Hz, 3H), 1.01 (t, J=7.6 Hz, 6H),] δ, *DMSO-$d_6$); 0.72 (t, J=7.6 Hz, 3H), 1.01 (t, J=7.6 Hz, 6H),* 1.58–1.75 (m, 6H), [4.27 (t, J=7.6 Hz, 2H),] *4.27 (t, J=7.6 Hz, 2H),* 7.48–7.58 (m, 3H). ESI MS; 400 ($M^+$+1). m.p.; 183–184° C.

EXAMPLE 145

1-{2-[6-Amino-8-(3,5-difluorophenyl)-9-propyl-9H-2-purinyl]-1-ethynyl}-1-cyclopentanol Hydrochloride NMR (400 MHz, [δ, $d_6$-DMSO); 0.72 (t, J=7.6 Hz, 3H),] δ, *DMSO-$d_6$); 0.72 (t, J=7.6 Hz, 3H),* 1.57–1.81 (m, 4H), [4.23 (t, J=7.6 Hz, 2H),] *4.23 (t, J=7.6 Hz, 2H),* 7.48–7.57 (m, 3H). ESI MS; 398 ($M^+$+1). m.p.; 210–211° C.

EXAMPLE 146

1-{2-[6-Amino-8-(2-fluorophenyl)-9-methyl-9H-2-purinyl]-1-ethynyl}-1-cyclobutanol NMR (400 MHz, [δ, $d_6$-DMSO);] δ, *DMSO-$d_6$);* 1.72–1.85 (m, 2H), 2.17–2.27 (m, 2H), 2.34–2.43 (m, 2H), 3.60 (s, 3H), 6.00 (s, 1H), 7.38–7.59 (m, 4H), 7.61–7.74 (m, 2H). ESI MS; 338 ($M^+$+1). m.p.; 136–138° C.

EXAMPLE 147

1-{2-[6-Amino-8-(2-fluorophenyl)-9-methyl-9H-2-purinyl]-1-ethynyl}-1-cyclopentanol NMR (400 MHz, [δ, $d_6$-DMSO);] δ, *DMSO-$d_6$);* 1.65–1.80 (m, 4H), 1.80–1.96 (m, 4H), 3.59 (s, 3H), 5.47 (s, 1H), 7.41–7.49 (m, 4H), 7.64–7.74 (m, 2H). ESI MS; 352 ($M^+$+1). m.p.; 166–168° C.

EXAMPLE 148

1-[6-Amino-9-methyl-8-(5-methyl-2-furyl)-9H-2-purinyl]-3-ethyl-1-pentyn-3-ol Hydrochloride NMR (400 MHz, [δ, $d_6$-DMSO); 0.99 (t, J=7.2 Hz, 6H), 1.62 (q, J=7.2 Hz, 2H), 1.64 (q, J=7.2 Hz, 2H),] δ, *DMSO-$d_6$); 0.99 (t, J=7.2 Hz, 6H), 1.62 (q, J=7.2 Hz, 2H), 1.64 (q, J=7.2 Hz, 2H),* 2.40 (s, 3H), 3.17 (s, 1H), 3.86 (s, 3H), [6.41 (d, J=0.4 Hz, 1H), 7.18 (d, J=0.4 Hz, 1H).] *6.41 (d, J=0.4 Hz, 1H), 7.18 (dd, J=0.4 Hz, 1H).* ESI MS; 340 ($M^+$+1). m.p.; 229–230° C.

EXAMPLE 149

1-[6-Amino-8-(2-fluorophenyl)-9-methyl-9H-2-purinyl]-3-ethyl-1-pentyn-1-ol

NMR (400 MHz, [δ, $d_6$-DMSO); 0.98 (t, J=7.4 Hz, 6H),] δ, *DMSO-$d_6$); 0.98 (t, J=7.4 Hz, 6H),* 1.58–1.68 (m, 4H), 3.57 (s, 3H), 5.29 (s, 1H), 7.39–7.46 (m, 4H), 7.63–7.71 (m, 2H). ESI MS; 354 ($M^+$+1). m.p.; 199–201° C.

EXAMPLE 150

1-[6-Amino-9-cyclopropyl-8-(3,5-difluorophenyl)-9H-2-purinyl]-3-ethyl-1-pentyn-3-ol Hydrochloride NMR (400 MHz, [δ, $d_6$-DMSO);] δ, *DMSO-$d_6$);* 0.72–0.78 (m, 2H), [1.01 (t, J=7.2 Hz, 6H),] *1.01 (t, J=7.2 Hz, 6H),* 1.04–1.12 (m, 2H), 1.58–1.75 (m, 4H), 3.67–3.77 (m, 1H), 7.46–7.54 (m, 1H), 7.65–7.73 (m, 2H). ESI MS; 398.2 ($M^+$+1). m.p.; 225° C.

EXAMPLE 151

4-[6-Amino-8-(3,5-difluorophenyl)-9-methyl-9H-2-purinyl]-2-methyl-3-butyn-2-ol Hydrochloride NMR (400 MHz, [δ, $d_6$-DMSO);] δ, *DMSO-$d_6$);* 1.48 (s, 6H), 3.17 (s, 3H), 7.46–7.66 (m, 3H). ESI MS; 344.0 ($M^+$+1). m.p.; 237–238° C.

EXAMPLE 152

1-[6-Amino-8-(2,5-difluorophenyl)-9-methyl-9H-2-purinyl]-3-ethyl-1-pentyn-3-ol Hydrochloride NMR (400 MHz, [δ, $d_6$-DMSO); 1.01 (t, J=18 Hz, 6H), 1.60–1.74 (q, J=18 Hz,4H),] δ, *DMSO-$d_6$); 1.01 (t, J=18 Hz, 6H), 1.60–1.74 (q, J=18 Hz,4H),* 3.65 (s, 3H), 7.53–7.65 (m, 3H). ESI MS; 372.2 ($M^+$+1). m.p.; 147–148° C.

EXAMPLE 153

4-[6-Amino-8-(2,5-difluorophenyl)-9-methyl-9H-2-purinyl]-2-methyl-3-butyn-2-ol Hydrochloride NMR (400 MHz, [δ, $d_6$-DMSO);] δ, *DMSO-$d_6$);* 1.50 (s, 6H), 3.67 (s, 3H), 7.54–7.68 (m, 3H). ESI MS; 344.0 ($M^+$+1). m.p.; 177–178° C.

EXAMPLE 154

4-[6-Amino-8-(2,3-difluorophenyl)-9-ethyl-9H-2-purinyl]-2-methyl-3-butyn-2-ol Hydrochloride NMR (400 MHz, [δ, $d_6$-DMSO); 1.25 (t, J=7.2 Hz, 3H), 1.49 (s, 6H), 4.10 (q, J=7.2 Hz, 2H),] δ, *DMSO-$d_6$); 1.25 (t, J=7.2 Hz, 3H), 1.49 (s, 6H), 4.10 (q, J=7.2 Hz, 2H),* 7.41–7.56 (m, 2H), 7.60–7.79 (m, 1H). ESI MS; 358 ($M^+$+1). m.p.; 213–215° C.

EXAMPLE 155

1-[6-Amino-8-(2,3-difluorophenyl)-9-ethyl-9H-2-purinyl]-3-ethyl-1-pentyn-3-ol Hydrochloride NMR (400 MHz, [δ, $d_6$-DMSO); 1.00 (t, J=7.2 Hz, 6H), 1.22 (t, J=7.2 Hz, 3H), 1.64 (q, J=7.2 Hz, 2H), 1.65 (q, J=7.2 Hz, 2H), 4.10 (q, J=7.2 Hz, 2H),] δ, *DMSO-$d_6$); 1.00 (t, J=7.2 Hz, 6H), 1.22 (t, J=7.2 Hz, 3H), 1.64 (q, J=7.2* Hz, 2H), *1.65 (q, J=7.2 Hz, 2H), 4.10 (q, J=7.2 Hz, 2H),* 7.42–7.57 (m, 2H), 7.69–7.78 (m, 1H). ESI MS: 386 ($M^+$+1). m.p.; 222–224° C.

EXAMPLE 156

4-[6-Amino-8-(2-fluorophenyl)-9-methyl -9H-2-purinyl]-2-methyl-3-butyn-2-ol

NMR (400 MHz, [δ, $d_6$-DMSO);] δ, *DMSO-$d_6$);* 1.46 (s, 6H), 3.60 (s, 3H), 5.60 (s, 1H), 7.41–7.54 (m, 4H), 7.64–7.74 (m, 2H). ESI MS; 326 ($M^+$+1). m.p.; 198–199° C.

EXAMPLE 157

1-{2-[6-Amino-8-(2,3-difluorophenyl)-9-methyl-9H-2-purinyl]-1-ethynyl}-1-cyclopentanol Hydrochloride NMR (400 MHz, [δ, $d_6$-DMSO); 1.23 (t, J=7.2 Hz, 3H),] δ, *DMSO-$d_6$); 1.23 (t, J=*7.2 Hz, 3H), 1.74–1.86 (m, 2H), 2.18–2.27 (m, 2H), 2.36–2.43 (m, 2H), [4.09 (q, J=14.4 Hz, 2H),] *4.09 (q, J=14.4 Hz, 2H),* 7.42–7.47 (m, 1H), 7.51–7.55 (m, 1H), 7.69–7.76 (m, 1H). ESI MS; 370 ($M^+$+1). m.p.; 139–142° C.

EXAMPLE 158

1-{2-[6-Amino-8-(2,3-difluorophenyl)-9-ethyl-9H-2-purinyl]-1-ethynyl}-1-cyclopentanol Hydrochloride NMR (400 MHz, [δ, $d_6$-DMSO); 1.24 (t, J=7.0 Hz, 3H),] δ, *DMSO-$d_6$); 1.24 (t, J=7.0 Hz, 3H),* 1.65–1.80 (m, 4H), 1.85–2.00 (s,4H), 4.05–4.15 (m, 2H), 5.10 (s, 1H), 7.42–7.58 (m, 2H), 7.69–7.78 (m, 2H). ESI MS; 384 ($M^+$+1). m.p.; 138–140° C.

EXAMPLE 159

4-[6-Amino-8-(3,5-difluorophenyl)-9-propyl-9H-2-purinyl]-2-methyl-1-butyn-2-ol Hydrochloride NMR (400 MHz, [δ, $d_6$-DMSO); 0.71 (t, J=7.6 Hz, 3H),] δ, *DMSO-$d_6$); 0.71 (t, J=7.6 Hz, 3H),* 1.49 (s, 6H), 1.57–1.68 (m, 2H), [4.25 (t, J=7.6 Hz, 2H),] *4.25 (t, J=7.6 Hz, 2H),* 7.50–7.58 (m, 3H). ESI MS; 372 ($M^+$+1). m.p.; 148–150° C.

EXAMPLE 160

1-{2-[6-Amino-9-cyclopropyl-8-(3-fluorophenyl)-9H-2-purinyl]-1-ethynyl}-1-cyclobutanol Hydrochloride NMR (400 MHz, [δ, $d_6$-DMSO);] δ, *DMSO-$d_6$);* 0.74 (bs, 2H), 1.02–1.11 (m, 2H), 1.76–1.90 (m, 2H), 2.20–2.31 (m, 2H), 2.38–2.50 (m, 2H), 3.69–3.77 (m, 1H), 7.41–7.48 (m, 1H), 7.60–7.67 (m, 1H), 7.79–7.86 (m, 2H). ESI MS; 364 ($M^+$+1). m.p.; 167–170° C.

EXAMPLE 161

1-{2-[6-Amino-8-(2,3-difluorophenyl)-9-propyl-9H-2-purinyl]-1-ethynyl}-1-cyclobutanol Hydrochloride NMR (400 MHz, [δ, $d_6$-DMSO); 0.70 (t, J=7.6 Hz, 3H), 1.64 (tq, J=7.6 Hz, 7.6 Hz, 2H),] δ, *DMSO-$d_6$); 0.70 (t, J=7.6 Hz, 3H), 1.64 (tq, J=7.6 Hz, 7.6 Hz, 2H),* 1.67–1.83 (m, 2H), 2.23–2.32 (m, 2H), 2.39–2.50 (m, 2H), [4.10 (t, J=7.6 Hz, 2H),] *4.10 (t, J=7.2 Hz, 2H),* 7.44–7.52 (m, 1 Hz), 7.53–7.59 (m, 1H), 7.72–7.81 (m, 1H). ESI MS; 384 ($M^+$+1). m.p.; 124–127° C.

EXAMPLE 162

1-{2-[6-Amino-8-(2,3-difluorophenyl)-9-propyl-9H-2-purinyl]-1-ethynyl}-1-cyclobutanol Hydrochloride NMR (400 MHz, [δ, $d_6$-DMSO); 0.69 (t, J=7.6 Hz, 3H), 1.63 (tq, J=7.6 Hz, 7.6 Hz, 2H),] δ, *DMSO-$d_6$); 0.69 (t, J=7.6 Hz, 3H), 1.63 (tq, J=7.6 Hz, 7.6 Hz, 2H),* 1.67–1.82 (m, 4H), 1.85–2.00 (m, 4H), [4.07 (t, J=7.6 Hz, 2H),] *4.07 (t, J=7.6 Hz, 2H),* 7.43–7.50 (m, 1H), 7.50–7.59 (m, 1H), 7.70–7.79 (m, 1H). ESI MS; 398 ($M^+$+1). m.p.; 184–188° C.

EXAMPLE 163

4-[6-Amino-8-(2,3-difluorophenyl)-9-propyl-9H-2-purinyl]-2-methyl-3-butyl-2-ol Hydrochloride NMR (400 MHz, [δ, $d_6$-DMSO); 0.68 (t, J=7.6 Hz, 3H), 1.49 (s, 6H), 1.62 (tq, J=7.6 Hz, 7.6 Hz, 2H), 4.07 (t, J=7.6 Hz, 2H),] δ, *DMSO-$d_6$); 0.68 (t, J=7.6 Hz, 3H), 1.49 (s, 6H), 1.62 (tq, J=7.6 Hz, 7.6 Hz, 2H), 4.07 (t, J=7.6 Hz, 2H),* 7.43–7.49 (m, 1H), 7.51–7.57 (m, 1H), 7.70–7.78 (m, 1H). ESI MS; 372 ($M^+$+1). m.p.; 230–233° C.

EXAMPLE 164

1-[6-Amino-8-(2,3-difluorophenyl)-9-propyl-9H-2-purinyl]-3-ethyl-1-pentyn-3-ol Hydrochloride NMR (400 MHz, [δ, $d_6$-DMSO); 0.68 (t, J=7.6 Hz, 3H), 1.01 (t, J=7.6 Hz, 6H), 1.59–1.75 (m, 6H) 4.08 (t, J=7.6 Hz, 2H),] δ, *DMSO-$d_6$); 0.68 (t, J=7.6 Hz, 3H), 1.01 (t, J=7.6 Hz, 6H), 1.59–1.75 (m, 6H), 4.08 (t, J=7.6 Hz, 2H),* 7.48–7.50 (m, 1H), 7.52–7.57 (m, 1H), 7.71–7.79 (m, 1H). ESI MS; 400 ($M^+$+1). m.p.; 187–188° C.

EXAMPLE 165

1-{2-[6-Amino-8-(2,5-difluorophenyl)-9-cyclopropyl-9H-2-purinyl]-1-ethynyl}-1-cyclobutanol NMR (400 MHz, [δ, $d_6$-DMSO);] δ, *DMSO-$d_6$);* 0.67–0.72 (m, 2H), 0.89–0.97 (m, 2H), 1.73–1.87 (m, 2H), 2.17–2.28 (m, 2H), 2.35–2.45 (m, 2H), 3.37–3.47 (m, 1H), 7.49–7.56 (m, 2H), 7.59–7.66 (m, 1H). ESI MS: 382 ($M^+$+1). m.p.; 161–164° C.

EXAMPLE 166

1-{2-[6-Amino-8-(2,5-difluorophenyl)-9-cyclopropyl-9H-2-purinyl]-1-ethynyl}-1-cyclopentanol NMR (400 MHz, [δ, $d_6$-DMSO);] δ, *DMSO-$d_6$);* 0.66–0.73 (m, 2H), 0.89–0.97 (m, 2H), 1.63–1.82 (m, 4H), 1.83–1.98 (m, 4H), 3.37–3.46 (m, 1H), 7.49–7.56 (m, 2H), 7.59–7.66 (m, 1H). ESI MS: 396 ($M^+$+1). m.p.; 230–232° C.

EXAMPLE 167

4-[6-Amino-8-(2,5-difluorophenyl)-9-cyclopropyl-9H-2-purinyl]-2-methyl-3-butyn-2-ol NMR (400 MHz, [δ, $d_6$-DMSO);] δ, *DMSO-$d_6$);* 0.65–0.73 (m, 2H), 0.88–0.98 (m, 2H), 1.48 (s, 6H), 3.37–3.46 (m, 1H), 7.40–7.75 (br, 2H), 7.48–7.55 (m, 2H), 7.59–7.65 (m, 1H). EST MS; 370 ($M^+$+1). m.p.; 196–198° C.

EXAMPLE 168

1-[6-Amino-8-(2,5-difluorophenyl)-9-cyclopentyl-9H-2-purinyl]-3-ethyl-1-pentyl-3-ol NMR (400 MHz, [δ, $d_6$-DMSO);] δ, *DMSO-$d_6$);* 0.66–0.73 (m, 2H), 0.89–0.97 (m, 2H), [1.00 (t, J=7.2 Hz, 6H)] *1.00 (t, J=7.2 Hz, 6H),* 1.60–1.73 (m, 4H), 3.39–3.46 (m, 1H), 7.49–7.56 (m, 2H), 7.59–7.65 (m, 1H). ESI MS; 398 ($M^+$+1). m.p.; 215–216° C.

EXAMPLE 169

1-{2-[6-Amino-8-(3-fluorophenyl)-9-propyl-9H-2-purinyl]-1-ethynyl}-1-cyclopentanol Hydrochloride NMR (400 MHz, [δ, $d_6$-DMSO); 0.84 (t, J=7.2 Hz, 3H), 1.70–2.22 (m, 10H), 4.37 (t, J=7.4 Hz, 2H),] δ, *DMSO-$d_6$); 0.84 (t, J=7.2 Hz, 3H), 1.70–2.22 (m, 10H), 4.37 (t, J=7.4 Hz, 2H),* 7.27–7.32 (m, 1H), 7.50–7.59 (m, 3H). ESI MS; 380 ($M^+$+1). m.p.; 198–200° C.

EXAMPLE 170

1-{2-[6-Amino-8-(3-fluorophenyl)-9-propyl-9H-2-purinyl]-1-ethynyl}-1-cyclobutanol Hydrochloride NMR (400 MHz, [δ, $d_6$-DMSO); 0.87 (t, J=7.2 Hz, 3H),] δ, *DMSO-$d_6$); 0.87 (t, J=7.2 Hz, 3H),* 1.79–2.01 (m, 4H), 2.33–2.42 (m, 2H), 2.46 (s, 1H), 2.62–2.71 (m, 2H), [4.38 (t, J=7.4 Hz, 2H),] *4.38 (t, J=7.4 Hz, 2H),* 7.29–7.34 (m, 1H), 7.50–7.60 (m, 3H). ESI MS; 366 ($M^+$+1). m.p.; 144–146° C.

EXAMPLE 171

4-[6-Amino-8-(3-fluorophenyl)-9-propyl-9H-2-purinyl]-2-methyl-3-butyn-2-ol Hydrochloride NMR (400 MHz, [δ, $d_6$-DMSO); 0.72 (t, J=18.0 Hz, 3H), 1.58–1.69 (m, 2H), 4.24 (q, J=18.0 Hz, 2H),] δ, *DMSO-$d_6$); 0.72 (t, J=18.0 Hz, 3H), 1.58–1.69 (m, 2H), 4.24 (q, J=18.0 Hz, 2H),* 7.43–7.49 (m, 1H), 7.61–7.70 (m, 3H). ESI MS; 354.1 ($M^+$+1). m.p.; 167–168° C.

EXAMPLE 172

1-{2-[2-6-Amino-8-(2,5-difluorophenyl)-9-propyl-9H-2-purinyl]-1-ethynyl}-1-cyclopentanol Hydrochloride NMR (400 MHz, [δ, $d_6$-DMSO); 0.68 (t, J=7.2 Hz, 3H),] δ, *DMSO-$d_6$); 0.68 (t, J=7.2 Hz, 3H),* 1.55–1.81 (m, 6H), 1.89–1.98 (m, 4H), [4.02 (t, J=7.2 Hz, 2H),] *4.02 (t, J=7.2 Hz, 2H),* 7.50–7.57 (m, 2H), 7.59–7.68 (m, 1H). ESI MS; 398.2 ($M^+$+1). m.p.; 232–234° C.

EXAMPLE 173

1-{2-[6-Amino-8-(2,5-difluorophenyl)-9-propyl-9H-2-purinyl]-1-ethynyl}-1-cyclobutanol Hydrochloride NMR (400 MHz, [δ, $d_6$-DMSO); 0.68 (t, J=7.2 Hz, 3H),] δ, *DMSO-$d_6$); 0.68* (t, J=7.2 Hz, 3H), 1.56–1.68 (m, 2H), 1.72–1.86 (m, 2H), 2.16–2.28 (m, 2H), 2.32–2.46 (m, 2H), [4.03 (t, J=7.2 Hz, 2H),] *4.03 (t, J=7.2 Hz, 2H),* 7.52–7.58 (m, 2H), 7.60–7.70 (m, 1H). ESI MS; 384.2 ($M^+$+1). m.p.; 225–226° C.

EXAMPLE 174

1-{2-[6-Amino-8-(2,5-difluorophenyl)-9-ethyl-9H-2-purinyl]-1-ethynyl}-1-cyclobutanol NMR (400 MHz, [δ, $d_6$-DMSO); 1.22 (t, J=7.2 Hz, 3H),] δ, *DMSO-$d_6$); 1.22 (t, I=7.2 Hz, 3H),* 1.72–1.87 (m, 2H), 2.17–2.27 (m, 2H), 2.34–2.43 (m, 2H), [4.07 (q, J=7.2 Hz, 2H),] *4.07 (q, J=7.2 Hz, 2H),* 7.51–7.59 (m, 2H), 7.59–7.67 (m, 1H). EST MS; 370 ($M^+$+1). m.p.; 141–143° C.

EXAMPLE 175

1-{2-[6-Amino-8-(2,5-difluorophenyl)-9-ethyl-9H-2-purinyl]-1-ethynyl}-1-cyclobutanol NMR (400 MHz, [δ, $d_6$-DMSO); 1.22 (t, J=7.2 Hz, 3H),] δ, *DMSO-$d_6$); 1.22 (t, J=7.2 Hz, 3H),* 1.62–1.82 (m, 4H), 1.82–1.99 (m, 4H), [4.07 (q, J=7.2 Hz, 2H),] *4.07 (q, J=7.2 Hz, 2H),* 7.48–7.58 (m, 2H), 7.58–7.66 (m, 1H). EST MS; 384 ($M^+$+1). m.p.; 191–194° C.

EXAMPLE 176

4-[6-Amino-8-(2,5-difluorophenyl)-9-ethyl-9H-2-purinyl]-2-methyl-3-butyn-2-ol

NMR (400 MHz, [δ, $d_6$-DMSO); 1.22 (t, J=7.2 Hz, 3H),] δ, *DMSO-$d_6$); 1.22 (t, J=7.2 Hz, 3H),* 1.48 (s, 6H), [4.07 (q, J=7.2 Hz, 2H),] *4.07 (q, J=7.2 Hz, 2H),* 7.49–7.58 (m, 2H), 7.58–7.66 (m, 1H). ESI MS; 358 ($M^+$+1). m.p.; 215–218° C.

EXAMPLE 177

1-[6-Amino-8-(2,5-difluorophenyl)-9-ethyl-9H-2-purinyl]-3-ethyl-1-pentyn-3-ol

NMR (400 MHz, [δ, $d_6$-DMSO); 1.00 (t, J=7.2 Hz, 6H), 1.22 (t, J=7.2 Hz, 3H),] δ, *DMSO-$d_6$); 1.00 (t, J=7.2 Hz, 6H), 1.22 (t, J=7.2 Hz, 3H),* 1.58–1.73 (m, 4H), [4.07 (q, J=7.2 Hz, 2H),] *4.07 (q, J=7.2 Hz, 2H),* 7.50–7.59 (m, 2H), 7.58–7.65 (m, 1H). ESI MS; 386 ($M^+$+1). m.p.; 163–166° C.

EXAMPLE 178

4-[6-Amino-8-(2,5-difluorophenyl)-9-propyl-9H-2-purinyl]-2-methyl-3-butyn-2-ol Hydrochloride NMR (400 MHz, [δ, $d_6$-DMSO); 0.68 (t, J=7.2 Hz, 3H),] δ, *DMSO-$d_6$); 0.68 (t, J=7.2 Hz, 3H),* 1.48 (s, 6H), 1.55–1.68 (m, 2H), [4.03 (t, J=7.2 Hz, 2H),] *4.03 (t, J=7.2 Hz, 3H),* 7.51–7.58 (m, 2H), 7.60–7.68 (m, 1H). ESI MS; 372.1 ($M^+$+1). m.p.; 194–196° C.

EXAMPLE 179

1-[6-Amino-8-(2,5-difluorophenyl)-9-propyl-9H-2-purinyl]-3-ethyl-1-pentyn-3-ol Hydrochloride NMR (400 MHz, [δ, $d_6$-DMSO); 0.67 (t, J=7.2 Hz, 3H), 1.00 (t, J=7.6 Hz, 6H), 1.55–1.74 (m, 6H), 4.03 (t, J=7.2 Hz, 3H),] δ, *DMSO-$d_6$); 0.67 (t, J=7.2 Hz, 3H), 1.00 (t, J=7.6 Hz, 6H), 1.55–1.74 (m, 6H), 4.03 (t, J=7.2 Hz, 3H),* 7.51–7.58 (m, 2H), 7.60–7.67 (m, 1H). ESI MS; 400.2 ($M^+$+1). m.p.; 164–165° C.

EXAMPLE 180

2-[6-Amino-8-(3-fluorophenyl)-2[2-(1-hydroxycyclohexyl)-1-ethynyl]-9H-9-purinyl]acetic Acid Hydrochloride To 137 mg of ethyl 2-{6-amino-8-(3-fluorophenyl)-2-[2-(1-hydroxycyclohexyl)-1-ethynyl]-9H-9-purinyl}acetate of Example 47 were added 1 ml of ethanol and 2 ml of a 1N aqueous solution of sodium hydroxide and the mixture was stirred for 30 minutes at room temperature. After the reaction solution was concentrated, the resulting residue was dissolved in water and the solution was adjusted to pH 2 with a 1N aqueous solutoin of HCl. The resulting crystals were collected by filtration and washed with water and ether to give 231 mg of the title compound. The yield was 65%.

NMR (400 MHz, [δ, $d_6$-DMSO);] δ, *DMSO-$d_6$);* 1.20–1.30 (m, 1H), 1.41–1.67 (m, 7H), 1.78–1.86 (m, 2H), 7.38–7.43 (m, 1H), 7.52–7.64 (m, 3H). FAB MS; 410 ($M^+$+1).

EXAMPLE 181

3-[6-Amino-2-{2-(1-hydroxycyclohexyl)-1-ethynyl]-9-methyl-9H-8-purinyl}benzoic Acid Hydrochloride NMR (400 MHz, [δ, $d_6$-DMSO);] δ, *DMSO-$d_6$);* 1.19–1.31 (m, 1H), 1.42–1.68 (m, 7H), 1.80–1.89 (m, 2H), 3.82 (s, 3H), [7.71 (t, J=7.7 Hz, 1H), 8.09–8.14 (m, 2H), 8.45 (d, J=1.3 Hz, 1H).] *7.71 (t, J=7.7 Hz, 1H), 8.09–8.14 (m, 2H), 8.45 (d, J=1.3 Hz, 1H).* FAB MS; 392 ($M^+$+1).

EXAMPLE 182

5-[6-Amino-8-(3-fluorophenyl)-9-methyl-9H-2-purinyl]-4-pentynoic Acid Hydrochloride NMR (400 MHz, [δ, $d_6$-DMSO);] δ, *DMSO-$d_6$);* 1.66–1.82 (m, 4H), 1.87–2.00 (m, 4H), 3.86 (s, 3H), 7.43–7.50 (m, 1H), 7.63–7.70 (m, 1H), 7.71–7.77 (m, 2H). FAB MS; 340 ($M^+$+1).

EXAMPLE 183

(E) 3-{4-{6-Amino-2-[2-(1-hydroxycyclohexyl)-1-ethynyl]-9-methyl-9H-8-purinyl}phenyl}-2-propenoic Acid Hydrochloride NMR (400 MHz, [δ, $d_6$-DMSO);] δ, *DMSO-$d_6$);* 1.21–1.33 (m, 1H), 1.42–1.69 (m, 7H), 1.78–1.89 (m, 2H), 3.81 (s, 3H), 5.54 (br s, 1H), [6.66 (d, J=16.0 Hz, 1H), 7.47 (br s, 2H), 7.68 (d, J=16.0 Hz, 1H),] *6.66 (d, J=16.0 Hz, 1H), 7.47 (br s, 2H), 7.68 (d, J–16.0 Hz, 1H),* 7.84–7.98 (m, 4H), 12.5 (br s, 1H). FAB MS; 418 ($M^+$+1).

EXAMPLE 184

2-{{8-(3-Fluorophenyl)-2-[2-(1-hydroxycyclohexyl)-1-ethynyl]-9-methyl-9H-6-purinyl}amino}acetic Acid Hydrochloride NMR (400 MHz, [δ, $d_6$-DMSO);] δ, *DMSO-$d_6$);* 1.21–1.32 (m, 1H), 1.41–1.68 (m, 7H), 1.78–1.88 (m, 2H), 3.79 (s, 3H), 5.57 (s, 2H), 7.39–7.44 (m, 1H), 7.59–7.65 (m, 1H), 7.69–7.73 (m, 2H), 8.09–8.12 (m, 1H). FAB MS; 424 ($M^+$+1).

EXAMPLE 185

2-[3-(Dimethylamino)-1-propynyl]-8-(3-fluorophenyl)-9-methyl-9H-6-purinamine Dihydrochloride 6-Chloro-8-(3-fluorophenyl)-2-iodo-9-methyl-9H-purine (200 mg) was reacted with an ammonia-saturated methanol at 70° C. for 30 minutes in a sealed tube. The reaction mixture was evaporated and then filtered to give 138 mg of 8-(3-fluorophenyl)-2-iodo-9-methyl-9H-6-purinamine.

NMR (400 MHz, [δ,] δ, $CDCl_3$); 3.84 (s, 3H), 5.76 (br s, 2H), 7.20–7.30 (m, H), 7.42–7.54 (m, 3H).

After that, a solution of 50 mg of 8-(3-fluorophenyl)-2-iodo-9-methyl-9H-6-purinamine previously obtained, 10 mg of dichlorobis(triphenylphosphine)palladium (II), 3 mg of copper (I) iodide, 22 ml of 1-dimethylamino-2-propyne and 28 ml of triethylamine in 2 ml of DMF was stirred in nitrogen atmosphere at 80° C. for 20 minutes. Since the reaction was slow, 66 ml of 1-dimethylamino-2-propyne were further added and the mixture was stirred at 80° C. for 1 hour more. The solvent was evaporated and the resulting residue was diluted with chloroform. After blowing hydrogen sulfide for about 20 seconds thereinto, a saturated aqueous solution of EDTA was added thereto and the mixture was neutralized with sodium carbonate and extracted with chloroform. The organic layer was dried over magnesium sulfate, purified by a silica column chromatography (5% methanol/dichloromethane) and converted into a hydrochloride by a common method to give 16 mg of the title compound.

NMR (400 MHz, [δ, $d_6$-DMSO);] δ, *DMSO-$d_6$);* 2.85 (s, 6H), 3.80 (s, 3H), 4.35 (s, 2H), 7.39–7.96 (m, 1H), 7.60–7.72 (m, 31H). FAB MS; 325 ($M^+$+1).

The compounds of Examples 186–201 were prepared similarly using the corresponding 6-chloro-2-iodo compounds where a chlorine group at position 6 was firstly converted to an amino group and then an iodine group at position 2 was converted to the corresponding ethynyl group.

EXAMPLE 186

1-[6-Amino-8-(2-furyl)-9-methyl-9H-2-purinyl]-4-methyl-1-pentyn-1-one

NMR (400 MHz, [δ,] δ, $CDCl_3$); 1.18 [(d, J=6.3,6H),] *(d, J=6.3,6H),* 2.66–2.80 (m, 1H), 4.08 (s, 3H), 5.64 (br, 2H), [6.64 (dd, J=2.0 Hz,0.9 Hz, 1H), 7.15 (d, J=2.0, 1H),] *6.64 (dd, J=2.0 Hz,0.9 Hz, 1H), 7.15 (d, J=2.0, 1H),* 7.68 (m, 1H).

EXAMPLE 187

3-[6-Amino-8-(2-furyl)-9-methyl-9H-2-purinyl]-1-phenyl-2-propyn-1-one

NMR (400 MHz, [δ,] δ, $CDCl_3$); 4.10 (s, 3H), 5.66 (br, 2H), [6.66 (dd, J=1.8 Hz, 3.7 Hz, 1H), 7.18 (d, J=3.7, 1H),] *6.66 (dd, J=1.8 Hz, 3.7 Hz, 1H), 7.18 (d, J=3.7, 1H),* 7.44–7.50 (m, 3H), 7.69 (m, 1H), 8.04–8.10 (m, 2H).

EXAMPLE 188

$N^1$-Isopropyl-3-[6-amino-8-(3-fluorophenyl)-9-methyl-9H-2-purinyl]-2-propynamide NMR (400 MHz, [δ, $d_6$-DMSO); 1.10 (d, J=6.0 Hz, 6H),] δ, *DMSO-$d_6$); 1.10 (d, J=6.0 Hz, 6H),* 3.80 (s, 3H), 3.86–3.98 (m, 1H), 7.38–7.45 (m, 1H), 7.58–7.74 (m, 3H), [8.90 (d, J=7.7 Hz, 1H).] *8.90 (d, J=7.7 Hz, 1H).* FAB MS; 353 ($M^+$+1).

EXAMPLE 189

$N^1$-Cyclohexyl-8-[6-amino-8-(3-fluorophenyl)-9-methyl-9H-2-purinyl]-2-propynamide NMR (400 MHz, [δ, $d_6$-DMSO);] δ, *DMSO-$d_6$);* 1.02–1.30 (m, 5H), 1.50–1.60 (m, 1H), 1.64–1.80 (m, 4H), 3.54–3.64 (m, 1H), 3.80 (s, 3H), 7.39–7.45 (m, 1H), 7.58–7.74 (m, 3H), [8.91 (d, J=8.2 Hz, 1H).] *8.91 (d, J=8.2 Hz, 1H).*

EXAMPLE 190

$N^1$-Phenyl-3-[6-amino-8-(3-fluorophenyl)-9-methyl-9H-2-purinyl]-2-propynamide

NMR (400 MHz, [δ, $d_6$-DMSO);] δ, *DMSO-$d_6$);* 3.80 (s, 3H), 7.08–7.12 (m, 1H), 7.30–7.36 (m, 2H), 7.39–7.45 (m, 1H), 7.60–7.74 (m, 5H), 11.10 (s, 1H). FAB MS; 387 ($M^+$+1).

EXAMPLE 191

3-[6-Amino-8-(3-fluorophenyl)-9-methyl-9H-purinyl]-1-piperidino-2-propyn-1-one

NMR (400 MHz, [δ, $d_6$-DMSO);] δ, *DMSO-$d_6$);* 1.42–1.64 (m, 6H), 3.50 (br, 2H), 3.72 (br, 2H), 3.80 (s, 3H), 7.40–7.45 (m, 1H), 7.60–7.78 (m, 3H). FAB MS; 379 ($M^+$+1).

EXAMPLE 192

3-[6-Amino-8-(3-fluorophenyl)-9-methyl-9H-2-purinyl]-1-morpholino-2-propyn-1-one NMR (400 MHz, [δ, $d_6$-DMSO); 3.66 (t, J=4.1 Hz, 2H), 3.74 (t, J=4.1 Hz, 2H),] δ, *DMSO-$d_6$); 3.66 (t, J=4.1 Hz, 2H), 3.74 (t, J=4.1 Hz, 2H),* 3.80 (s, 3H), 7.38–7.45 (m, 1H), 7.60–7.74 (m, 3H).

EXAMPLE 193

2-[2-[4-Aminophenyl]-1-ethynyl]-8-(3-fluorophenyl)-9-methyl-9H-2-purinamine Dihydrochloride NMR (400 MHz, [δ, $d_6$-DMSO);] δ, *DMSO-$d_6$);* 3.10 (s, 3H), 6.69–6.78 (br s, 2H), 7.34–7.40 (m, 2H), 7.41–7.47 (m, 1H), 7.60–7.74 (m, 5H). FAB MS; 359 ($M^+$+1).

EXAMPLE 194

N-[3-[6-Amino-8-(3-fluorophenyl)-9-methyl-9H-2-purinyl]-1,1-dimethyl-2-propyl]methanesulfonamide Hydrochloride NMR (400 MHz, [δ, $d_6$-DMSO);] δ, *DMSO-$d_6$);* 1.62 (s, 6H), 3.19 (s, 3H), 3.83 (s, 3H), 7.40–7.47 (m, 1H), 7.60–7.66 (m, 2H), 7.67–7.75 (m, 2H). FAB MS; 403 ($M^+$+1).

EXAMPLE 195

Ethyl-N-{3-amino-8-(3-fluorophenyl)-9-methyl-9H-2-purinyl]-1,1-dimethyl-2-propyl}carbamate Hydrochloride NMR (400 MHz, [δ, $d_6$-DMSO); 1.18 (t, J=7.0 Hz, 3H),] δ, *DMSO-$d_6$); 1.18 (t, J=7.0 Hz, 3H),* 1.56 (s, 6H), 3.80 (s, 3H), [4.00 (q, J=7.0 Hz, 2H),] *4.00 (q, J=7.0 Hz, 2H),* 7.39–7.45 (m, 1H), 7.49 (br s, 2H), 7.54 (br s, 1H), 7.59–7.66 (m, 1H), 7.78–7.74 (m, 2H). FAB MS; 397 ($M^+$+1).

EXAMPLE 196

4-[6-Amino-8-(3-fluorophenyl)-9-methyl-9H-2-purinyl]-2-phenyl-3-buten-2-ol

NMR (400 MHz, [δ,] δ, $CDCl_3$); 1.93 (s, 3H), 2.86 (br s, 1H), 3.90 (s, 3H), 5.72 (br s, 2H), 7.21–7.29 (m, 1H), 7.29–7.33 (m, 1H), 7.35–7.41 (m, 2H), 7.47–7.57 (m, 3H), 7.73–7.78 (m, 2H).

EXAMPLE 197

3-[6-Amino-8-(3-fluorophenyl)-9-methyl-9H-2-purinyl]-1-(2-methoxyphenyl)-2-propyn-1-ol NMR (400 MHz, [δ,] δ, $CDCl_3$); 3.48 (s, 1H), 3.88 (s, 3H), 3.92 (s, 3H), 5.95 (br s, 2H), 6.91–6.94 (m, 1H), 6.96–7.01 (m, 1H), 7.21–7.26 (m, 1H), 7.28–7.34 (m, 1H), 7.46–7.56 (m, 3H), 7.62–7.66 (m, 1H).

EXAMPLE 198

4-[6-Amino-8-(3-fluorophenyl)-9-methyl-9H-2-purinyl]-2-(3-pyridyl)-3-butyn-2-ol

NMR (400 MHz, [δ,] δ, $CDCl_3$); 1.93 (s, 3H), 3.87 (s, 3H), 6.20 (br-s, 2H), 7.20–7.37 (m, 2H), 7.42–7.57 (m, 3H), 8.01–8.09 (m, 1H). ESI MS; 389 ($M^+$+1).

EXAMPLE 199

3-[6-Amino-8-(3-fluorophenyl)-9-methyl-9H-2-purinyl]-1-(3-methoxy)-2-propyn-1-ol NMR (400 MHz, [δ,] δ, $CDCl_3$); 3.83 (s, 3H), 3.88 (s, 3H), 5.71 (br-s, 1H), 5.92 (br, 2H), 6.85–6.90 (m, 1H), 7.16–7.33 (m, 4H), 7.45–7.56 (m, 3H).

EXAMPLE 200

3-[6-Amino-8-(3-fluorophenyl)-9-methyl-9H-2-purinyl]-1-(4-methoxyphenyl)-2-propyn-1-ol NMR (400 MHz, [δ,] δ, $CDCl_3$); 3.80 (s, 3H), 3.86 (s, 3H), 5.68 (br-s, 1H), 6.28 (br s, 2H), [6.88 (d, J=8.8 Hz, 2H),] *6.88 (d, J=8.8 Hz, 2H),* 7.20–7.26 (m, 1H), 7.43–7.56 (m, 5H).

EXAMPLE 201

4-[6-Amino-8-(3-fluorophenyl)-9-methyl-9H-2-purinyl]-2-(4-pyridinyl)-3-butyn-2-ol NMR (400 MHz, [δ, $d_6$-DMSO);] δ, *DMSO-$d_6$);* 1.74 (s, 3H), 3.80 (s, 3H), 6.63 (s, 1H), 7.38–7.46 (m, 1H), 7.48–7.76 (m, 7H), 8.61 (br, 2H).

EXAMPLE 202

$N^1$-Ethyl-4-[6-Amino-8-(3-fluorophenyl)-2-[2-(1-hydroxycyclohexyl-1-ethylnyl)-9H-9-purinyl] butaneamide Hydrochloride 1) 4-[6-Amino-8-(3-fluorophenyl)-2-iodo-9H-9-purinyl] butanoic Acid To 1.50 g of 4-[6-amino-8-(3-fluorophenyl)-2-iodo-9H-9-purinyl]butanol were added 30 ml of chloroform, 30 ml of acetonitrile, 45 ml of water, 73 mg of ruthenium tetraoxide hydrate and4.10 g of sodium periodate and the mixture was vigorously stirred in a nitrogen stream for 5 hours at room temperature. The reaction was stopped by 2-propanol and the insoluble matters were filtered off followed by washing with 1000 ml of chloroform-methanol (1:1). The filtrate was concentrated, the residue was suspended in water, and the suspension was adjusted to pH 2–3 with 1N hydrochloric acid and the crystals were collected by filtration. The crystals were washed with water and ether to give 1.41 g of the title compound. The yield was 91%.

NMR (400 MHz, [δ, $d_6$-DMSO);] δ, *DMSO-$d_6$);* 1.76–1.94 (m, 2H), [2.13 (t, J=7.0 Hz, 2H), 4.20 (t, J=7.2 Hz, 2H),] *2.13 (t, J=7.0 Hz, 2H), 4.20 (t, J=7.2 Hz, 2H),* 7.36–7.47 (m, 1H), 7.54–7.68 (m, 3H), 7.74 (br s, 2H).

2) Methyl 4-[6-amino-8-(3-fluorophenyl)-2-iodod-9H-9-purinyl]butanoate

Thionyl chloride (1.2 ml) was added dropwise into a mixture of 1.41 g of 4-[6-amino-8-(3-fluorophenyl)-2-iodo-9H-9-purinyl]butanoid acid and 75 ml of methanol over 15 minutes during the mixutre was stirred at 0–5° C. in a nitrogen stream. This was raised to room temperature and stirred for 45 minutes and the solvent was evaporated. The resulting residue was dissolved in ethyl acetate and then the solutionw as washed with a saturated aqueous solution of sodium bicarbonate twice and then with brine once. The orgnaic layer was dried over anhydrous sodium sulfate and concentrated to give 1.45 g of the title compound. The yield was 100%.

3) Methyl 4-{6-amino-8-(3-fluorophenyl)-2-[2-(1-hydroxycyclohexyl)-1-ethynyl]-9H-9-purinyl}butanoate]

To 162 mg of methyl 4-[6-amino-8-(3-fluorophenyl)-2-iodo-9H-9-purinyl]butanoate were added 8 ml of N,N-dimethylformamide, 30 mg of copper(I) iodide, 30 mg of dichlorobis(triphenylphosphine)palladium(II)l, 80 mg of 1-ethylcyclohexanol and 74 μl of triethylamine and the mixutre was stirred in a nitrogen stream at 70° C. for 2.5 hours. After it was allowed to cool, the solvent was evaporated and the resulting reside was subjected to a silica gel column chromatography (25 g of silica gel; chloroform-methanol (100:0–100:1–50:1) to give 144 mg of the title compound. The yield was 90%.

4$N^1$-Ethyl-4-[6-amino-8-(3-fluorophenyl)-2-[2-(1-hydroxycyclohexyl)-1-ethynyl]-9H-9-purinyl]butanoate Hydrochloride To 663 mg of methyl 4-[6-amino-8-(3-fluorophenyl)-2-[2-(1-hydroxycyclohexyl)-1-ethynyl-9H-9-purinyl] butanoate were added 20 ml of a 70% aqueous solution of ethylamine and the mixture was stirred in a sealed tube at 80° C. for 5 hours. The reaction solution was cooled to room temperature and the solvent was concentrated. The resulting resiude was subjected to a silica gel column chromatography (25 g of silica gel; dichloromethane-methanol (100:0–100:1–50:1–40:1–30:1–20:1) to give 439 mg of a crude product. This was suspended in ethyl acetate, collected by fitlration and washed with ethyl acetate and ether to give 396 mg of the desired free compound. This was converted into a hydrochloride by a conventional method to give 400 mg of the title compound. The yield was 54%.

NMR (400 MHz, [δ, $d_6$-DMSO); 0.91 (t, J=7.2 Hz, 3H),] δ, *DMSO-$d_6$); 0.91 (t, J=7.2 Hz, 3H),* 1.20–1.32 (m, 1H), 1.40–1.67 (m, 7H), 1.78–1.87 (m, 4H), [1.93 (t, J=7.1 Hz, 2H), 2.94 (dq, J=5.5,7.2 Hz, 2H), 4.25 (t, J=7.1 Hz, 2H),] *1.93 (t, J=7.1 Hz, 2H), 2.94 (dq, J=5.5,7.2 Hz, 2H), 4.25 (t, J=7.1 Hz, 2H),* 7.40–7.45 (m, 1H), 7.58–7.65 (m, 3H), [7.72 (t, J=5.5 Hz, 1H).] *7.72 (t, J=5.5 Hz, 1H).* FAB MS (m/z); 465 ($M^+$+1).

Similarly were prepared the compounds of Examples 69 and 204.

EXAMPLE 203

$N^1$-Ethyl-4-[amino-8-(3-fluorophenyl)-2-[2-(1-hydroxycyclohexyl)-1-ethynyl]-9H-9-purinyl] acetamide Hydrochloride NMR (400 MHz, [δ, $d_6$-DMSO); 0.96 (t, J=7.2 Hz, 3H),] δ, *DMSO-$d_6$); 0.96 (t, J=7.2 Hz, 3H),* 1.18–1.31 (m, 1H), 1.41–1.67 (m, 7H), 1.78–1.90 (m, 2H), [3.06 (dq, J=5.5,7.2 Hz, 2H),] *3.06 (dq, J=5.5,7.2 Hz, 2H),* 4.84 (s, 2H), 7.38–7.44 (m, 1H), 7.52–7.63 (m, 3H), [8.40 (t, J=5.5 Hz, 1H).] *8.40* (t, J=5.5 Hz, 1H). FAB MS; 437 ($M^+$+1).

EXAMPLE 204

4-[6-Amino-9-(3-fluorophenyl)-2-[2-(1-hydroxycyclohexyl)-1-ethynyl]-9H-9-purinyl] butaneamide Hydrochloride NMR (400 MHz, [δ, $d_6$-DMSO);] δ, *DMSO-$d_6$);* 1.19–1.33 (m, 1H), 1.40–1.70 (m, 9H), 1.79–1.91 (m, 4H), [1.97 (t, J=7.3 Hz, 2H), 4.25 (t, J=7.4 Hz, 2H),] *1.97 (t, J=7.3 Hz, 2H), 4.25 (t, J=7.4 Hz, 2H),* 6.74 (br s, 1H), 7.24 (br s, 1H), 7.40–7.46 (m, 1H), 7.59–7.68 (m, 3H). FAB MS; 437 ($M^+$+1).

EXAMPLE 205

$N^1$-Phenyl-4-[6-amino-8-(3-fluorophenyl)-2-[2-(1-hydroxycyclohexyl)-1-ethynyl]-9H-9-purinyl] butaneamide Hydrochloride NMR (400 MHz, [δ, $d_6$-DMSO);] δ, *DMSO-$d_6$);* 1.18–1.32 (m, 1H), 1.40–1.68 (m, 7H), 1.79–1.88 (m, 2H), 1.90–2.01 (m, 2H), [2.21 (t, J=7.2 Hz, 2H), 4.32 (t, J=7.2 Hz, 2H), 6.98 (t, J=7.6 Hz, 1H), 7.23 (t, J=7.6 Hz, 2H), 7.34–7.41 (m, 1H), 7.46 (d, J=7.6 Hz, 2H),] *2.21 (t, J=7.2 Hz, 2H), 4.32 (t, J=7.2 Hz, 2H), 6.98 (t, J=7.6 Hz, 1H), 7.23 (t, J=7.6 Hz, 2H)*5, *7.34–7.41 (m, 1H), 7.46 (d, J=7.6 Hz, 2H),* 7.54–7.59 (m, 1H), 7.64–7.67 (m, 2H), 9.82 (s, 1H). FAB MS; 513 ($M^+$+1).

EXAMPLE 206

1-{2-[8-(3-fluorophenyl)-9-methyl-9H-2-purinyl]-1-ethynyl}-1-cyclohexanol

A methanesulfonate (470 mg) prepared from 1-{2-[6-amino-8-(3-fluorophenyl)-9-methyl-9H-2-purinyl]-1-ethynyl}-1-cyclohexanol by a conventional method was dissolved in 25 ml of tetrahydrofuran, 0.44 ml of isoamyl nitride was added thereto and the mixture was heated under reflux for 1 hour. The reaction solution was concentrated to dryness and purified by a silica gel column (eluting with dichloromethane:methanol=95:5) to give 20 mg of the title compound.

NMR (400 MHz, [δ,] δ, *$CDCl_3$);* 1.26–1.39 (m, 1H), 1.50–1.82 (m, 7H), 2.04–2.15 (m, 2H), 7.26–7.33 (m, 1H), 7.50–7.65 (m, 3H), 9.08 (s, 1H). FAB MS; 351 ($M^+$+1).

EXAMPLE 207

8-(3-fluorophenyl)-2-[2-(1-hydroxycyclopentyl)-1-ethynyl]-9-methyl-9H-6-purinol

To 50 mg of 1-{2-[6-amino-8-(3-fluorophenyl)-9-methyl-9H-2-purinyl]-1-ethynyl}-1-cyclopentanol were added 3.0 ml of allyl alcohol and 1.0 ml of 5M NaOH, the mixture was stirred at room temperature for 10 minutes, 1.0 ml of THF was added thereto and the mixture was stirred again at room temperature for 15 hours and 40 minutes. The solvent was evaporated and then 200 ml of ethyl acetate and water (1:1) were added and an extraction was carried out. The aqueous lyaer was extracted with 100 ml of ethyl acetate again and the all organic layers were combined and washed with water and with brine once each. The organic layer was dried over anhydrous sodium sulfate and the solvent was evaporated. The resulting residue was purified by a p-TLC ($CH_2Cl_2$:MeOH=10:1), the resulting yellowish white crystals were suspended in diethyl ether and the suspenion was filtered to give 217 mg of the title compound as white crystals. The yield was 36%.

NMR (400 MHz, [δ, $d_6$-DMSO);] δ, *DMSO-$d_6$);* 1.68–1.81 (m, 4H), 1.92–2.00 (m, 4H), 3.82 (s, 3H), 5.62 (s, 1H) 7.39–7.43 (m, 1H), 7.60–7.71 (m, 3H), 12.86 (s, 1H).

EXAMPLE 208

1-[(E)-2-[6-Amino-8-(3-fluorophenyl)-9-methyl-9H-2-purinyl]-1-ethenyl}-1-cyclopentanol Hydrochloride A solution of 500 mg of 1-[(E)-2-[6-amino-8-(3-fluorophenyl)-9-methyl-9H-2-purinyl]-1-ethynyl]-1-cyclopentanol in 5 ml of tetrahydrofuran was added dropwise into a solution of 170 mg of lithium aluminum hydride in 10 ml of tetrahydrofuran at a temperature lower than 7° C. in a nitrogen atmosphere, followed by stirring for 30 minutes. Water (0.2 ml), 0.2 ml of 5N sodium hydroxide and 0.6 ml of water were added dropwise into the reaction mixture was ice-cooling to stop the reaction. The insoluble matters were filtered off, washed with ethyl acetate and the filtrate was concentrated. The resulting residue was subjected to a silica gel column chromatography (20 g of silica gel; dichloromethane-dichloromethane:methanol=40:1–20:1) and then to the same (20 g of NH silica gel; dichloromethane-dichloromethane:methanol=150:1–100:1–40:1) to give 160 mg of a free substance of 3. The resulting free compound was dissolved in methanol, five drops of 5N hydrochloric acid were added and the mixture was concentrated. The resulting residue was suspended in ether and the crystals were collected by filtration and washed with ether to give 108 mg of the title compound. The yield was 19%.

NMR (400 MHz, [δ, $d_6$-DMSO);] δ, *DMSO-$d_6$);* 1.64–1.92 (m, 8H), 3.90 (s, 3H), [6.70 (d, J=15.6 Hz, 1H),] *6.70 (d, J=15.6 Hz, 1H),* 7.46–7.52 (m, 1H), [7.51 (d, J=15.6 Hz, 1H),] *7.51 (d, J=15.6 Hz, 1H),* 7.65–7.71 (m, 1H), 7.73–7.80 (m, 2H). ESI MS; 354. m.p.; >290° C.

Similarly were prepared the compounds of Examples 209–212 using the corresponding materials.

EXAMPLE 209

1-[(E)-2-[6-Amino-9-ethyl-8-(3-fluorophenyl)-9H-2-purinyl]-1-ethenyl]-1-cyclobutanol Hydrochloride NMR (400 MHz, [δ, $d_6$-DMSO); 1.31 (t, J=7.2 Hz, 3H),] δ, *DMSO-$d_6$); 1.31 (t, J=7.2 Hz, 3H),* 1.72–1.85 (m, 2H), 2.15–2.30 (m, 4H), [4.38 (q, J=7.2 Hz, 2H), 6.64 (d, J=15.6 Hz, 1H),] *4.38 (q, J=7.2 Hz, 2H), 6.64 (d, J=15.6 Hz, 1H),* 7.47–7.53 (m, 1H), 7.64–7.74 (m, 4H). ESI MS; 354. m.p.; 178–180° C.

EXAMPLE 210

(E)-4-[6-Amino--9-ethyl-8-(3-fluorophenyl)-9H-2-purinyl]-2-methyl-3-buten-2-ol Hydrochloride NMR (400 MHz, [δ, $d_6$-DMSO); 1.30 (t, J=7.2 Hz, 3H),] δ, *DMSO-$d_6$); 1.30 (t, J=7.2 Hz, 3H),* 1.32 (s, 6H), [4.36 (q, J=7.2 Hz, 2H), 6.62 (d, J=15.6 Hz, 1H), 7.38 (d, J=15.6 Hz, 1H)] *4.36 (q, J=7.2 Hz, 2H), 6.62 (d, J=15.6 Hz, 1H), 7.38 (d, J=15.6 Hz, 1H),* 7.46–7.53 (m, 1H), 7.61–7.72 (m, 3H). ESI MS; 342.

EXAMPLE 211

(E)-4-[6-Amino-8-(3-fluorophenyl)-9-methyl-9H-2-purinyl]-2-methyl-3-buten-2-ol Hydrochloride NMR (400 MHz, [δ, $d_6$-DMSO);] δ, *DMSO-$d_6$);* 1.32 (s, 6H), 3.90 (s, 3H), [6.62 (d, J=16.0 Hz, 1H), 6.44 (d, J=16.0 Hz, 1H),] *6.62 (d, J=16.0 Hz, 1H), 6.44 (d, J=16.0 Hz, 1H),* 7.45–7.52 (m, 1H), 7.65–7.72 (m, 1H), 7.73–7.79 (m, 2H). ESI MS: 328. m.p.; >290° C.

EXAMPLE 212

(E)-1-[6-Amino-8-(3-fluorophenyl)-9-methyl-9H-2-purinyl]-ethyl-3-pente-1-ol Hydrochloride NMR (400 MHz, [δ, $d_6$-DMSO); 0.85 (t, J=7.2 Hz, 6H), 1.59 (q, J=7.2 Hz,4H),] δ, *DMSO-$d_6$); 0.85 (t, J=7.2 Hz, 6H), 1.59 (q, J=7.2 Hz,4H),* 3.90 (s, 3H), [6.62 (d, J=15.6 Hz, 1H), 7.32 (d, J=15.6 Hz, 1H),] *6.62 (d, J=15.6 Hz, 1H), 7.32 (d, J=15.6 Hz, 1H),* 7.45–7.52 (m, 1H), 7.64–7.71 (m, 1H), 7.72–7.79 (m, 2H). ESI MS; 356;

EXAMPLE 213

1-[(E) and (Z)-2-[6-Amino-8-(3-fluorophenyl)-9-methyl-9H-2-purinyl]-1-ethenyl]-1-cyclopentanol Hydrochloride 1) 1-[(E) and (Z)-2-(1,1,1-Tributylstannyl)-1-ethenyl]-1-cyclopentanols A mixture of 10 g of 1-ethynyl-1-cyclopentanol, 30 ml of tributyl in hydride and 190 mg of azobis (isobutyronitrile) was stirred in a nitrogen atmosphere at 90° C. for 3 hours. The reaction mixture was evaporated to give 27 g of a mixture of E- and Z-substances (E:Z=15:1) of b.p. 135° C. (0.2 mmHg).

NMR (400 MHz, [$CDCl_3$)δ;] δ, *$CDCl_3$);* 0.80–0.98 (m, 9H), 1.25–1.92 (m, 26H), [5.86 (d, J=13.2 Hz,] *5.86 (d, J=13.2 Hz,* ═CHSn of Z isomer), 6.14 (s, 2H, HC═CH of E isomer), [6.61 (d, J=13.2 Hz,] *6.61 (d, J=13.2 Hz,* ═CH of Z isomer).

2)-1-[(E) and (Z)-2-[6-Amino-8-(3-fluorophenyl)-9-methyl-9H-2-purinyl]-1-ethenyl]-1-cyclopentanol Hydrochloride The above prepared mixture (17.93 g) of 1-[(E) and (Z)-2-(1,1,1-tributylstannyl)-1-ethynyl]-1-cyclopentanols, 11 g of 8-(3-fluorophenyl)-2-iodod-9-methyl-9H-6-purinamine, 8.25 g of tetrabutylammonium chloride and 671 mg of palladium acetate were suspended in 165 ml of toluene and the suspension was stirred in a nitrogen atmosphere at 90° C. for 3.5 hours. The reaction mixture was diluted with 165 ml of ethyl acetate and washed with a saturated ammonium chloride solution and brine. The organic layer was dried over anhydrous magneisum sulfate and then concentrated. The resulting residue was subjected to a silica gel column chromatography (350 g of silica gel; hexane, hexane:ethyl acetate (4:1, 1:1, 1:2 and 1:4) and ethyl acetate) and then the resulting crystals were washed with ethyl acetate/hexane to give 6.6 g of crude 1-[(E)-2-[6-amino-8-(3-fluorophenyl)-9-methyl-9H-2-purinyl]-1-ethenyl]-1-cyclopentanol. This was suspended in 70 ml of methanol, dissolved by addition of 7 ml of 5N hydrochloric acid and the solution was concentrated. After suspending with ether/ethyl acetate, the crystals were collected by filtration, washed with ether and air-dried at 60° C. for 10 hours to give 5.92 g (51% yield) of 1-[(E)-2-[6-amino-8-(3-fluorophenyl)-9-methyl-9H-2-purinyl]-1-ethenyl]-1-cyclopentanol hydrochloride which was the same as that obtained in Example 208. NMR and MS were the same as those mentioned above.

The filtrate was concentrated and re-purified to give 450 mg (4% yield) of 1-[(Z)-2-[6-amino-8-(3-fluorophenyl)-9-methyl-9H-2-purinyl]-1-ethenyl]-1-cyclopentanol hydrochloride.

NMR (400 MHz, [δ, $d_6$-DMSO);] δ, *DMSO-$d_6$);* 1.62–1.88 (m, 6H), 1.90–2.03 (m, 2H), 3.86 (s, 3H), [6.35 (d, J=13.2 Hz, 1H), 6.44 (d, J=13.2 Hz, 1H),] *6.35 (d, J=13.2 Hz, 1H), 6.44 (d, J=13.2 Hz, 1H),* 7.44–7.52 (m, 1H), 7.64–7.72 (m, 1H), 7.72–7.78 (m, 2H). ESI MS; 354.

Similarly were synthesized the compounds of Examples 214 to 227.

EXAMPLE 214

1[(E)-2-[6-Amino-9-ethyl-8-(3-fluorophenyl)-9H-2-purinyl]-1-ethenyl]-1-cyclopentanol Hydrochloride NMR (400 MHz, [δ, $d_6$-DMSO); 1.30 (t, J=7.2 Hz, 3H),] δ, *DMSO-$d_6$); 1.30 (t, J=7.2 Hz, 3H),* 1.64–1.90 (m, 8H), [4.36 (q, J=7.2 Hz, 2H), 6.69 (d, J=15.6 Hz, 1H), 7.47 (d, J=15.6 Hz, 1H),] *4.36 (q, J=7.2 Hz, 2H), 6.69 (d, J=15.6 Hz, 1H), 7.47 (d, J=15.6 Hz, 1H),* 7.47–7.53 (m, 1H), 7.65–7.71 (m, 3H). ESI MS; 368.

EXAMPLE 215

1-[(E)-[6-Amino-8-(3-fluorophenyl)-9-methyl-9H-2-purinyl]-1-ethenyl]-1-cyclobutanol Hydrochloride NMR (400 MHz, [δ, $d_6$-DMSO);] δ, *DMSO-$d_6$);* 1.73–1.84 (m, 2H), 2.14–2.32 (m, 4H), 3.92 (s, 3H), [6.64 (d, J=16.0 Hz, 1H),] *6.64 (d, J=16.0 Hz, 1H),* 7.46–7.52 (m, 1H), 7.65–7.72 (m, 1H), [7.73 (d, J=16.0 Hz, 1H),] *7.73 (d, J–16.0 Hz, 1H),* 7.74–7.80 (m, 2H). ESI MS; 340. m.p.; 181–184° C.

EXAMPLE 216

1-[(E)-2-[6-Amino-8-(3-fluorophenyl)-9-methyl-9H-2-purinyl]-1-ethenyl]-1-cyclohexanol Hydrochloride NMR (400 MHz, [δ, $d_6$-DMSO);] δ, *DMSO-$d_6$);* 1.22–1.36 (m, 1H), 1.46–1.74 (m, 9H), 3.90 (s, 3H), [6.65 (d, J=15.6 Hz, 1H), 7.44–7.52 (m, 1H), 7.48 (d, J=15.6 Hz, 1H),] *6.65 (d, J=15.6 Hz, 1H), 7.44–7.52 (m, 1H), 7.48 (d, J=15.6 Hz, 1H),* 7.64–7.71 (m, 1H), 7.73–7.79 (m, 2H). ESI MS; 368. m.p.; 222–225° C.

EXAMPLE 217

1-[(E)-2-[6-Amino-9-ethyl-8-(3-fluorophenyl)-9H-2-purinyl]-1-ethynyl]-1-cyclohexanol Hydrochloride NMR (400 MHz, [δ, $d_6$-DMSO); 1.31 (t, J=7.2 Hz, 3H),] δ, *DMSO-$d_6$); 1.31 (t, J=7.2 Hz, 3H),* 1.47–1.72 (m, 10H),

[4.37 (q, J=7.2 Hz, 2H), 6.65 (d, J=16.0 Hz, 1H), 7.47–7.54 (m, 1H), 7.59 (d, J=16.0 Hz, 1H),] *4.37 (q, J=7.2 Hz, 2H), 6.65 (d, J=16.0 Hz, 1H), 7.47–7.54 (m, 1H), 7.59 (d, J=16.0 Hz, 1H),* 7.65–7.72 (m, 3H). ESI MS; 382.

EXAMPLE 218

(E)-1-[6-Amino-9-ethyl-8-(3-fluorophenyl)-9H-2-purinyl]-3-ethyl-3-penten-3-ol Hydrochloride NMR (400 MHz, [δ, $d_6$-DMSO); 0.85 (t, J=7.2 Hz, 6H), 1.30 (t, J=7.2 Hz, 3H), 1.58 (q, J=7.2 Hz,4H), 4.36 (q, J=7.2 Hz, 2H), 6.62 (d, J=16.0 Hz, 1H), 7.30 (d, J=16.0 Hz, 1H),] δ, *DMSO-$d_6$); 0.85 (t, J=7.2 Hz, 6H), 1.30 (t, J=7.2 Hz, 3H), 1.58 (q, J=7.2 Hz,4H), 4.36 (q, J=7.2 Hz, 2H), 6.62 (d, J=16.0 Hz, 1H), 7.30 (d, J=16.0 Hz, 1H),* 7.47–7.53 (m, 1H), 7.64–7.72 (m, 3H ). ESI MS; 370.

EXAMPLE 219

(E)-4-[6-Amino-8-(3-fluorophenyl)-9-phenyl-9H-2-purinyl]-2-methyl-3-buten-2-ol Hydrochloride NMR (400 MHz, [δ, $d_6$-DMSO);] δ, *DMSO-$d_6$);* 1.26 (s, 6H), [6.50 (d, J=16.0 Hz, 1H), 7.19 (d, J=16.0 Hz, 1H),] *6.50 (d, J=16.0 Hz, 1H), 7.19 (d, J=16.0 Hz, 1H),* 7.22–7.35 (m, 3H), 7.42–7.51 (m, 3H), 7.56–7.62 (m, 3H). ESI MS; 390.

EXAMPLE 220

1-[(E)-2-[6-Amino-8-(3-fluorophenyl)-9-propyl-9H-2-purinyl]-1-ethenyl]-1-cyclobutanol Hydrochloride NMR (400 MHz, [δ, $d_6$-DMSO); 0.74 (t, J=7.2 Hz, 3H), 1.66 (sex, J=7.2 Hz, 2H),] δ, *DMSO-$d_6$); 0.74 (t, J=7.2 Hz, 3H), 1.66 (sex, J=7.2 Hz, 2H),* 1.71–1.85 (m, 2H), 2.14–2.30 (m, 4H), [4.33 (t, J=7.2 Hz, 2H), 6.64 (d, J=16.0 Hz, 1H),] *4.33 (t, J=7.2 Hz, 2H), 6.64 (d, J=16.0 Hz, 1H),* 7.46–7.53 (m, 1H), 7.64–7.74 (m, 4H). ESI MS; 368.

EXAMPLE 221

1-[(E)-2-[6-Amino-8-(3-fluorophenyl)-9-propyl-9H-2-purinyl]-1-ethenyl]-1-cyclopentanol Hydrochloride NMR (400 MHz, [δ, $d_6$-DMSO); 0.74 (t, J=7.2 Hz, 3H),] δ, *DMSO-$d_6$); 0.74 (t, J=7.2 Hz, 3H),* 1.60–1.93 (m, 10H), [4.32 (t, J=7.2 Hz, 2H), 6.69 (d, J=15.6 Hz, 1H),] *4.32 (t, J=7.2 Hz, 2H), 6.69 (d, J=15.6 Hz, 1H),* 7.46–7.54 (m, 1H), [7.50 (d, J=15.6 Hz, 1H),] *7.50 (d, J=15.6 Hz, 1H),* 7.64–7.72 (m, 3H). ESI MS; 382.

EXAMPLE 222

1-[(E)-2-[6-Amino-8-(3-fluorophenyl)-9-propyl-9H-2-purinyl]-1-ethenyl]-1-cyclopentanol Hydrochloride NMR (400 MHz, [δ, $d_6$-DMSO); 0.74 (t, J=7.2 Hz, 3H),] δ, *DMSO-$d_6$); 0.74 (t, J=7.2 Hz, 3H),* 1.23–1.37 (m, 1H), 1.47–1.60 (m, 9H), 1.66 (sex, 2H), [4.32 (t, J=7.2 Hz, 2H), 6.65 (d, J=16.0 Hz, 1H), 7.46–7.52 (m, 1H), 7.54 (d, J=16.0 Hz, 1H),] *4.32 (t, J=7.2 Hz, 2H), 6.65 (d, J=16.0 Hz, 1H), 7.46–7.52 (m, 1H), 7.54 (d, J=16.0 Hz, 1H),* 7.66–7.72 (m, 3H). ESI MS; 396.

EXAMPLE 223

(E)-4-[6-Amino-8-(3-fluorophenyl)-9-propyl-9H-2-purinyl]-2-methyl-3-buten-2-ol Hydrochloride NMR (400 MHz, [δ, $d_6$-DMSO); 0.74 (t, J=7.2 Hz, 3H),] δ, *DMSO-$d_6$); 0.74 (t, J=7.2 Hz, 3H),* 1.32 (s, 6H), [1.66 (sex, J=7.2 Hz, 2H), 4.33 (t, J=7.2 Hz, 2H), 6.62 (d, J=15.6 Hz, 1H), 7.43 (d, J=15.6 Hz, 1H),] *1.66 (sex, J=7.2 Hz, 2H), 4.33 (t, J=7.2 Hz, 2H), 6.62 (d, J=15.6 Hz, 1H), 7.43 (d, J=15.6 Hz, 1H),* 7.46–7.53 (m, 1H), 7.65–7.72 (m, 3H). ESI MS; 356.

EXAMPLE 224

(E)-1-[6-Amino-8-(3-fluorophenyl)-9-propyl-9H-2-purinyl]-3-ethyl-3-penten-3-ol Hydrochloride NMR (400 MHz, [δ, $d_6$-DMSO); 0.73 (t, J=7.2 Hz, 3H), 0.85 (t, J=7.2 Hz, 6H), 1.58 (q, J=7.2 Hz,4H), 1.66 (sex, J=7.2 Hz, 2H), 4.32 (t, J=7.2 Hz, 2H), 6.61 (d, J=15.6 Hz, 1H), 7.29 (d, J=15.6 Hz, 1H),] δ, *DMSO-$d_6$); 0.73 (t, J=7.2 Hz, 3H), 0.85 (t, J=7.2 Hz, 6H), 1.58 (q, J=7.2 Hz,4H), 1.66 (sex, J=7.2 Hz, 2H), 4.32 (t, J=7.2 Hz, 2H), 6.61 (d, J=15.6 Hz, 1H), 7.29 (d, J=15.6 Hz, 1H),* 7.45–7.52 (m, 1H), 7.64–7.72 (m, 3H ). ESI MS; 384.

EXAMPLE 225

1-[(E)-2-[6-Amino-9-cyclopropyl-8-(3-fluorophenyl)-9H-2-purinyl]-1-ethynyl]-cyclobutanol Hydrochloride NMR (400 MHz, [δ, $d_6$-DMSO);] δ, *DMSO-$d_6$);* 0.77–0.84 (m, 2H), 1.08–1.16 (m, 2H), 1.72–1.86 (m, 2H), 2.14–2.32 (m, 4H), 3.78–3.84 (m, 1H), [6.64 (d, J=15.6 Hz, 1H),] *6.64 (d, J=15.6 Hz, 1H),* 7.44–7.51 (m, 1H), 7.62–7.70 (m, 1H), [7.70 (d, J=15.6 Hz, 1H),] *7.70 (d, J=15.6* Hz, 1H), 7.81–7.89 (m, 2H). ESI MS; 366.

EXAMPLE 226

1-[(E)-2-[6-Amino-9-cyclopropyl-8-(3-fluorophenyl)-9H-2-purinyl-1-ethenyl]-1-cyclopentanol Hydrochloride NMR (400 MHz, [δ, $d_6$-DMSO);] δ, *DMSO-$d_6$);* 0.77–0.83 (m, 2H), 1.07–1.14 (m, 2H), 1.65–1.93 (m, 8H), [3.80 (sept, J=3.6 Hz, 1H), 6.70 (d, J=15.6 Hz, 1H), 7.44–7.50 (m, 1H), 7.50 (d, J=15.6 Hz, 1H),] *3.80 (sept, J=3.6 Hz, 1H), 6.70 (d, J=15.6 Hz, 1H), 7.44–7.50 (m, 1H), 7.50 (d, J=15.6 Hz, 1H),* 7.63–7.70 (m, 1H), 7.81–7.88 (m, 2H). ESI MS; 380.

EXAMPLE 227

(E)-4-[6-Amino-9-cyclopropyl-8-(3-fluorophenyl)-9H-2-purinyl]-2-methyl-3-buten-2-ol Hydrochloride NMR (400 MHz, [δ, $d_6$-DMSO);] δ, *DMSO-$d_6$);* 0.77–0.84 (m, 2H), 1.07–1.55 (m, 2H), 1.33 (s, 6H), [3.80 (sept, J=3.6 Hz, 1H), 6.63 (d, J=16.0 Hz, 1H), 7.41 (d, J=16.0 Hz, 1H),] *3.80 (sept, J=3.6 Hz, 1H), 6.63 (d, J=16.0 Hz, 1H), 7.41 (d, J=16.0 Hz, 1H),* 7.44–7.51 (m, 1H), 7.62–7.70 (m, 1H), 7.80–7.88 (m, 2H). ESI MS; 354.

EXAMPLE 228

(Z)-4-[6-Amino-9-ethyl-8-(3-fluorophenyl)-9H-2-purinyl]-2-methyl-3-buten-2-ol Hydrochloride To a solution of 200 mg of 4-[6-amino-9-ethyl-8-(3-fluorophenyl)-9H-2-purinyl]-2-methyl-3-butyn-2-ol in 20 ml of methanol were added 5 μl of quinoline and 20 mg of 10% palladium/barium carbonate and the mixture was stirred in a hydrogen atmosphere at room temperature for 10 minutes. The palladium/barium carbonate was filtered off and the filtrate was concentrated and then the resulting residue was subjected to a silica gel column chromatography (15 g of silica gel; dichloromethane-dichloromethane/methanol=60:1–40:1) to give (Z)-4-[6-amino-9-ethyl-8-(3-fluorophenyl)-9H-2-purinyl]-2-methyl-3-buten-2-ol. This was dissolved in methanol and five drops of 5N hydrochloric acid were added thereto followed by concentrating. Ethyl acetate and ether were added to the resulting residue and the crystals were collected by filtration and washed with ether to give 851 mg of the product. The yield was 26%.

NMR (400 MHz, [δ, $d_6$-DMSO); 1.33 (t, J=7.2 Hz, 3H),] δ, *DMSO-$d_6$*); *1.33 (t, J=7.2 Hz, 3H)*, 1.45 (s, 6H), [4.31 (q, J=7.2 Hz, 2H), 6.33 (d, J=13.4 Hz, 1H), 6.40 (d, J=13.4 Hz, 1H),] *4.31 (q, J=7.2 Hz, 2H), 6.33 (d, J=13.4 Hz, 1H), 6.40 (d, J=13.4 Hz, 1H)*, 7.47–7.54 (m, 1H), 7.64–7.72 (m, 3H). ESI MS; 342.

EXAMPLE 229

1-2-[6-Amino-8-(3-fluorophenyl)-9-methyl-9H-2-purinyl]-1-ethyl]-1-cyclopentanol Hydrochloride To a solution of 300 mg of 1-[2-[6-amino-8-(3-fluorophenyl)-9-methyl-9H-2-purinyl]-1-ethynyl]-1-cyclopentanol in 20 ml of methanol were added six drops of 5N hydrochloric acid and 63 mg of 10% palladium/carbon and the mixture was stirred in a hydrogen atmosphere at room temperature for 17 hours. The palladium/carbon was filtered off, the filtrate was concentrated and the residue was dissolved in ethyl acetate and saturated sodium hydrogen carbonate. The organic layer was washed with brine, dried over anhydrous sodium sulfate and concentrated. The resulting residue was subjected to a silica gel column chromatography (15 g of silica gel; dichloromethane, dichloromethane/methanol (40:1, 20:1 and 10:1) to give 1-[2-[6-amino-8-(3-fluorophenyl)-9-methyl-9H-2-purinyl]-1-ethyl]-1-cyclopentanol. This was dissolved in methanol and then five drops of 5N hydrochloric acid were added thereto followed by concentrating. Ether was added to the residue and the crystals were collected by filtration and washed with ether to give [6209] *209* mg of the product. The yield was 69%.

NMR (400 MHz, [δ, $d_6$-DMSO);] δ, *DMSO-$d_6$*); 1.45–1.80 (m, 8H), [2.02 (t, J=8.0 Hz, 2H), 3.00 (t, J=8.0 Hz, 2H),] *2.02 (t, J=8.0 Hz, 2H), 3.00 (t, J=8.0 Hz, 2H)*, 3.88 (s, 3H), 7.45–7.52 (m, 1H), 7.64–7.71 (m, 1H), 7.72–7.78 (m, 2H). ESI MS; 356.

Similarly were synthesized the compounds of Examples 230 to 237.

EXAMPLE 230

1-[2-[6-Amino-8-(3-fluorophenyl)-9-methyl-9H-2-purinyl]-1-ethyl]-1-cyclobutanol Hydrochloride NMR (400 MHz, [δ, $d_6$-DMSO);] δ, *DMSO-$d_6$*); 1.45–1.58 (m, 1H), 1.60–1.70 (m, 1H), [2.00 (dd, J=6.8 and 8.8 Hz, 4H), 2.06 (t, J=8.0 Hz, 2H), 2.93 (t, J=8.0 Hz, 2H),] *2.00 (dd, J=6.8 and 8.8 Hz, 4H), 2.06 (t, J=8.0 Hz, 2H), 2.93 (t, J=8.0 Hz, 2H)*, 3.89 (s, 3H), 7.45–7.52 (m, 1H), 7.64–7.71 (m, 1H), 7.72–7.78 (m, 2H). ESI MS; 342.

EXAMPLE 231

1-[6-Amino-8-(3-fluorophenyl)-9-methyl-9H-2-purinyl]-3-ethyl-3-pentanol Hydrochloride NMR (400 MHz, [δ, $d_6$-DMSO); 0.84 (t, J=7.2 Hz, 6H), 1.42 (q, J=7.2 Hz, 4H),] δ, *DMSO-$d_6$*); *0.84 (t, J=7.2 Hz, 6H), 1.42 (q, J=7.2 Hz, 4H)*, 1.82–1.92 (m, 2H), 2.84–2.94 (m, 2H), 3.88 (s, 3H), 7.45–7.52 (m, 1H), 7.64–7.71 (m, 1H), 7.72–7.77 (m, 2H). ESI MS; 358.

EXAMPLE 232

1-[2-[6-Amino-9-ethyl-8-(3-fluorophenyl)-9H-2-purinyl]-1-ethyl]-1-cyclobutanol Hydrochloride NMR (400 MHz, [δ, $d_6$-DMSO); 1.29 (t, J=7.2 Hz, 3H),] δ, *DMSO-$d_6$*); *1.29 (t, J=7.2 Hz, 3H)*, 1.44–1.57 (m, 1H), 1.58–1.72 (m, 1H), [1.99 (dd, J=6.8 and 8.8 Hz, 4H), 2.05 (t, J=8.0 Hz, 2H), 2.93 (t, J=8.0 Hz, 2H), 4.34 (q, J=7.2 Hz, 2H),] *1.99 (dd, J=6.8 and 8.8 Hz, 4H), 2.05 (t, J=8.0 Hz, 2H), 2.93 (t, J=8.0 Hz, 2H), 4.34 (q, J=7.2 Hz, 2H)*, 7.47–7.53 (m, 1H), 7.64–7.72 (m, 3H). ESI MS; 356.

EXAMPLE 233

1-[2-[6-Amino-9-ethyl-8-(3-fluorophenyl)-9H-purinyl]-1-ethyl]-1-cyclopentanol Hydrochloride NMR (400 MHz, [δ, $d_6$-DMSO); 1.29 (t, J=7.2 Hz, 3H), 1.42–1.81 (m, 8H), 2.03 (t, J=8.0 Hz, 2H), 3.00 (t, J=8.0 Hz, 2H), 4.34 (q, J=7.2 Hz, 2H),] δ, *DMSO-$d_6$*); *1.29 (t, J=7.2 Hz, 3H), 1.42–1.81 (m, 8H), 2.03 (t, J=8.0 Hz, 2H), 3.00 (t, J=8.0 Hz, 2H), 4.34 (q, J=7.2 Hz, 2H)*, 7.47–7.53 (m, 1H), 7.63–7.72 (m, 3H). ESI MS; 370.

EXAMPLE 234

4-[6-Amino-9-ethyl-8-(3-fluorophenyl)-9H-2-purinyl]-2-methyl-2-butanol Hydrochloride NMR (400 MHz, [δ, $d_6$-DMSO);] δ, *DMSO-$d_6$*); 1.17 (s, 6H), [1.29 (t, J=7.2 Hz, 3H), 1.91 (t, J=8.0 Hz, 2H), 2.95 (t, J=8.0 Hz, 2H), 4.33 (q, J=7.2 Hz, 2H),] *1.29 (t, J=7.2 Hz, 3H), 1.91 (t, J=8.0 Hz, 2H), 2.95 (t, J=8.0 Hz, 2H), 4.33 (q, J=7.2 Hz, 2H)*, 7.47–7.53 (m, 1H), 7.64–7.72 (m, 3H). ESI MS; 344.

EXAMPLE 235

1-[6-Amino-9-ethyl-8-(3-fluorophenyl)-9-2-purinyl]-3-ethyl]-3-pentanol Hydrochloride NMR (400 MHz, [δ, $d_6$-DMSO); 0.83 (t, J=7.2 Hz, 6H), 1.30 (t, J=7.2 Hz, 3H), 1.42 (q, J=7.2 Hz, 4H),] δ, *DMSO-$d_6$*); *0.83 (t, J=7.2 Hz, 6H), 1.30 (t, J=7.2 Hz, 3H), 1.42 (q, J=7.2 Hz, 4H)*, 1.83–1.92 (m, 2H), 2.84–2.95 (m, 2H), [4.34 (q, J=7.2 Hz, 2H),] *4.34 (q, J=7.2 Hz, 2H)*, 7.47–7.53 (m, 1H), 7.64–7.72 (m, 3H). ESI MS; 372.

EXAMPLE 236

4-[6-Amino-8-(3-fluorophenyl)-9-propyl-9H-2-purinyl]2-methyl-2-butanol Hydrochloride NMR (400 MHz, [δ, $d_6$-DMSO); 0.72 (t, J=7.2 Hz, 3H),] δ, *DMSO-$d_6$*); *0.72 (t, J=7.2 Hz, 3H)*, 1.17 (s, 6H), [1.64 (sex, J=7.2 Hz, 3H), 1.91 (t, J=8.0 Hz, 2H), 2.95 (t, J=8.0 Hz, 2H), 4.30 (t, J=7.2 Hz, 2H),] *1.64 (sex, J=7.2 Hz, 3H), 1.91 (t, J=8.0 Hz, 2H), 2.95 (t, J=8.0 Hz, 2H), 4.30 (t, J=7.2 Hz, 2H)*, 7.46–7.53 (m, 1H), 7.64–7.72 (m, 3H). ESI MS; 358.

EXAMPLE 237

4-[6-Amino-9-[4-(dimethylamino)phenyl]-8-(3-fluoro-phenyl)-9H-2-purinyl]-2-methyl-2-butanol Dihydrochloride NMR (400 MHz, [δ, $d_6$-DMSO);] δ, *DMSO-$d_6$*); 1.12 (s, 6H), 1.76–1.82 (m, 2H), 2.82–2.90 (m, 2H), 3.00 (s, 6H),

[6.89 (d, J=8.8 Hz, 2H), 7.25 (d, J=8.8 Hz, 2H),] *6.89 (d, J=8.8 Hz, 2H), 7.25 (d, J=8.8 Hz, 2H)*, 7.27–7.37 (m, 3H), 7.44–7.51 (m, 1H). ESI MS; 435.
Structural formulae of the compounds of the above Examples are shown in Table 3.
TABLE 3
| Ex. No. | Structural Formula |
|---|---|
| 1 | 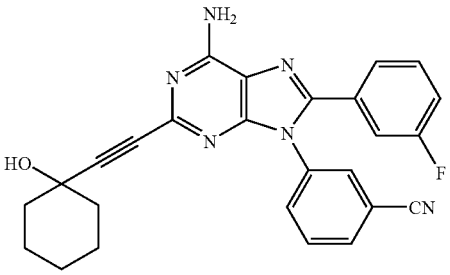 |
| 2 | 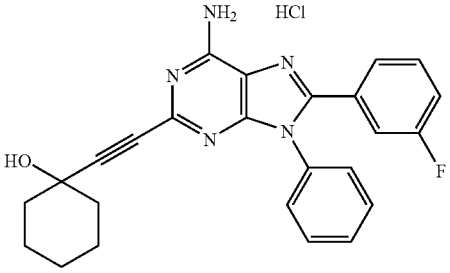 |
| 3 | 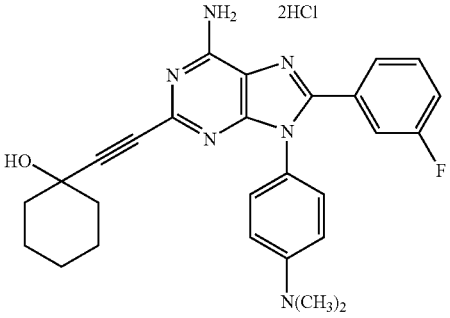 |
| 4 | 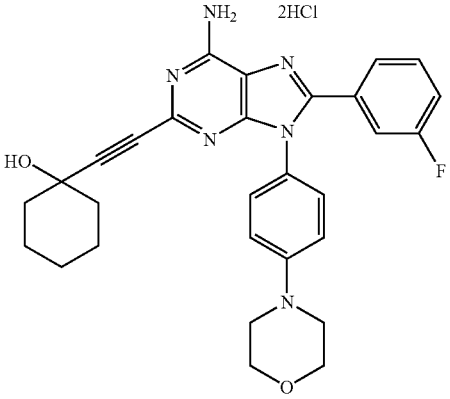 |
TABLE 3-continued
| Ex. No. | Structural Formula |
|---|---|
| 5 | 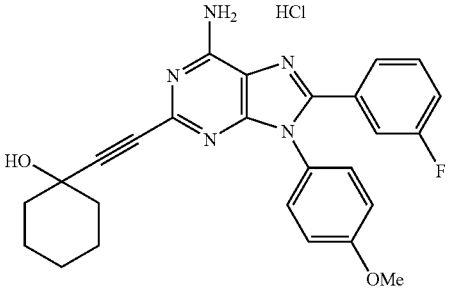 |
| 6 | 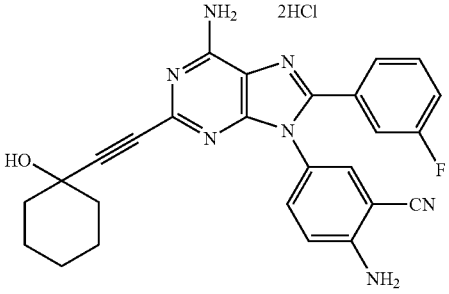 |
| 7 | 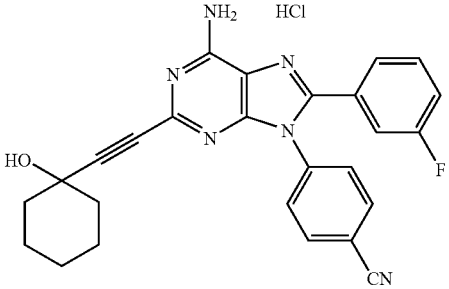 |
| 8 | 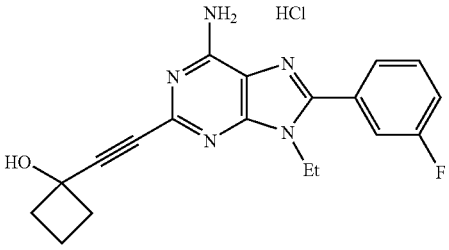 |
| 9 | 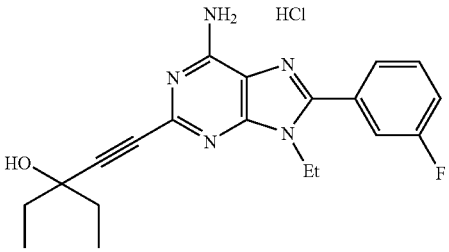 |

TABLE 3-continued
| Ex. No. | Structural Formula |
|---|---|
| 10 | 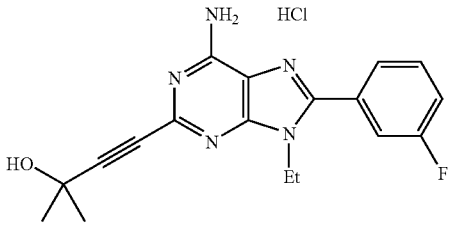 |
| 11 | 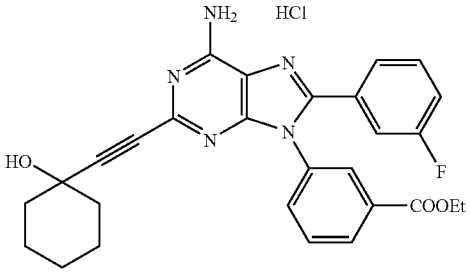 |
| 12 | 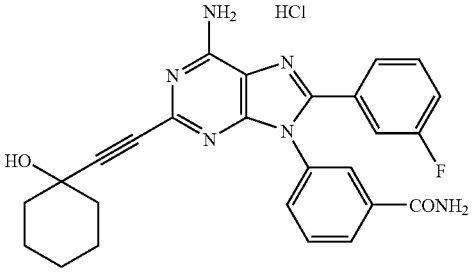 |
| 13 | 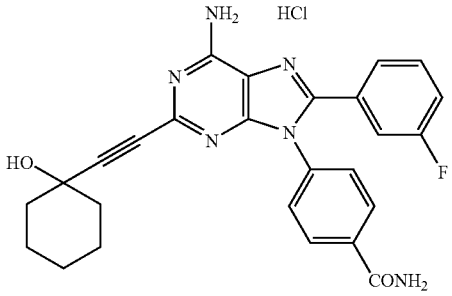 |
| 14 | 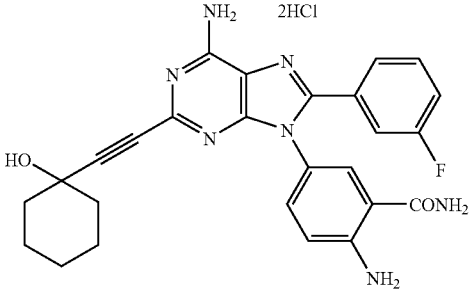 |
TABLE 3-continued
| Ex. No. | Structural Formula |
|---|---|
| 15 | 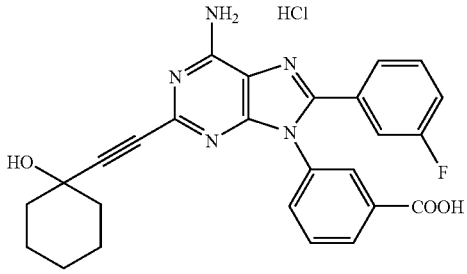 |
| 16 | 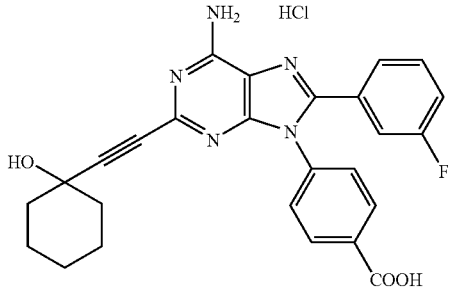 |
| 17 | 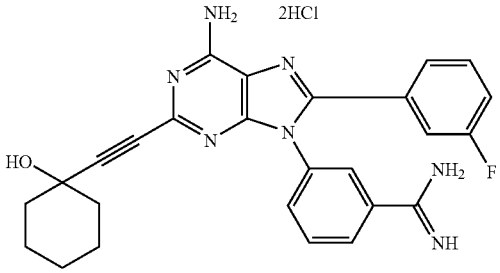 |
| 18 | 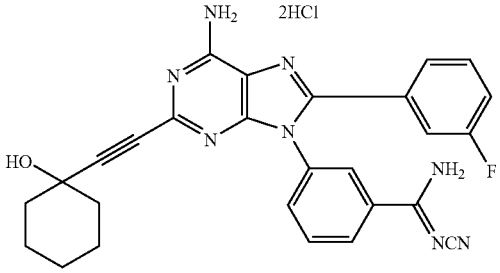 |
| 19 | 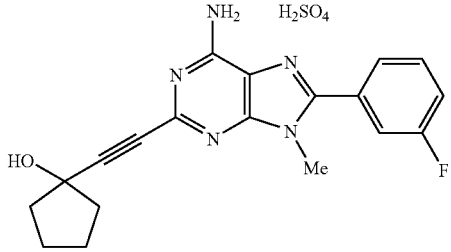 |

TABLE 3-continued
| Ex. No. | Structural Formula |
|---|---|
| 20 | 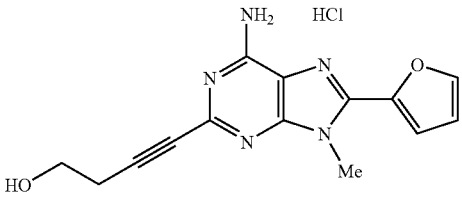 |
| 21 | 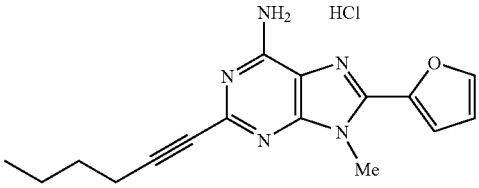 |
| 22 | 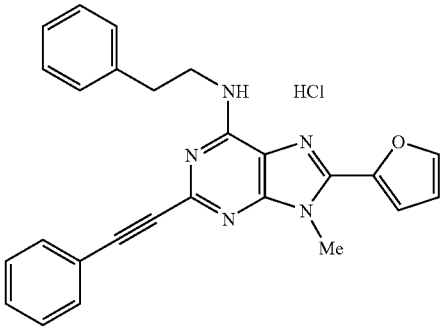 |
| 23 | 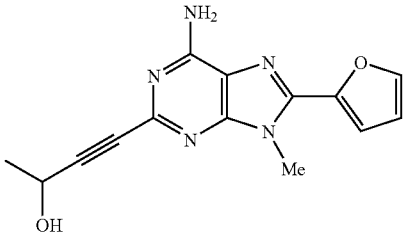 |
| 24 | 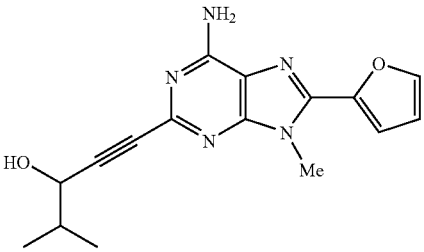 |
| 25 | 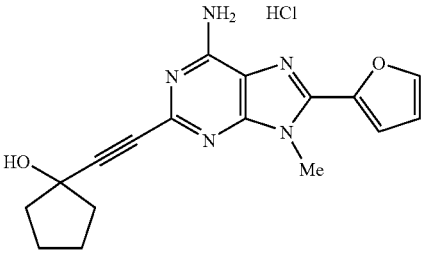 |
TABLE 3-continued
| Ex. No. | Structural Formula |
|---|---|
| 26 | 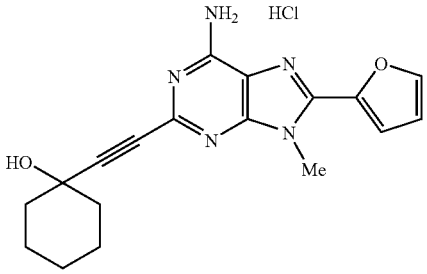 |
| 27 | 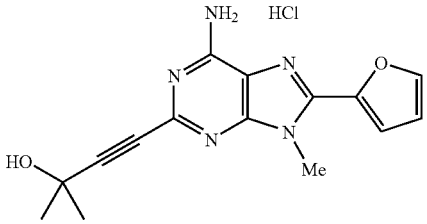 |
| 28 | 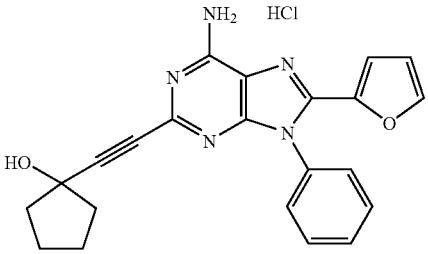 |
| 29 | 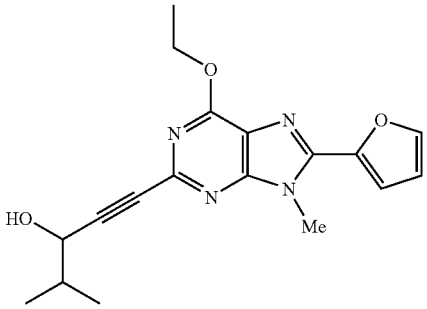 |
| 30 | 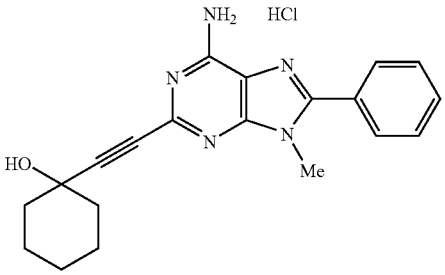 |

TABLE 3-continued
| Ex. No. | Structural Formula |
|---|---|
| 31 | 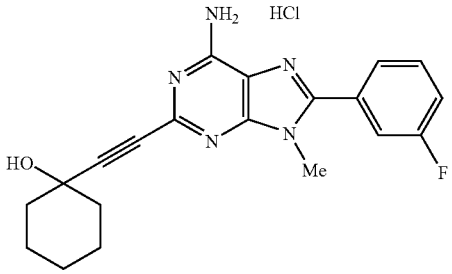 |
| 32 | 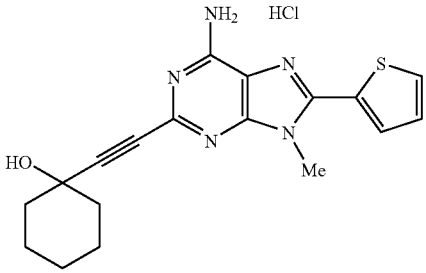 |
| 33 | 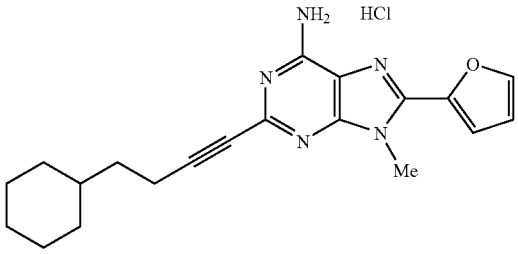 |
| 34 | 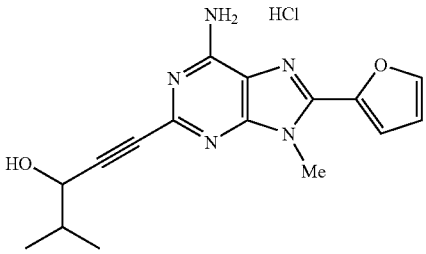 |
| 35 | 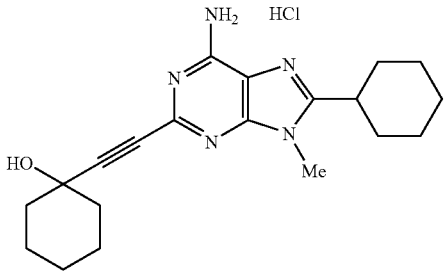 |
TABLE 3-continued
| Ex. No. | Structural Formula |
|---|---|
| 36 | 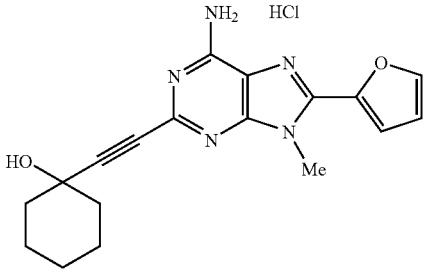 |
| 37 | 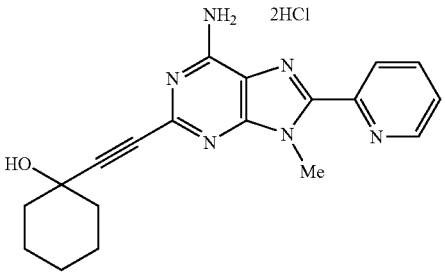 |
| 38 | 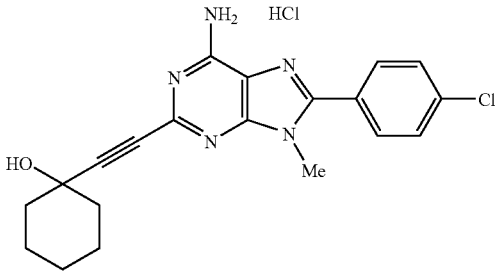 |
| 39 | 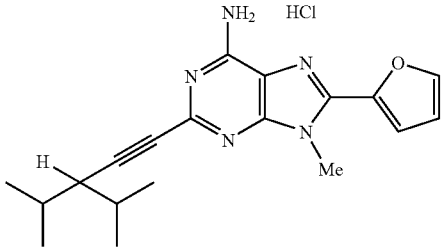 |
| 40 | 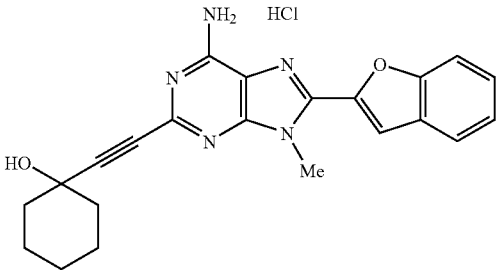 |

TABLE 3-continued
| Ex. No. | Structural Formula |
|---|---|
| 41 | 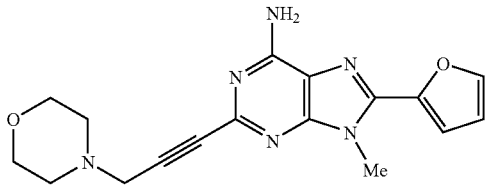 |
| 42 | 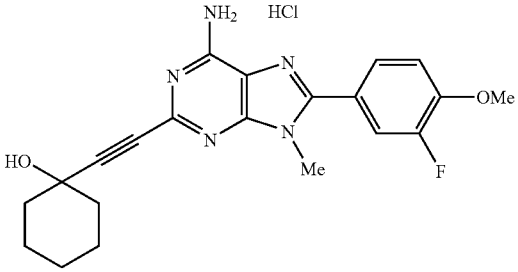 |
| 43 | 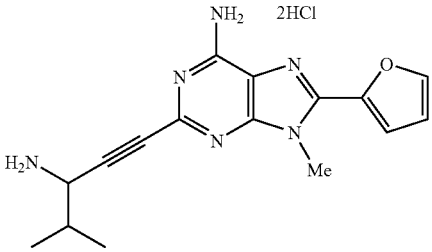 |
| 44 | 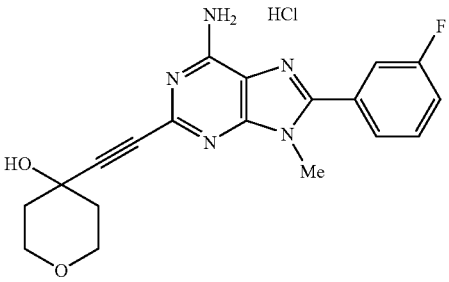 |
| 45 | 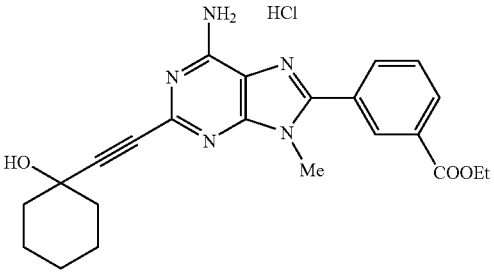 |
TABLE 3-continued
| Ex. No. | Structural Formula |
|---|---|
| 46 | 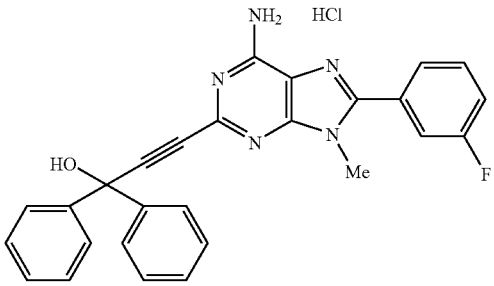 |
| 47 | 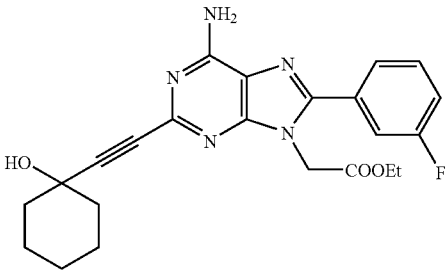 |
| 48 | 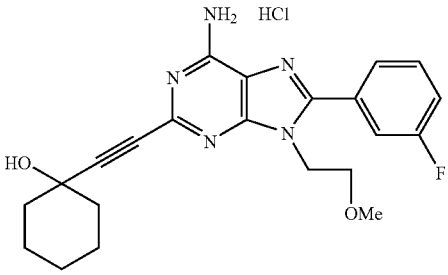 |
| 49 | 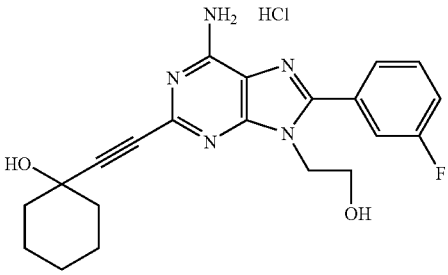 |
| 50 | 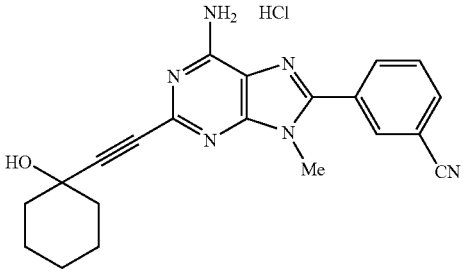 |

TABLE 3-continued
| Ex. No. | Structural Formula |
|---|---|
| 51 | 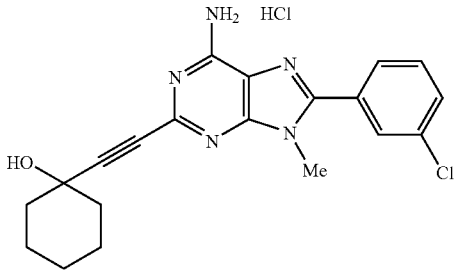 |
| 52 | 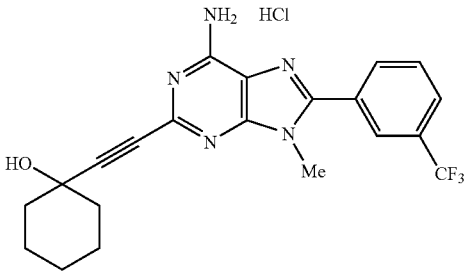 |
| 53 | 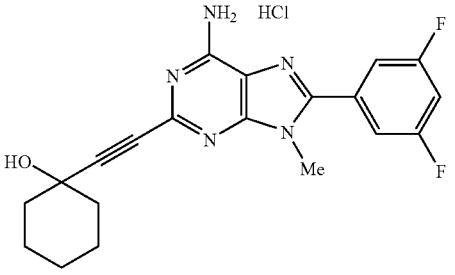 |
| 54 | 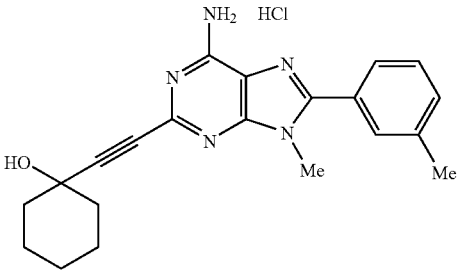 |
| 55 | 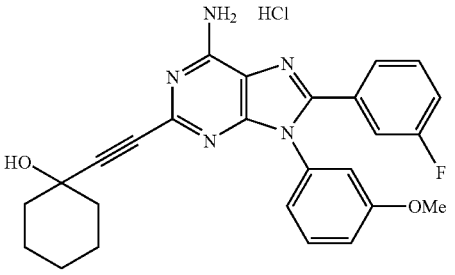 |
TABLE 3-continued
| Ex. No. | Structural Formula |
|---|---|
| 56 | 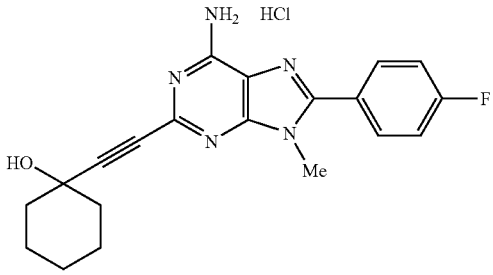 |
| 57 | 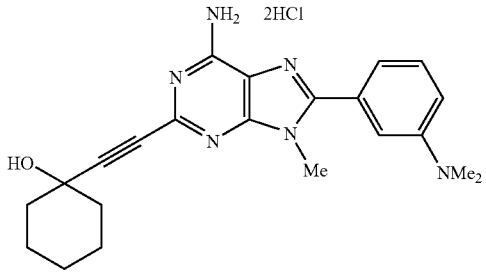 |
| 58 | 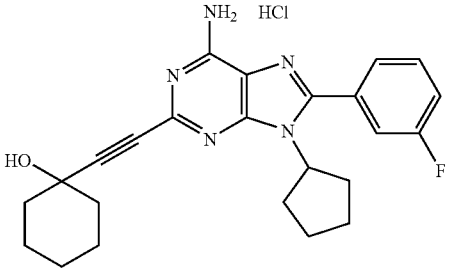 |
| 59 | 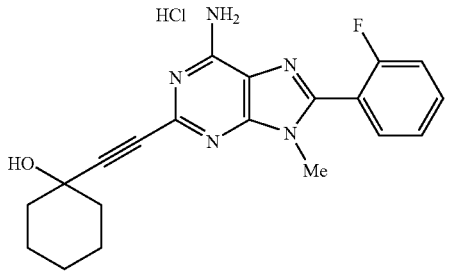 |
| 60 | 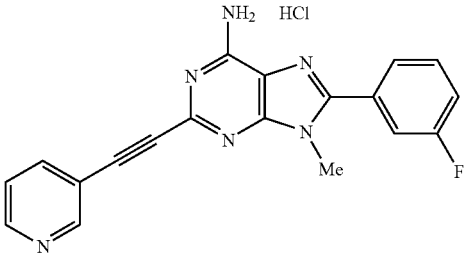 |

TABLE 3-continued
| Ex. No. | Structural Formula |
|---|---|
| 61 | 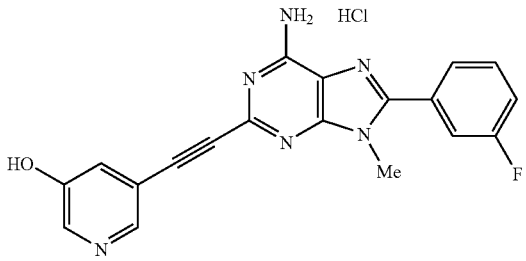 |
| 62 | 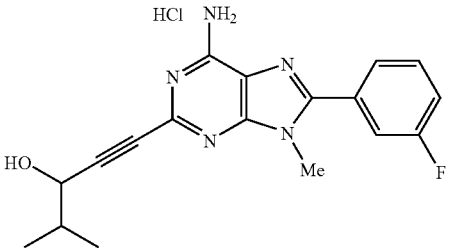 |
| 63 | 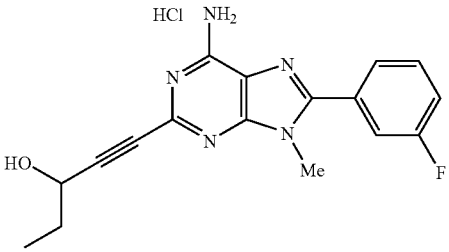 |
| 64 | 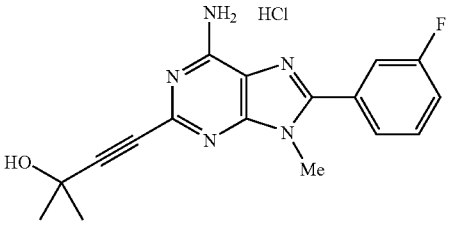 |
| 65 | 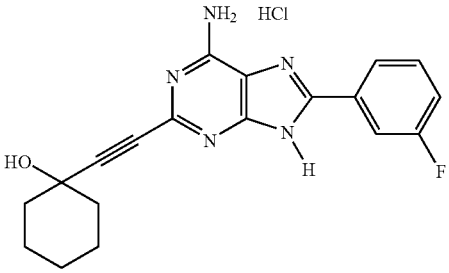 |
TABLE 3-continued
| Ex. No. | Structural Formula |
|---|---|
| 66 | 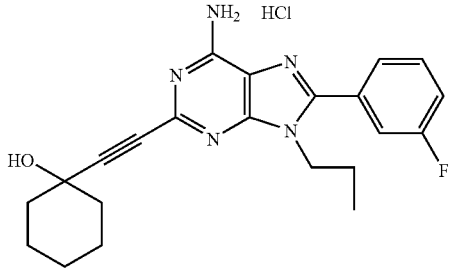 |
| 67 | 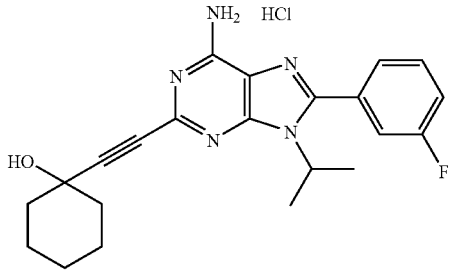 |
| 68 | 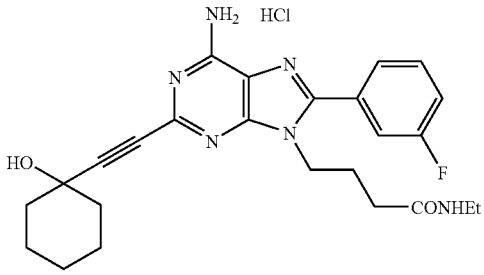 |
| 69 | 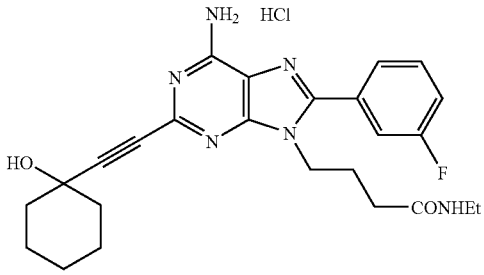 |
| 70 | 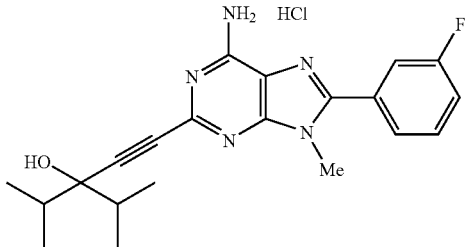 |

TABLE 3-continued
| Ex. No. | Structural Formula |
|---|---|
| 71 | 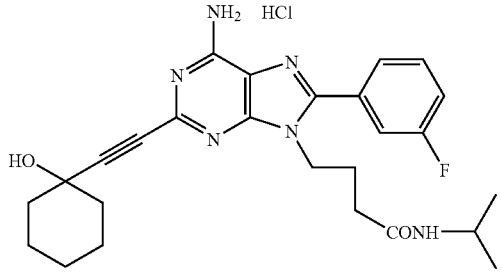 |
| 72 | 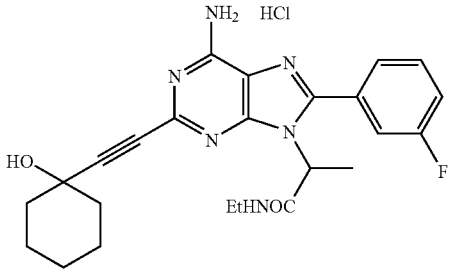 |
| 73 | 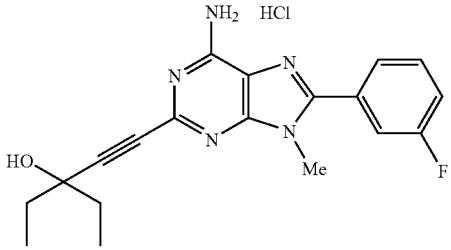 |
| 74 | 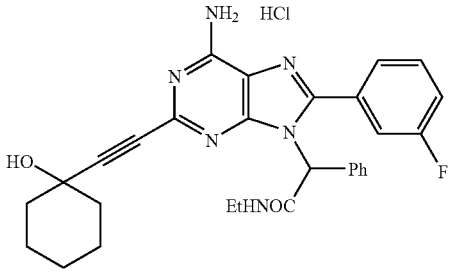 |
| 75 | 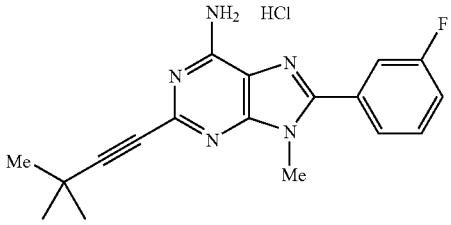 |
| 76 | 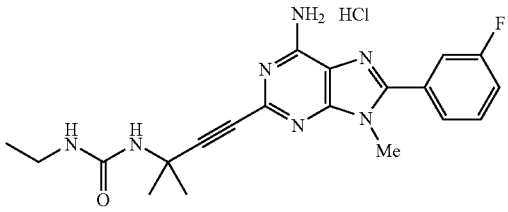 |
TABLE 3-continued
| Ex. No. | Structural Formula |
|---|---|
| 77 | 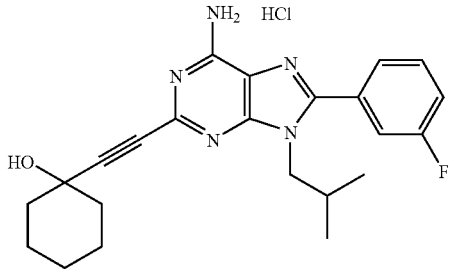 |
| 78 | 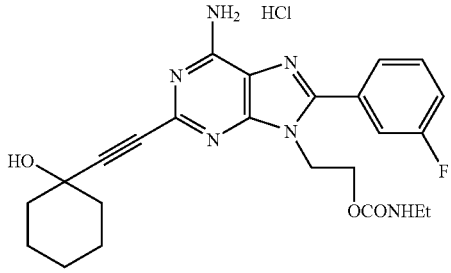 |
| 79 | 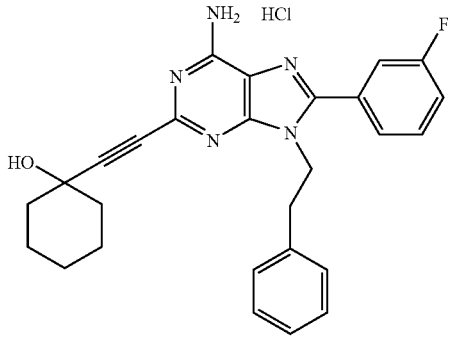 |
| 80 | 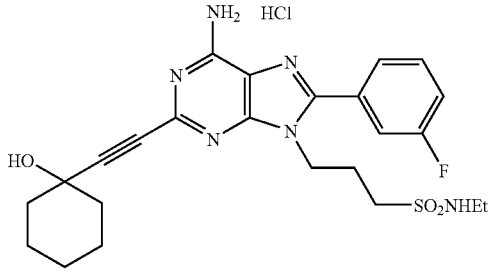 |
| 81 | 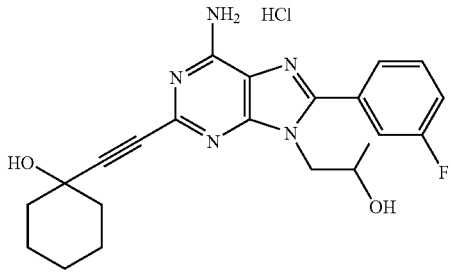 |

TABLE 3-continued
| Ex. No. | Structural Formula |
|---|---|
| 82 | 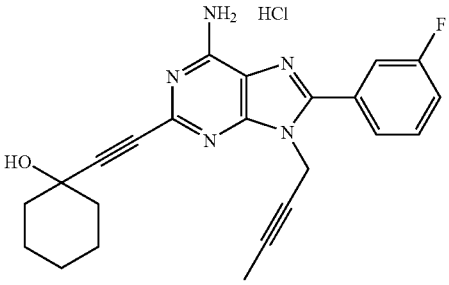 |
| 83 | 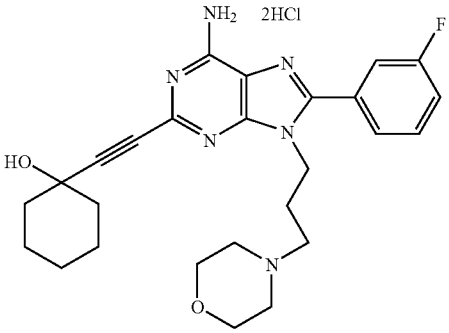 |
| 84 | 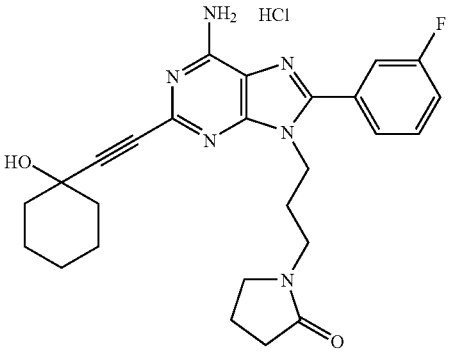 |
| 85 | 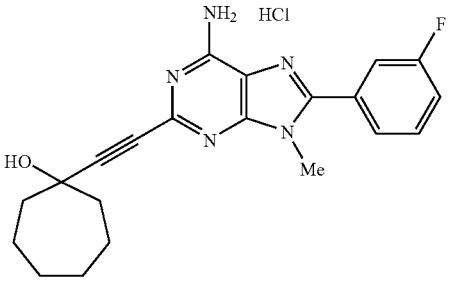 |
| 86 | 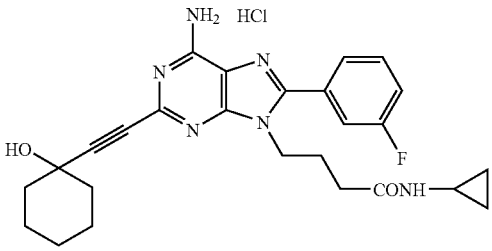 |
TABLE 3-continued
| Ex. No. | Structural Formula |
|---|---|
| 87 | 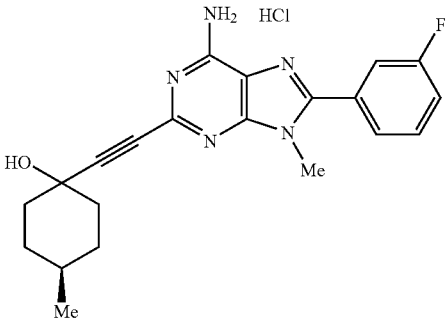 |
| 88 | 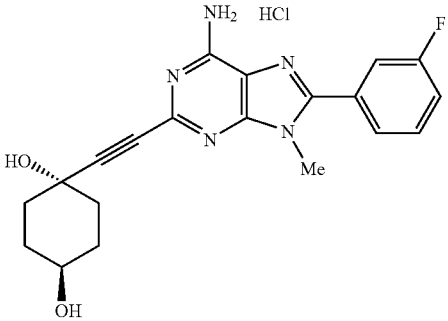 |
| 89 | 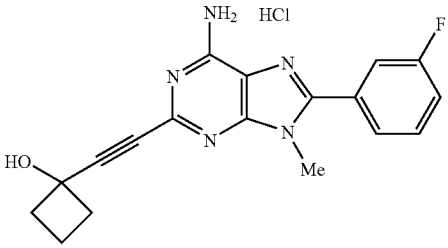 |
| 90 | 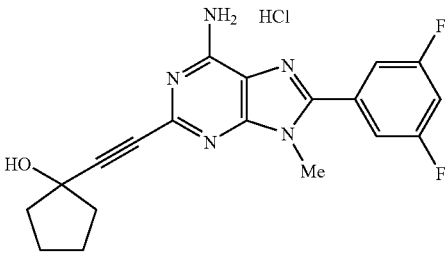 |
| 91 | 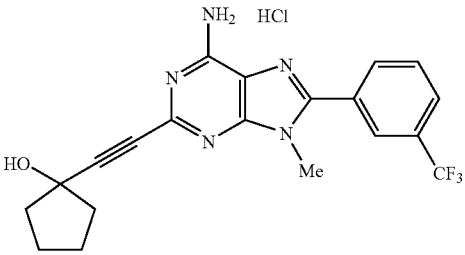 |

TABLE 3-continued
| Ex. No. | Structural Formula |
|---|---|
| 92 | 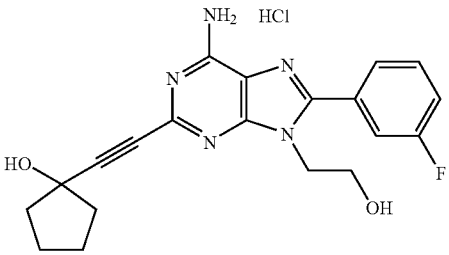 |
| 93 | 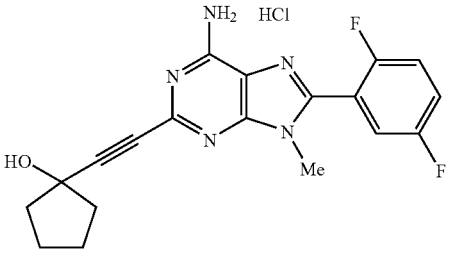 |
| 94 | 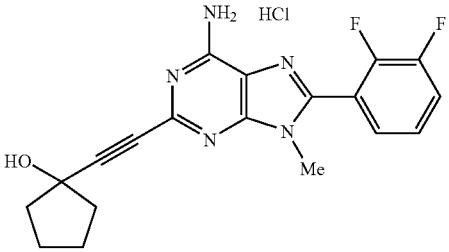 |
| 95 | 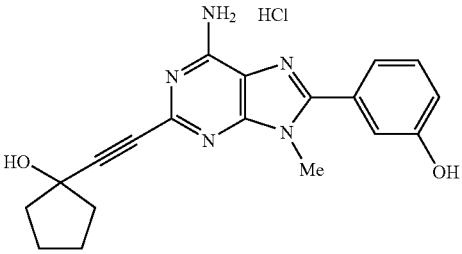 |
| 96 | 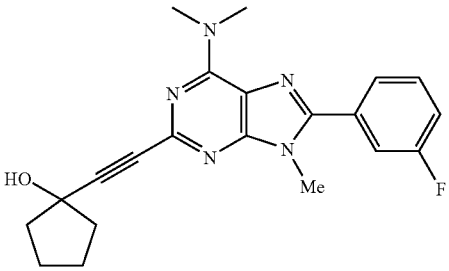 |
TABLE 3-continued
| Ex. No. | Structural Formula |
|---|---|
| 97 | 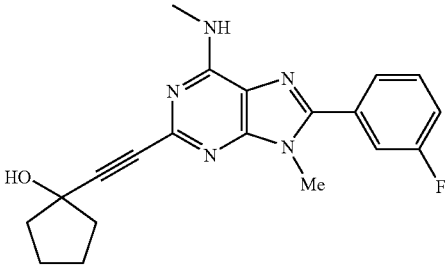 |
| 98 | 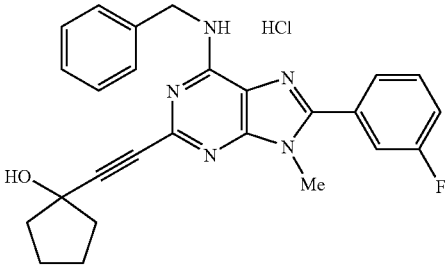 |
| 99 | 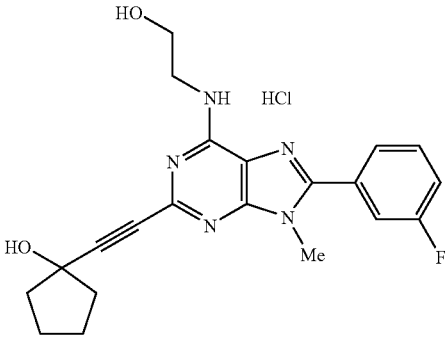 |
| 100 | 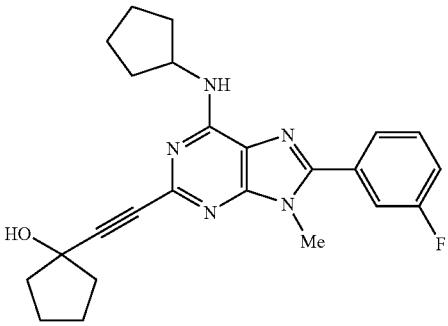 |
| 101 | 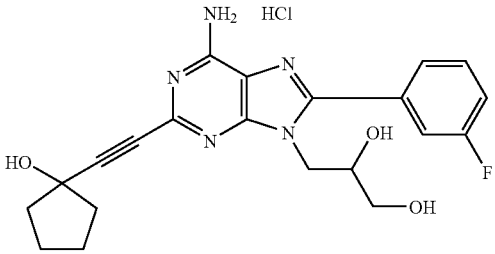 |

TABLE 3-continued
| Ex. No. | Structural Formula |
|---|---|
| 102 | 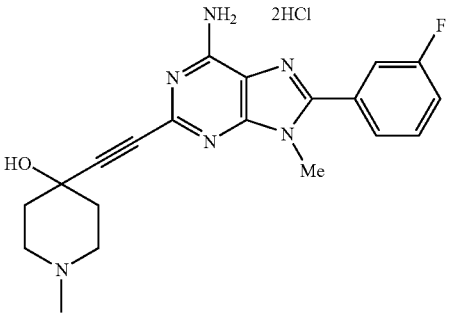 |
| 103 | 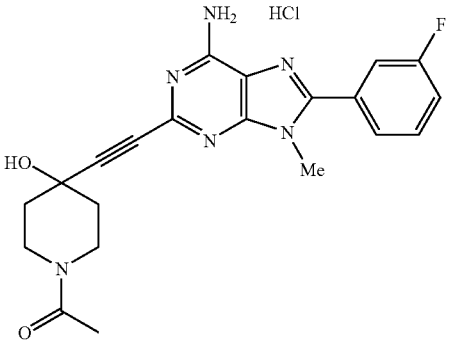 |
| 104 | 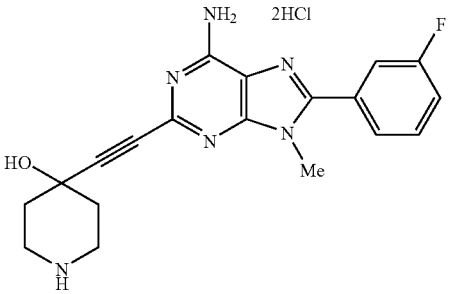 |
| 105 | 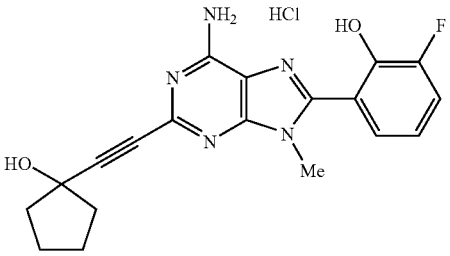 |
| 106 | 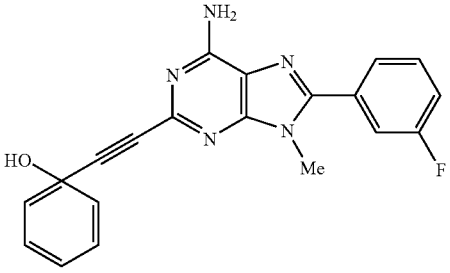 |
TABLE 3-continued
| Ex. No. | Structural Formula |
|---|---|
| 107 | 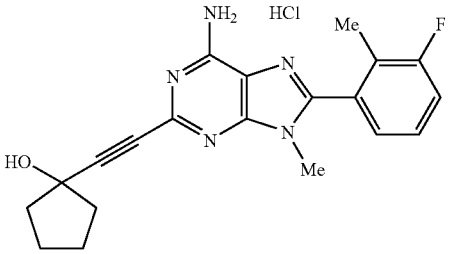 |
| 108 | 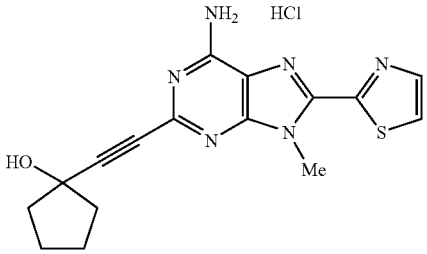 |
| 109 | 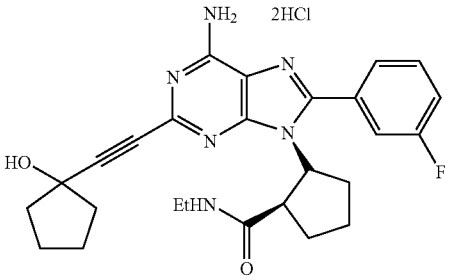 |
| 110 | 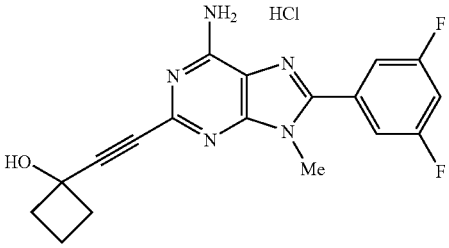 |
| 111 | 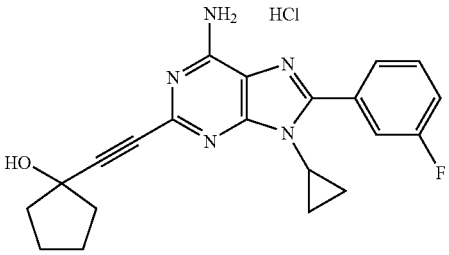 |
| 112 | 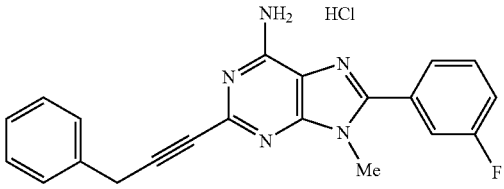 |

TABLE 3-continued
| Ex. No. | Structural Formula |
|---|---|
| 113 | 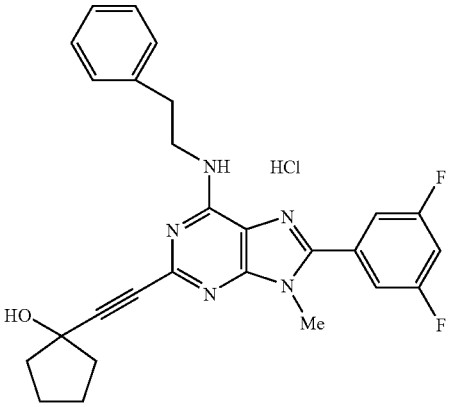 |
| 114 | 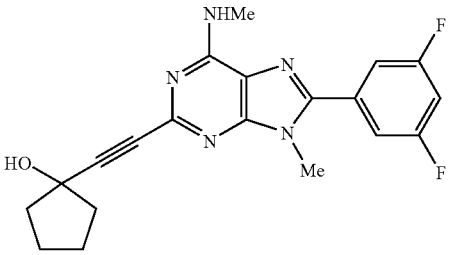 |
| 115 | 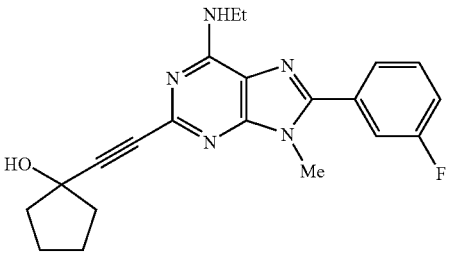 |
| 116 | 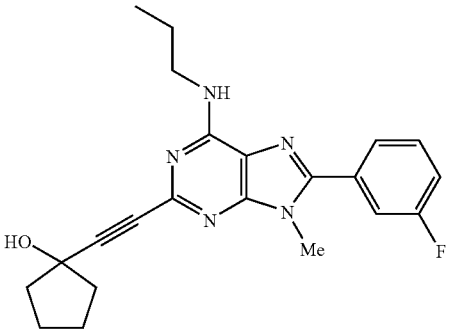 |
TABLE 3-continued
| Ex. No. | Structural Formula |
|---|---|
| 117 | 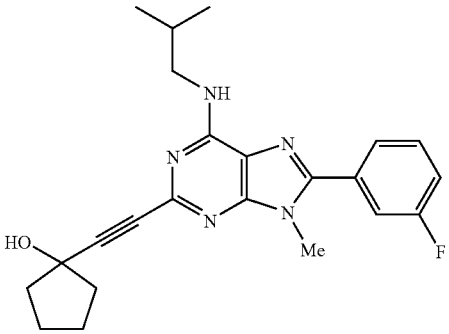 |
| 118 | 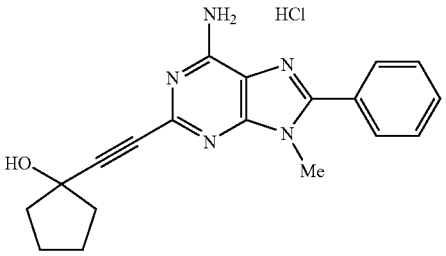 |
| 119 | 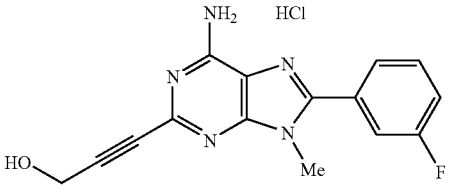 |
| 120 | 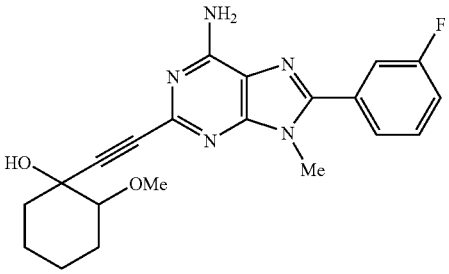 |
| 121 | 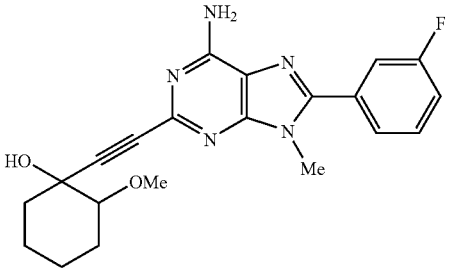 |

TABLE 3-continued
| Ex. No. | Structural Formula |
|---|---|
| 122 | 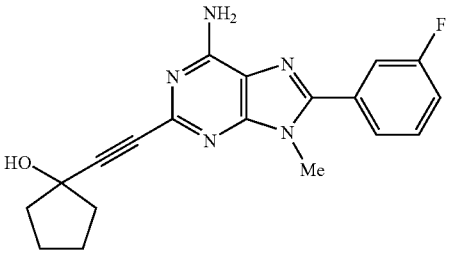 |
| 123 | 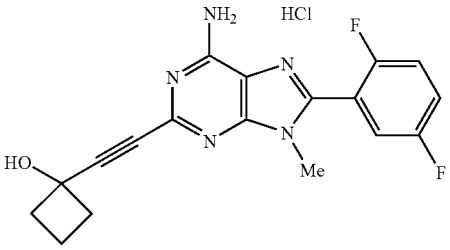 |
| 124 | 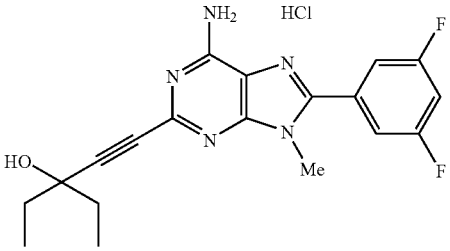 |
| 125 | 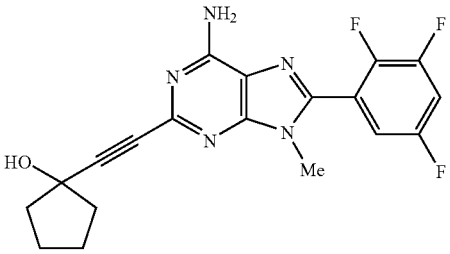 |
| 126 | 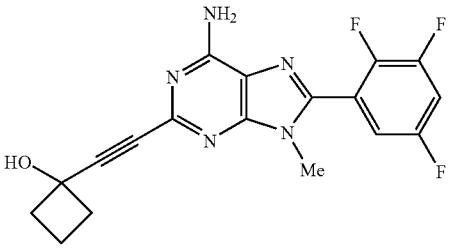 |
| 127 | 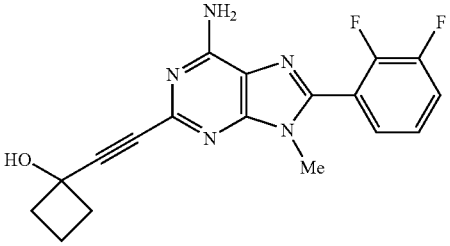 |
TABLE 3-continued
| Ex. No. | Structural Formula |
|---|---|
| 128 | 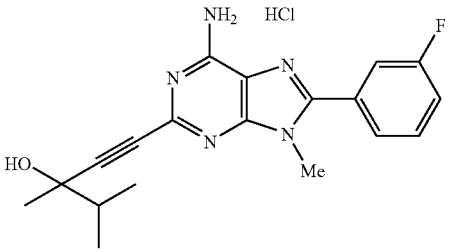 |
| 129 | 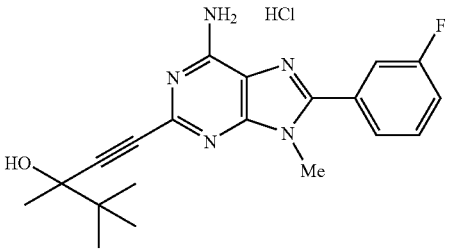 |
| 130 | 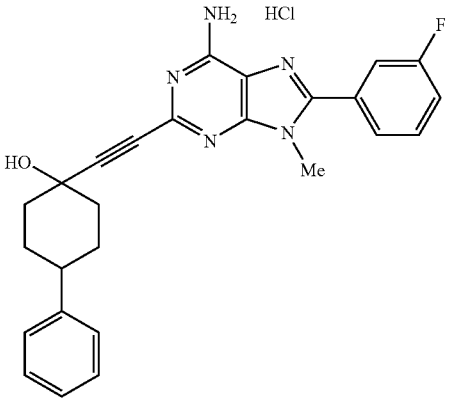 |
| 131 | 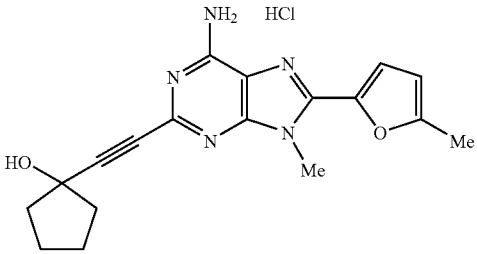 |
| 132 | 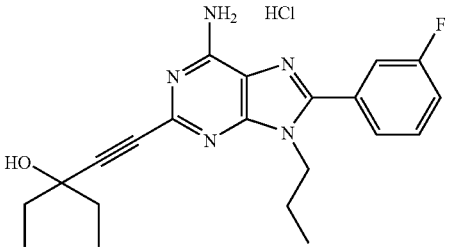 |

TABLE 3-continued
| Ex. No. | Structural Formula |
|---|---|
| 133 | 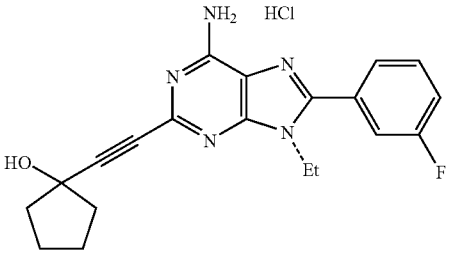 |
| 134 | 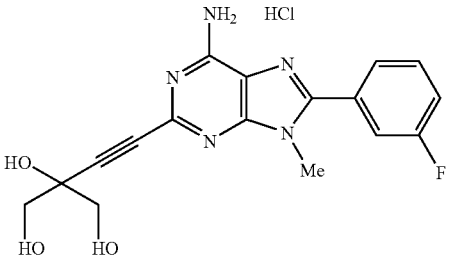 |
| 135 | 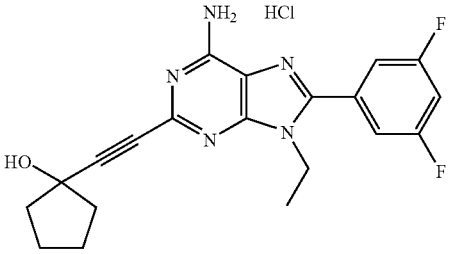 |
| 136 | 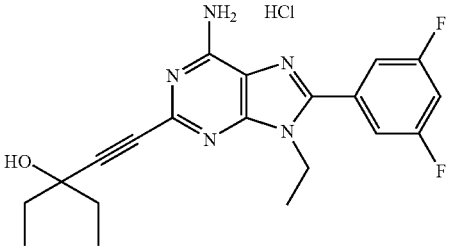 |
| 137 | 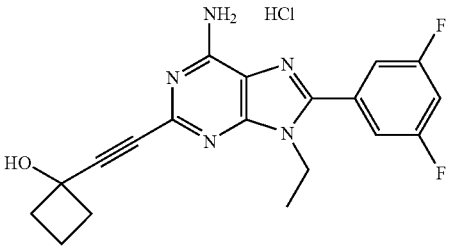 |
| 138 | 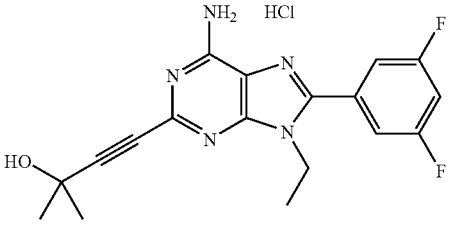 |
TABLE 3-continued
| Ex. No. | Structural Formula |
|---|---|
| 139 | 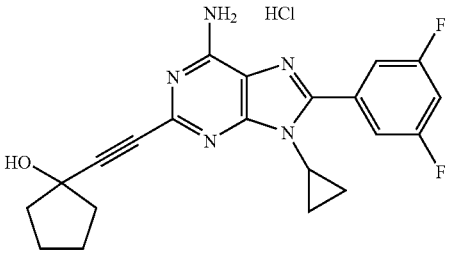 |
| 140 | 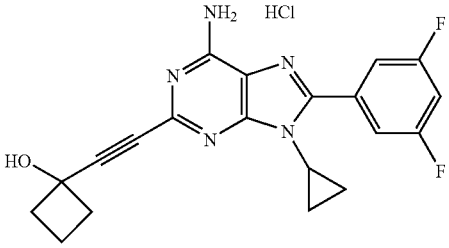 |
| 141 | 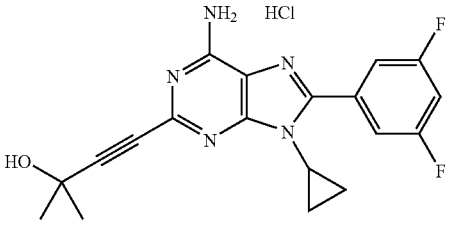 |
| 142 | 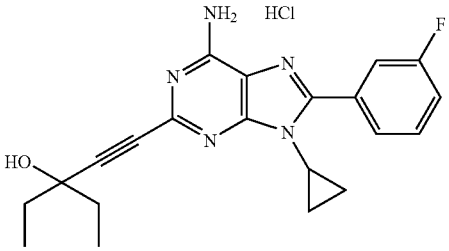 |
| 143 | 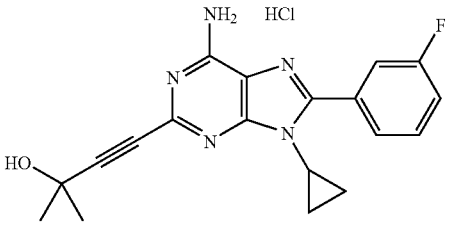 |
| 144 | 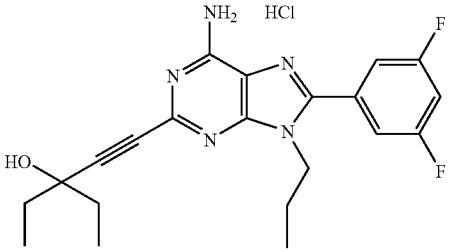 |

TABLE 3-continued
| Ex. No. | Structural Formula |
|---|---|
| 145 | 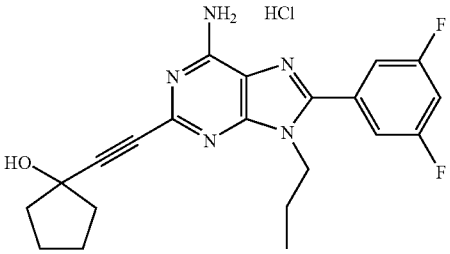 |
| 146 | 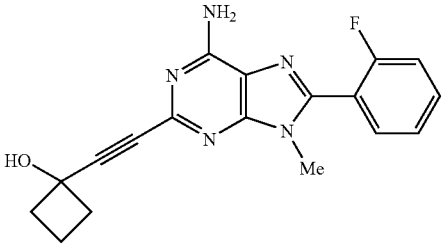 |
| 147 | 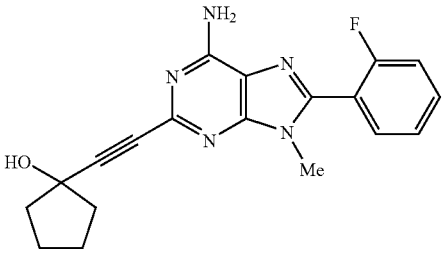 |
| 148 | 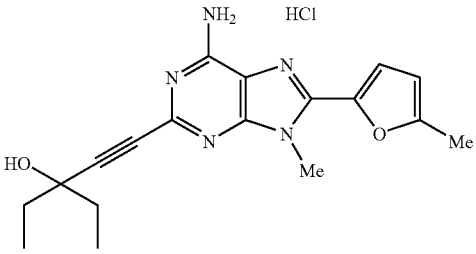 |
| 149 | 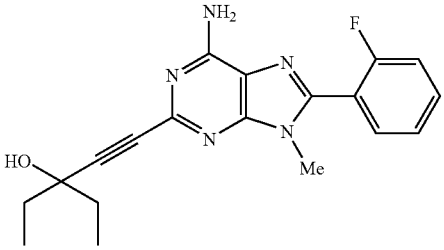 |
| 150 | 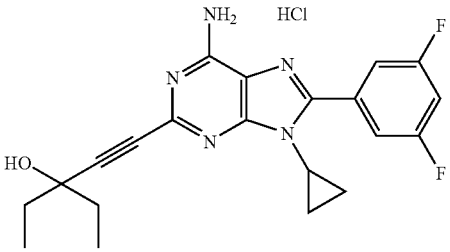 |
TABLE 3-continued
| Ex. No. | Structural Formula |
|---|---|
| 151 | 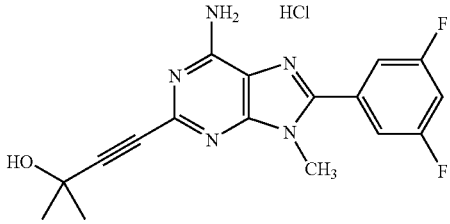 |
| 152 | 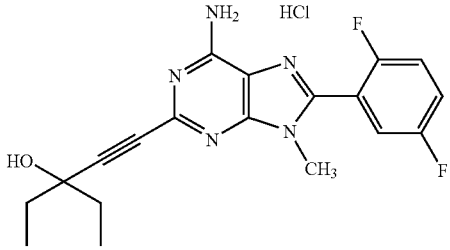 |
| 153 | 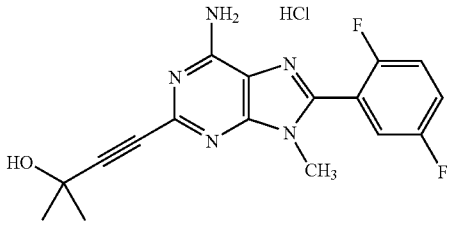 |
| 154 | 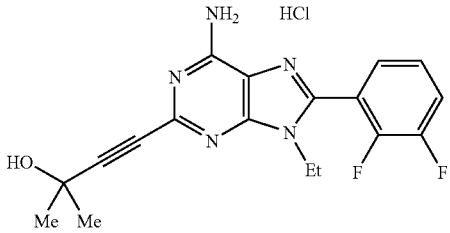 |
| 155 | 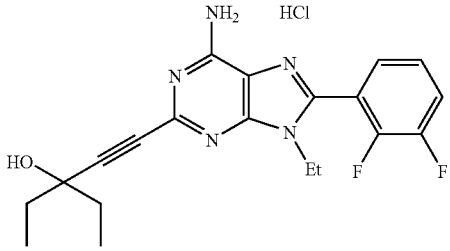 |
| 156 | 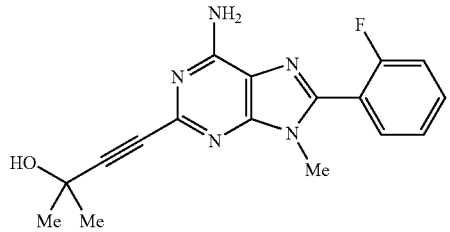 |

TABLE 3-continued
| Ex. No. | Structural Formula |
|---|---|
| 157 | 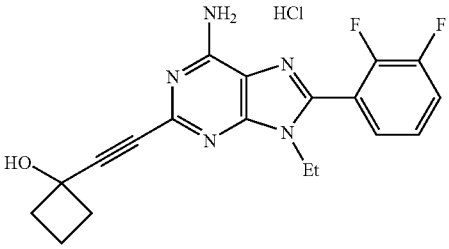 |
| 158 | 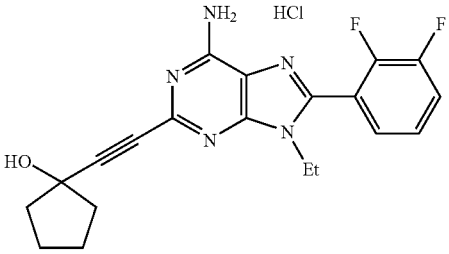 |
| 159 | 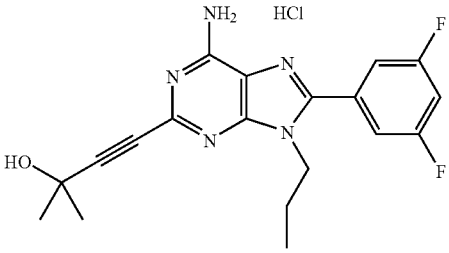 |
| 160 | 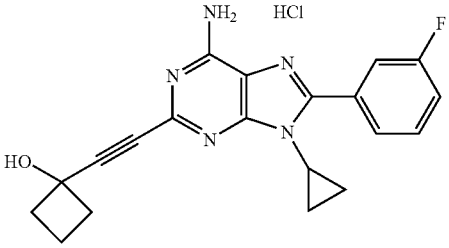 |
| 161 | 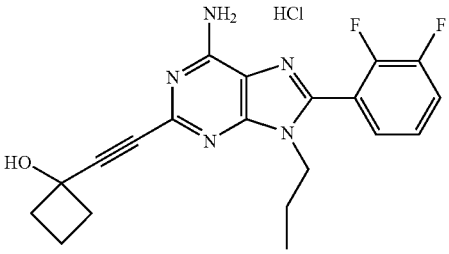 |
| 162 | 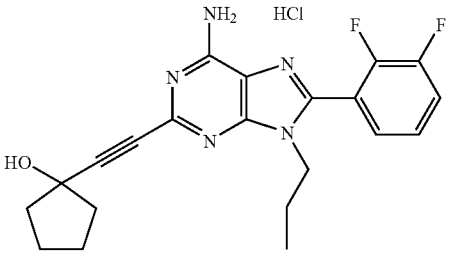 |
TABLE 3-continued
| Ex. No. | Structural Formula |
|---|---|
| 163 | 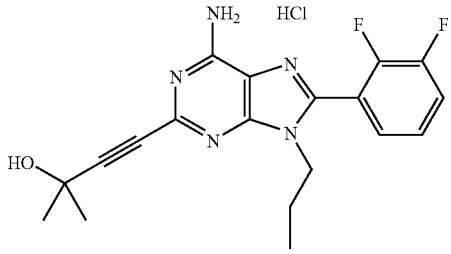 |
| 164 | 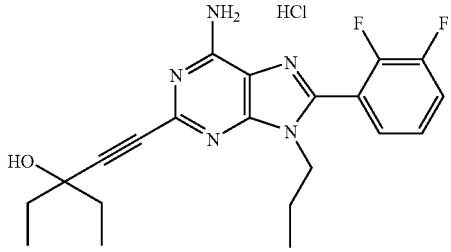 |
| 165 | 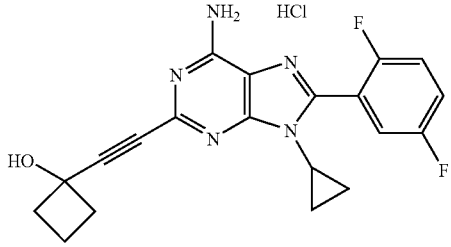 |
| 166 | 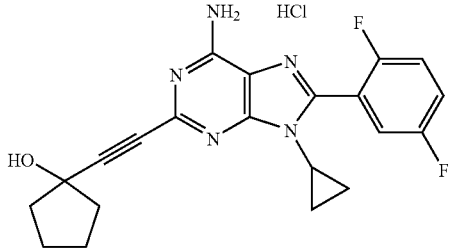 |
| 167 | 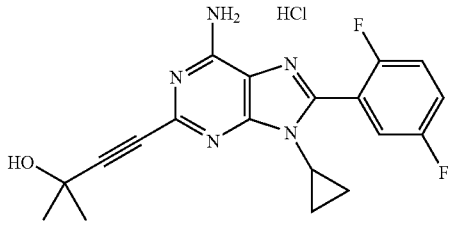 |
| 168 | 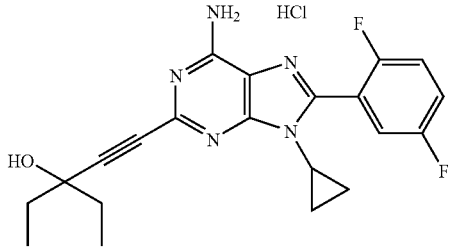 |

TABLE 3-continued
| Ex. No. | Structural Formula |
|---|---|
| 169 | 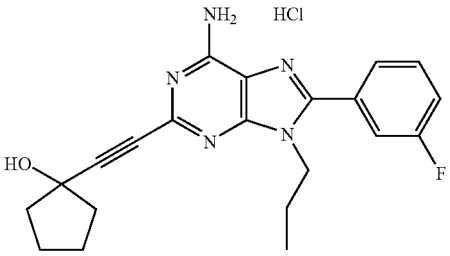 |
| 170 | 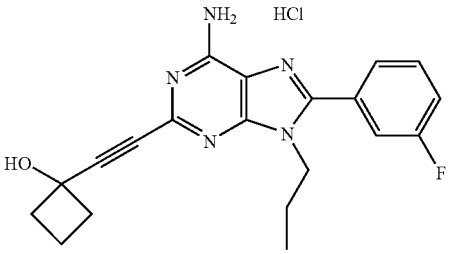 |
| 171 | 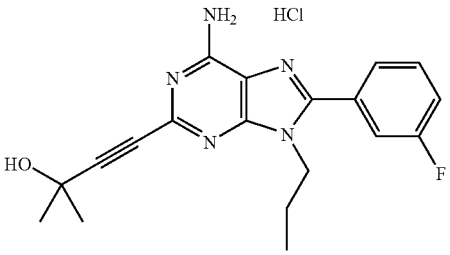 |
| 172 | 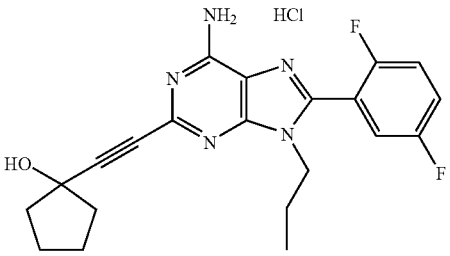 |
| 173 | 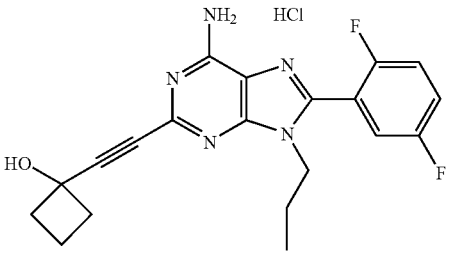 |
TABLE 3-continued
| Ex. No. | Structural Formula |
|---|---|
| 174 | 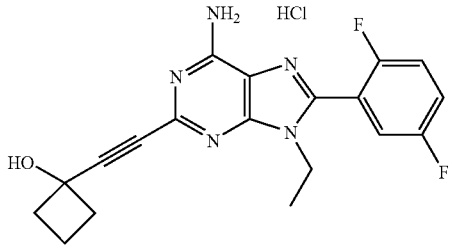 |
| 175 | 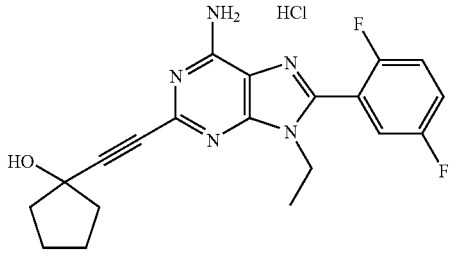 |
| 176 | 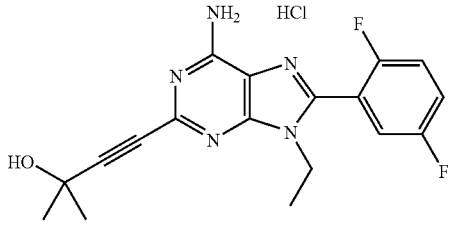 |
| 177 | 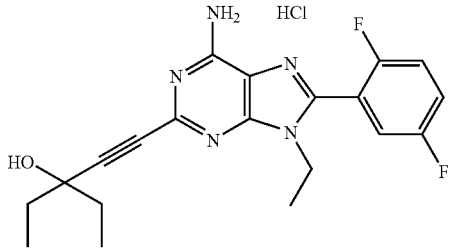 |
| 178 | 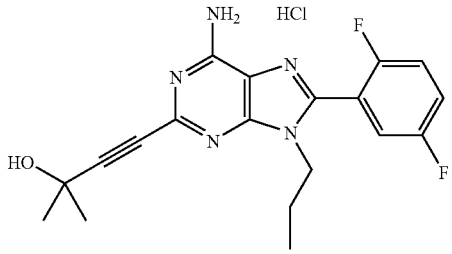 |
| 179 | 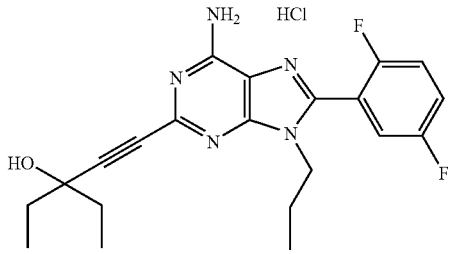 |

TABLE 3-continued
| Ex. No. | Structural Formula |
|---|---|
| 180 | 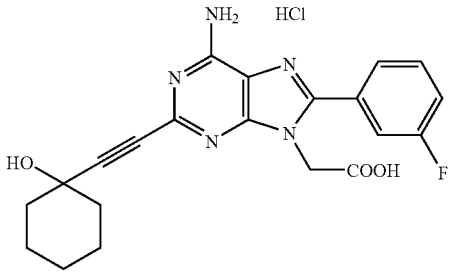 |
| 181 | 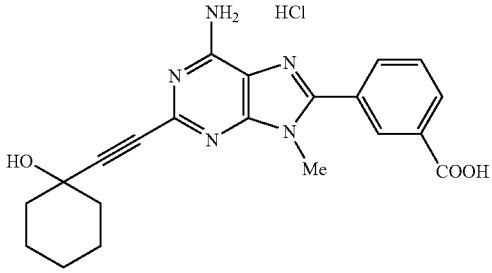 |
| 182 | 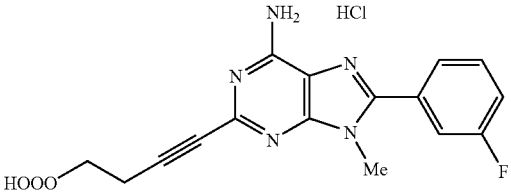 |
| 183 | 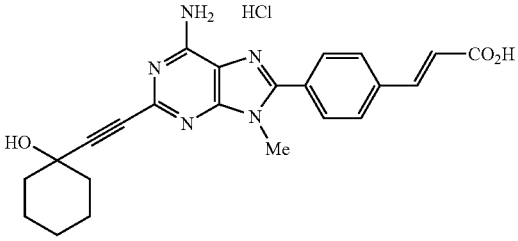 |
| 184 | 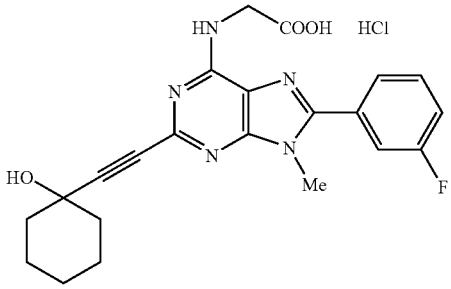 |
| 185 | 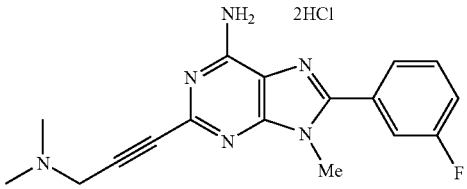 |
TABLE 3-continued
| Ex. No. | Structural Formula |
|---|---|
| 186 | 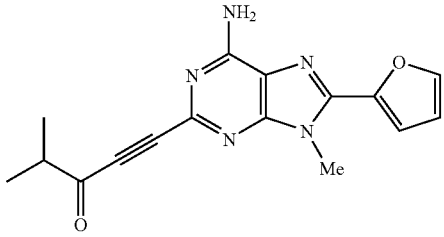 |
| 187 | 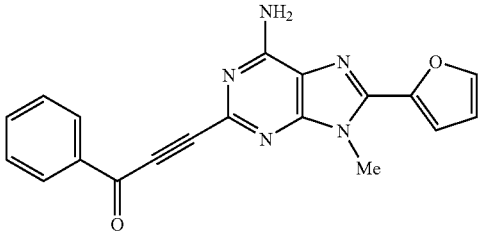 |
| 188 | 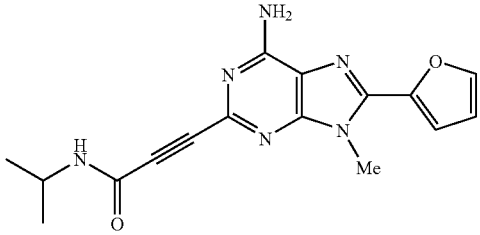 |
| 189 | 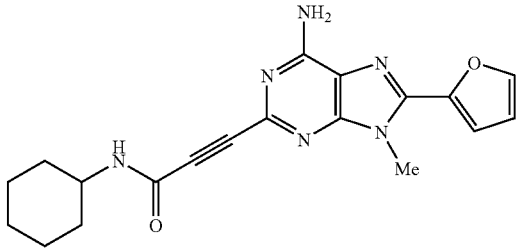 |
| 190 | 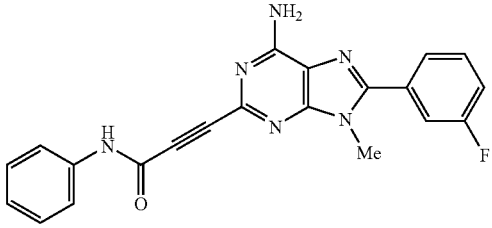 |
| 191 | 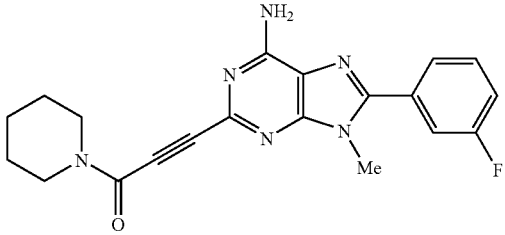 |

TABLE 3-continued
| Ex. No. | Structural Formula |
|---|---|
| 192 | 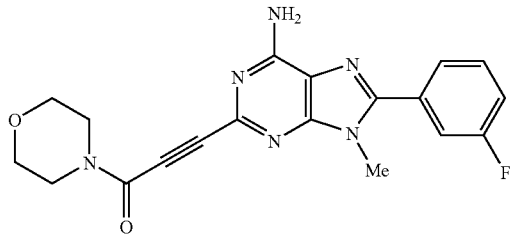 |
| 193 | 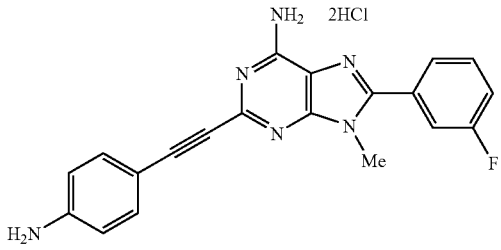 |
| 194 | 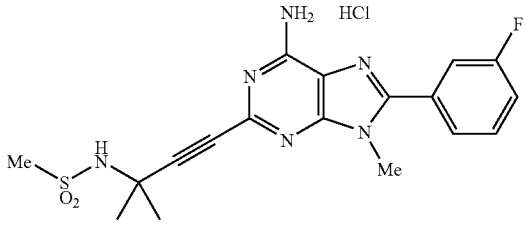 |
| 195 | 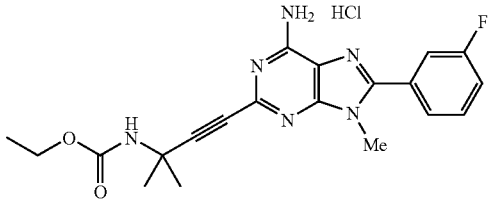 |
| 196 | 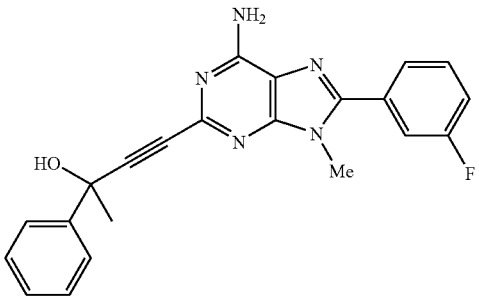 |
TABLE 3-continued
| Ex. No. | Structural Formula |
|---|---|
| 197 | 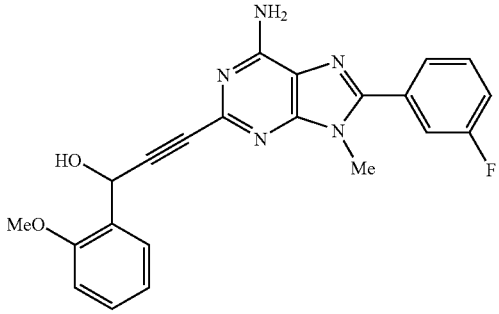 |
| 198 | 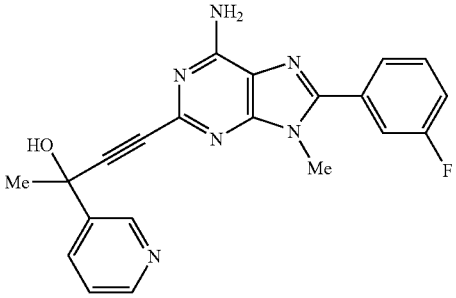 |
| 199 | 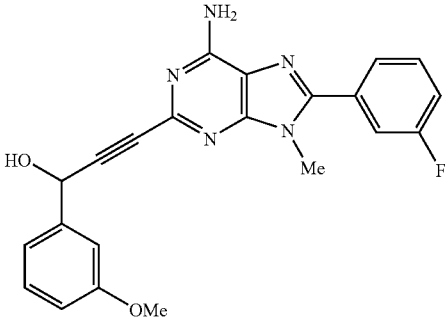 |
| 200 | 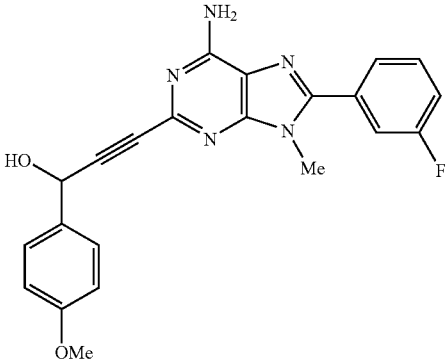 |

TABLE 3-continued
| Ex. No. | Structural Formula |
|---|---|
| 201 | 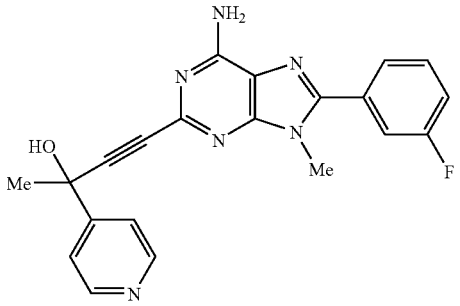 |
| 202 | 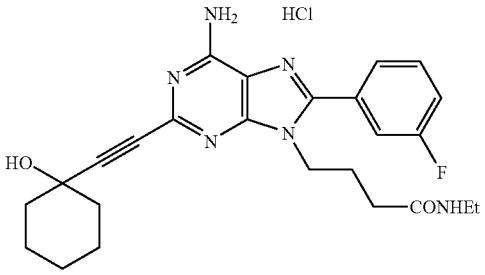 |
| 203 | 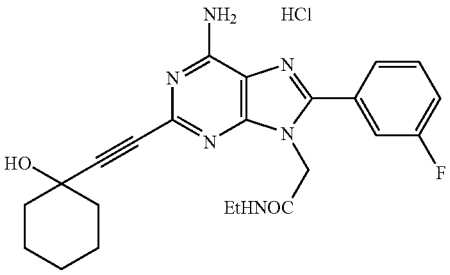 |
| 204 | 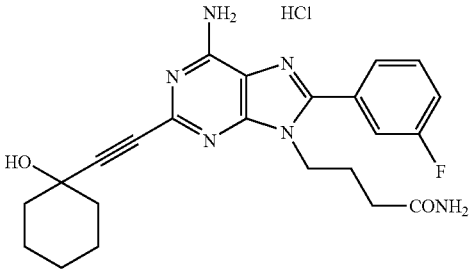 |
| 205 | 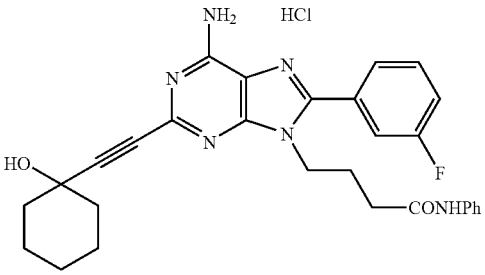 |
TABLE 3-continued
| Ex. No. | Structural Formula |
|---|---|
| 206 | 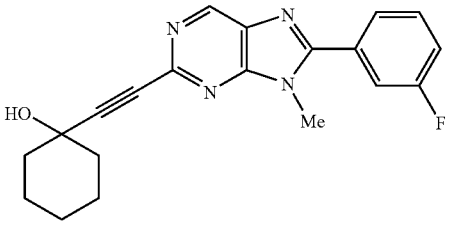 |
| 207 | 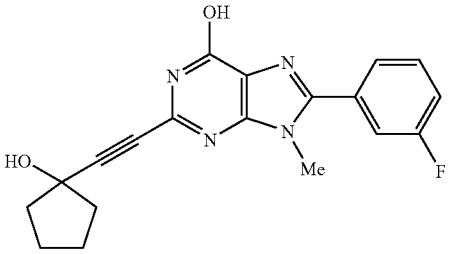 |
| 208 | 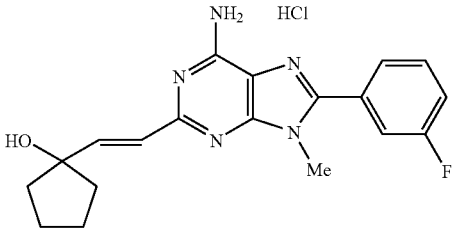 |
| 209 | 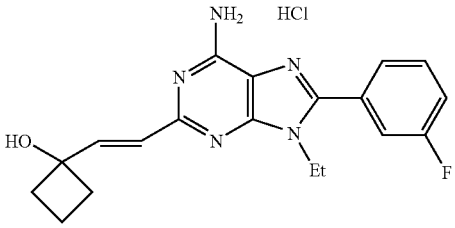 |
| 210 | 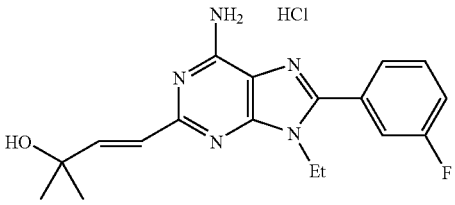 |
| 211 | 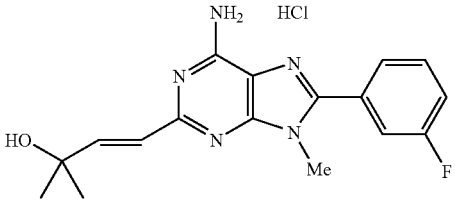 |

TABLE 3-continued
| Ex. No. | Structural Formula |
|---|---|
| 212 | 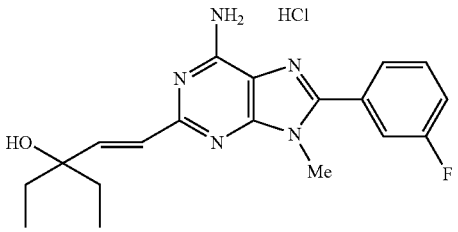 |
| 213-1 | 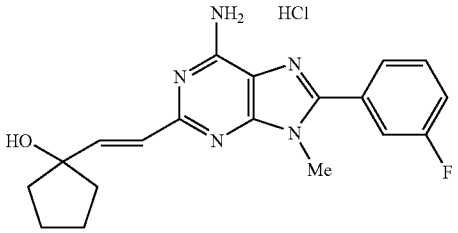 |
| 213-2 | 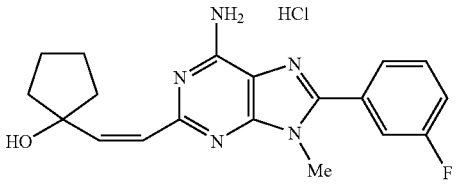 |
| 214 | 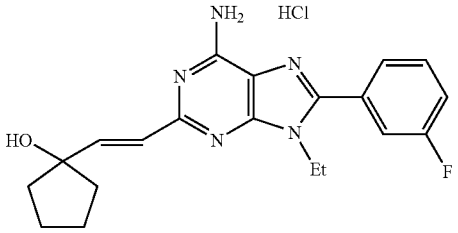 |
| 215 | 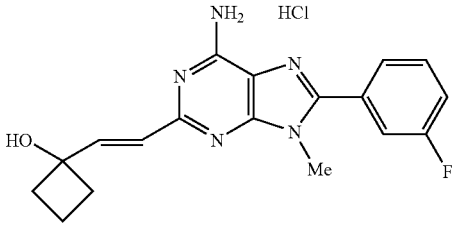 |
| 216 | 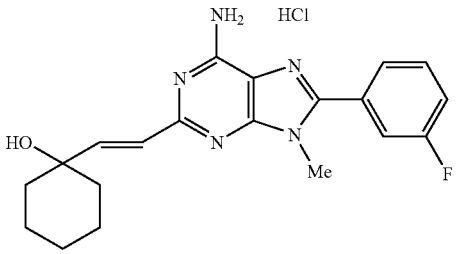 |
TABLE 3-continued
| Ex. No. | Structural Formula |
|---|---|
| 217 | 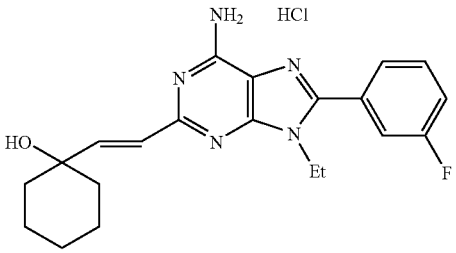 |
| 218 | 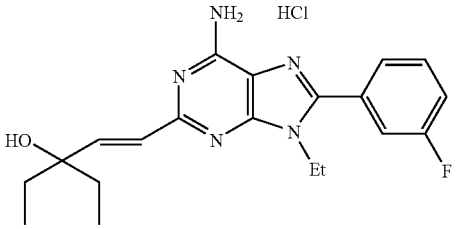 |
| 219 | 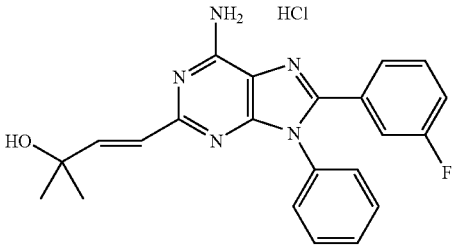 |
| 220 | 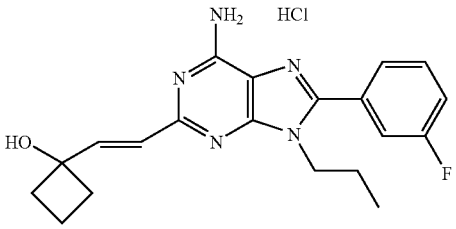 |
| 221 | 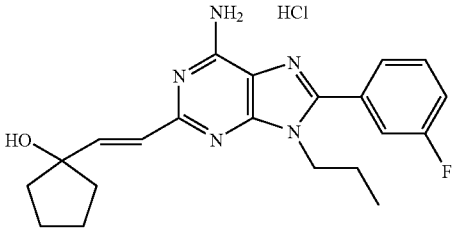 |
| 222 | 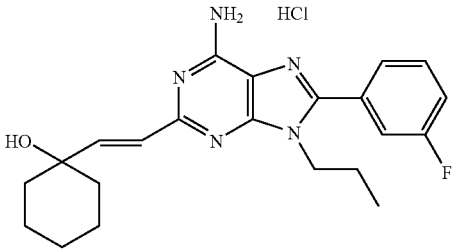 |

TABLE 3-continued
| Ex. No. | Structural Formula |
|---|---|
| 223 | 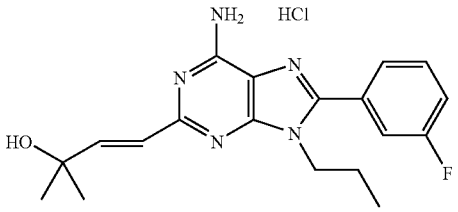 |
| 224 | 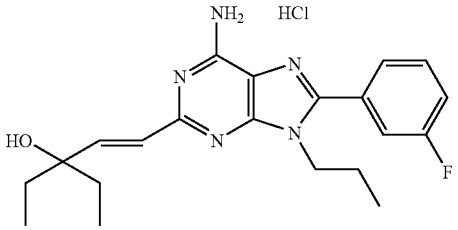 |
| 225 | 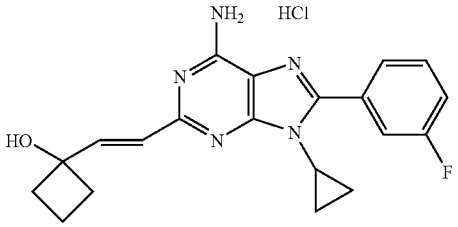 |
| 226 | 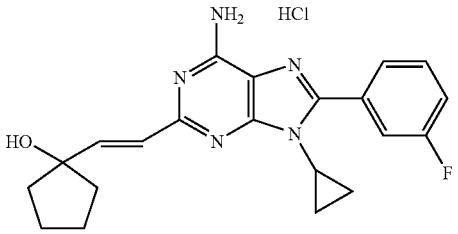 |
| 227 | 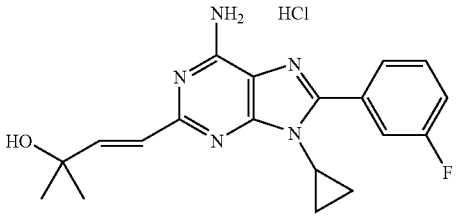 |
| 228 | 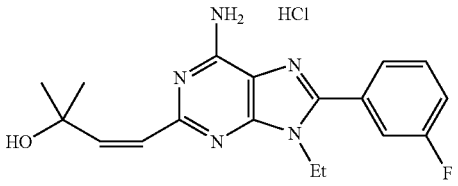 |
TABLE 3-continued
| Ex. No. | Structural Formula |
|---|---|
| 229 | 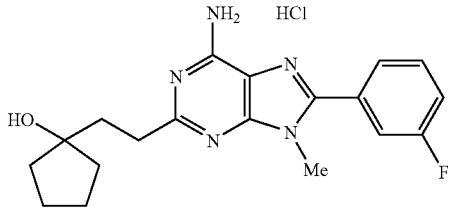 |
| 230 | 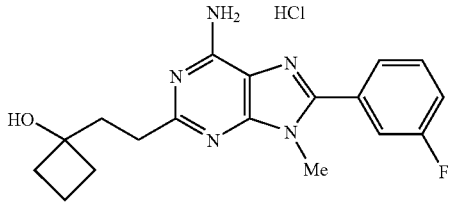 |
| 231 | 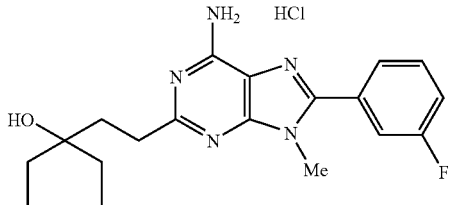 |
| 232 | 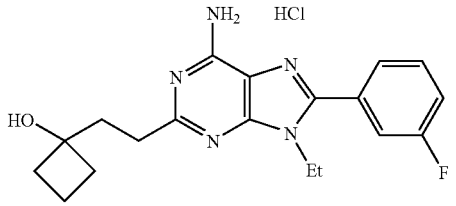 |
| 233 | 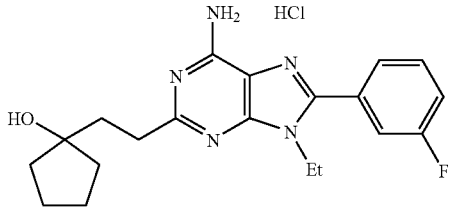 |
| 234 | 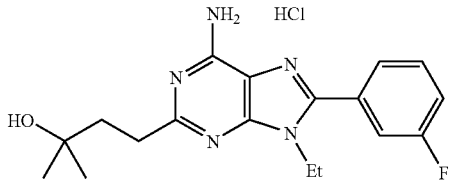 |
| 235 | 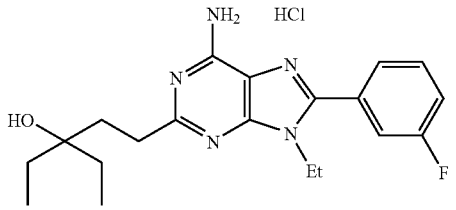 |

TABLE 3-continued

| Ex. No. | Structural Formula |
|---|---|
| 236 | 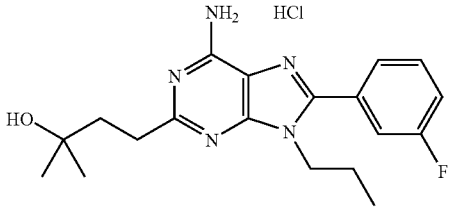 |
| 237 | 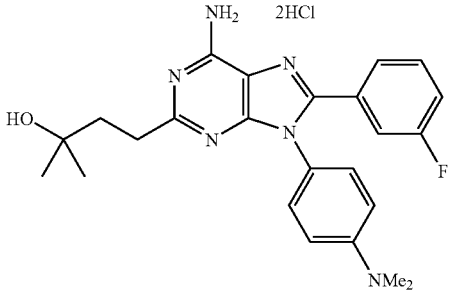 |

Next, in order to facilitate the understanding that the adenosine A2 receptor antagonist has an antidiabetic action, several examples where the fundamental skeletons are different in chemical structures will be shown as hereunder. It goes without saying that the present invention is not limited thereto.

EXAMPLE 238

Adenosine A1 Receptor Binding Experiment

Human adenosine A1 receptor cDNA was subjected to an over-expression in CHOK1 cells and its membrane specimen was suspended in an incubation buffer (20 mM HEPES, 10 mM $MgCl_2$ and 100 mM NaCl; pH 7.4) to make the concentration 66.7 μg/ml. To 0.45 ml of this membrane specimen were added 0.025 ml of tritium-labeled chlorocyclopentyl adenosine (60 nM $^3$H-CCPA; 30 Ci/mmol) and 0.025 ml of the compound to be tested. The solution of the compound to be tested was prepared in such a manner that, firstly, the compound was dissolved in DMSO to make 20 mM concentration and then successively diluted each 10-fold using an incubation buffer. The mixture was allowed to stand at 30° C. for 120 minutes, subjected to a quick suction on a glass fiber filter (GF/B; manufactured by Whatman) and immediately washed with 5 ml of ice-cooled 50mM Tris-HCl buffer twice. After that, the glass fiber filter was transferred to a vial bottle, a scintillator was added and the radioactivity on the filter was measured by a liquid scintillation counter. Calculation of the inhibition rate of the test compound to the receptor bond ($^3$H-CCPA) was carried out by the following expression and, based upon that, $IC_{50}$ was calculated.

Inhibition Rate (%)=[1−{(Binding amount in the presence of drug-Non-specific binding amount)/(Total binding amount-Non-specific binding amount)}]×100

Total binding amount is a $^3$H-CCPA binding radioactivity in the absence of the test compound.

Non-specific binding amount is a $^3$H-CCPA binding radioactivity in the presence of 100 μM of RPIA.

Binding amount in the presence of drug is a $^3$H-CCPA binding radioactivity in the presence of the test compound of various concentrations.

The inhibition constant (Ki value) in Table was calculated from Cheng-Prusoff's expression.

The results are shown in Table 4.

EXAMPLE 239

Adenosine A2a Receptor Binding Experiment

A membrane specimen prepared by an over-expression of adenosine A2a receptor was purchased from Receptor Biology, Inc. and adenosine A2a receptor binding experiments were carried out using that. The purchased membrane specimen was suspended in an incubation buffer (20 mM HEPES, 10 mM $MgCl_2$ and 100 mM NaCl; pH 7.4) to make the concentration 22.2 μg/ml. To 0.45 ml of this membrane specimen were added 0.025 ml of tritium-labeled $^3$H-CGS21680 (500 nM; 30 Ci/mmol) and 0.025 ml of the test compound. The solution of the test compound was prepared in such a manner that, firstly, the compound was dissolved in DMSO to make 20 mM concentration and then successively diluted each 10-fold using an incubation buffer. The mixture was allowed to stand at 25° C. for 90 minutes, subjected to a quick suction on a glass fiber filter (GF/B; manufactured by Whatman) and immediately washed with 5 ml of ice-cooled 50 mM Tris-HCl buffer twice. After that, the glass fiber filter was transferred to a vial bottle, a scintillator was added and the radioactivity on the filter was measured by a liquid scintillation counter. Calculation of the inhibition rate of the test compound to the receptor bond ($^3$H-CGS21680) of A2a was carried out by the following expression and, based upon that, $IC_{50}$ was calculated.

Inhibition Rate (%)=[1−{(Binding amount in the presence of drug-Non-specific binding amount)/(Total binding amount amount-Non-specific binding amount)}]×100

Total binding amount is a $^3$H-CGS21680 binding radioactivity in the absence of the test compound.

Non-specific binding amount is a $^3$H-CGS21680 binding radioactivity in the presence of 100 μM of RPIA.

Binding amount in the presence of drug is a $^3$H-CGS21680 binding radioactivity in the presence of the test compound of various concentrations.

The inhibition constant (Ki value) in Table was calculated from Cheng-Prusoff's expression.

The results are shown in Table 4.
TABLE 4
| Human adenosine A1, A2a receptor binding test | | |
|---|---|---|
| Receptor Test Compound | A1 receptor Ki (μM) | A2a receptor Ki (μM) |
| 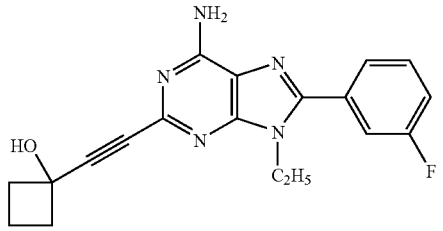 Compound A | 0.024 | 0.002 |
| 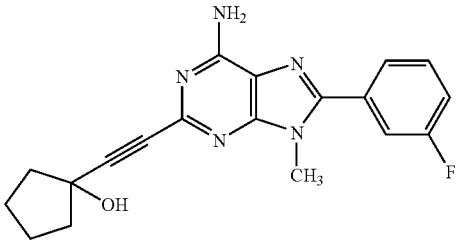 Compound B | 0.019 | 0.0014 |
| 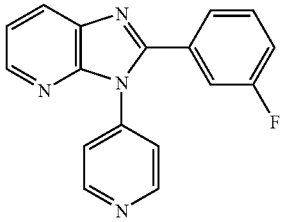 Compound C | 0.054 | 0.75 |
| 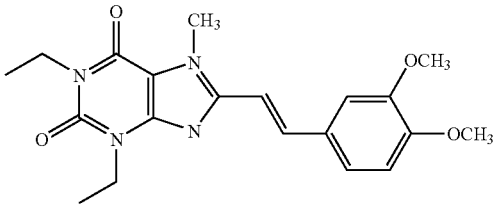 KW6002 | 10< | 0.052 |
| 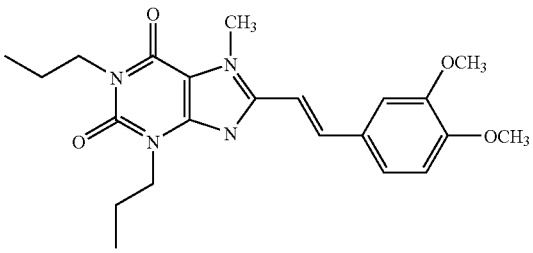 KF17837 | 10< | 0.047 |

EXAMPLE 240

Evaluation of Test Compound in Adenosine A2b Receptor Expressed Cells Using Suppression of NECA-stimulated cAMP Expression as an Index Human adenosine A2b receptor cDNA was over-expressed in CHOK1 cells. The cells were uniformly placed on a 24-well plate at the rate of $1.5\times10^5$ cells/well, incubated for one night and then used for the experiments. Affinity of the test compound to the A2b receptor was evaluated in which the index used was the degree of suppression of the amount of cAMP produced by stimulation of NECA (30 nM) which was an adenosine agonist in the presence of the test compound. Thus, after washing with 2 ml/well of an incubation buffer (Krebs solution; pH7.4) twice, a pre-incubation was carried out at 0.5 ml/well for 30 minutes. After that, 100 μl/well of a mixed solution containing 600 μM of Ro-20-1724 (phosphodiesterase inhibitor), 180 nM of NECA and a test compound which was 6-fold concentrated in a reaction solution were added. After 15 minutes, the reaction was stopped by substituting 0.1N HCl (300 μl/well) for the reaction solution. Measurement of cAMP was carried out using an Amersham cAMP EIA Kit.

Calculation of the suppression rate of the test compound to the NECA-stimulated cAMP production was done by the following expression.

Inhibition Rate (%)=[1−{(cAMP amount in the presence of NECA and test compound-cAMP amount in the case of incubation buffer only)/(cAMP amount stimulated only by NECA-cAMP amount in the case of incubation buffer only)}]×100.

$IC_{50}$ [(3-fluorophenyl)] was calculated from the above. The result is shown in Table 5.

TABLE 5 suppressing action to NECA-stimulated cAMP production in adenosine A2b receptor expressed cells

| Compound | Receptor A2b receptor $IC_{50}$ (μM) |
|---|---|
| Compound A | 0.028 |
| Compound B | 0.070 |
| Compound C | 0.10 |
| KW6002 | 2.85 |
| KF17837 | 1.36 |

EXAMPLE 241

Action of Spontaneous Diabetic Mice (KK-$A^y$/Ta Jcl) to Hyperglycemia (by Single Administration)

Animals: Five male KK-$A^y$/TA Jcl mice for each group (introduced from Nippon Clair)

Preparation and Administration of Test Compound: A test compound in a dose shown in Table 6 was suspended in a 0.5% aqueous solution of methyl cellulose and was orally administered [in a dose] *at a volume* of 10 ml/kg.

Collection of Blood Samples and Determination of Blood [Sugar] *Glucose*: Blood was collected from tail vein immediately before administration of the test compound and also five hours after the administration and blood [sugar] *glucose* was determined.

Method: Tail vein of mouse was injured by a razor without an anesthetization to bleed slightly. The blood (15 μl) was collected and immediately mixed with 135 μl of a 0.6 M perchloric acid. Glucose in the supernatant obtained by a centrifugal separation (at 1500 g for 10 minutes at 4° C. using a cooling centrifuge GS-6KR of Beckmann) was determined by a Glucose CII Test Wako (Wako Pure Chemicals).

The result is shown in Tables 6-1 to 6-4 for each experiment.

The result is shown in terms of "(% ratio of the blood sugar after 5 hours from the administration to the blood sugar before the administration)±(standard error)". The data were subjected to a one-way layout analysis of variance and then subjected to a multiple comparison of Dunnett type. The case where $p<0.05$ was judged that a significant difference was available.

TABLE 6-1

Action of spontaneous diabetic mice (KK-$A^7$/Ta Jcl) to hyperglycemia

| Test Compound | Dose (mg/kg) | $\frac{\text{Blood sugar level 5 hr after the administration}}{\text{Blood sugar level before the administration}}\times100$ | Significance |
|---|---|---|---|
| Solvent | | 72.4 ± 4.4 | |
| Compound A | 10 | 47.8 ± 4.8 | ** |
| Compound B | 10 | 51.8 ± 2.9 | ** |

Compounds A and B are administered in a form of sulfate.

(**; $p < 0.01$ vs. Solvent)

TABLE 6-2

Action of spontaneous diabetic mice (KK-$A^7$/Ta Jcl) to hyperglycemia

| Test Compound | Dose (mg/kg) | $\frac{\text{Blood sugar level 5 hr after the administration}}{\text{Blood sugar level before the administration}}\times100$ | Significance |
|---|---|---|---|
| Solvent | | 69.8 ± 2.3 | |
| Compound C | 30 | 48.5 ± 3.4 | ** |

(**; $p < 0.01$ vs. Solvent)

TABLE 6-3

Action of spontaneous diabetic mice (KK-$A^7$/Ta Jcl) to hyperglycemia

| Test Compound | Dose (mg/kg) | $\frac{\text{Blood sugar level 5 hr after the administration}}{\text{Blood sugar level before the administration}}\times100$ | Significance |
|---|---|---|---|
| Solvent | | 76.6 ± 3.9 | |
| KW6002 | 100 | 57.6 ± 5.6 | * |

(*; $p < 0.05$ vs. Solvent)

TABLE 6-4

| Action of spontaneous diabetic mice (KK-A$^7$/Ta Jcl) to hyperglycemia | | | |
|---|---|---|---|
| Test Compound | Dose (mg/kg) | Blood sugar level: 5 hr after the administration / Blood sugar level before the administration ×100 | Significance |
| Solvent | | 80.7 ± 2.3 | |
| KF17837 | 100 | 62.0 ± 2.8 | * |

(*; $p < 0.05$ vs. Solvent)

As such, adenosine A2 receptor antagonist showed a clear hypoglycemic action in spontaneous diabetic models.

In the experiments for the NECA-stimulated glucose production in hepatic cells, the antagonist which was specific to adenosine A2a receptor did not show a [saccharogenesis] *glucose production* suppressing action and only the compound showing a strong [suppressing action of A2b] *affinity to A2b receptor* showed a [saccharogenesis] *glucose production* suppressing action. In addition, a glucose tolerance improving action in glucose tolerance test which is an index for [sugar] *glucose* utilization in peripheral tissues was noted both in antagonists which were specific to adenosine A2a and in compounds having a strong antagonistic action to A2b receptor.

On the other hand, no hypoglycemic action was noted for FK453 (European Journal of Pharmacology, 279, 217–225, 1995.) known as an antagonist specific to adenosine A1 receptor even at the dose of 100 mg/kg in the present diabetic models. In addition, no glucose tolerance improving action was noted in glucose tolerance test as well.

From the above, it is clear that the effect in the present diabetic models is due to an antagonistic action of adenosine A2 (A2a and/or A2b) receptor.

REFERENTIAL EXAMPLE

Synthesis of 2-(3-Fluorophenyl)-(4-pyridyl)-3H-imidazo[4,5-b]pyridine Hydrochloride (Compound C)

N$^2$-(4-Pyridyl)-2,3-pyridinediamine was dissolved in 20 ml of methanol, 1 ml of acetic acid and 745 mg of 3-fluorobenzaldehyde were added and the mixture was stirred at room temperature for 16 hours. The reaction solution was concentrated and subjected to an azeotropy with toluene for three times. The resulting residue after concentration was suspended in 30 ml of ethanol, 1.5 g of anhydrous iron chloride were added thereto and the mixture was heated under reflux for 5 hours. The reaction solution was returned to room temperature, concentrated to dryness, diluted with 100 ml of ethyl acetate and washed with 50 ml of water and 20 ml of brine. The organic layer was concentrated to dryness and the residue was purified by a silica gel column chromatography (eluted with ethyl acetate:n-hexane=3:1) to give 0.36 g of a free compound. The free compound was dissolved in 20 ml of methanol, 6.5 ml of 1N hydrochloric acid were added thereto and the mixture was concentrated to dryness. Ethanol was added to the residue, the mixture was subjected to an azeotropy, suspended in 10 ml ethyl acetate and 0.45 g of the title compound was obtained by collecting by filtration. The overall yield was 46%.

NMR (400 MHz, [δ,] δ, DMSO-d$_6$); 7.35–7.55 (m, 5H), [7.88 (d, J=6.4 Hz, 2H), 8.33 (dd, J=1.6 Hz, 8.0 Hz, 1H), 8.45 (dd, J=1.6 Hz, 4.8 Hz, 1H), 8.94 (d, J=6.4 Hz, 2H).] *7.88 (d, J=6.4 Hz, 2H), 8.33 (dd, J=1.6 Hz, 8.0 Hz, 1H), 8.45 (dd, J=1.6 Hz, 4.8 Hz, 1H), 8.94 (d, J=6.4 Hz, 2H).*

The purine compound and the adenosine A2 receptor antagonists which are the compounds of the present invention show a clear hypoglycemic action in spontaneous diabetic models and also have an action of improving an impaired glucose tolerance, whereby they are useful as a preventive or therapeutic agent for diabetes mellitus and diabetic complications.

What is claimed is:

1. A purine compound represented by the formula (I), or its pharmacologically acceptable salt thereof, (I)

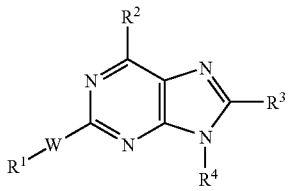

wherein in the formula (I),

R$^1$ represents:

1) formula:

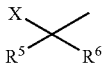

wherein X is a hydrogen atom, a hydroxyl group, an optionally substituted lower alkyl group, an optionally substituted lower alkoxy group, an optionally substituted aryl group, an optionally substituted heteroaryl group, an optionally substituted acyl group, an optionally substituted acyloxy group or an optionally substituted amino group; and R$^5$ and R$^6$ are the same as or different from each other and each represents a hydrogen atom, an optionally substituted lower alkyl group, an optionally substituted saturated or unsaturated C$_{3-8}$ cycloalkyl group, an optionally substituted C$_{3-8}$ cycloalkyl-C$_{2-6}$ alkyl group, an optionally substituted aryl group, an optionally substituted heteroaryl group, an optionally protected carboxyl group or an optionally substituted four- to six-membered ring having at least one hetero atom; optionally R$^5$ and R$^6$ is either an oxygen atom or a sulfur atom together, or R$^5$ and R$^6$ are a ring which may have a hetero atom being formed together with a carbon atom to which they are bonded; wherein said ring may be substituted; or 2) a five- or six-membered aromatic ring that may have a substituent group and a hetero atom;

W represents formula —CH$_2$CH$_2$—, —CH═CH— or —C≡C—;

R$^2$ represents a hydrogen atom, an optionally substituted lower alkyl group, a hydroxyl group or a formula —NR$^7$R$^8$, wherein R$^7$ and R$^8$ are the same as or different from each other and each represents a hydrogen atom, a hydroxyl group, an optionally substituted lower alkyl group, and optionally substituted acyl group, an optionally substituted C$_{3-8}$ cycloalkyl group, an optionally substituted aryl group or an optionally substituted heteroaryl group; optionally R$^7$ and R$^8$ are a saturated ring which is formed together with a nitrogen atom to which they are bonded, said saturated ring is selected from the group consisting of aziridine, azetidine, pyrrolidine, piperidine, perhydroazepine, perhydroazocine, piperazine, homopiperazine, morpholine and thiomorpholine; wherein the ring optionally has a substituent selected from the group consisting of a lower alkyl group, a halogen and an acyl group;

$R^3$ represents an optionally substituted $C_{3-8}$ cycloalkyl group, an optionally substituted aryl group, an optionally substituted heteroaryl group or an optionally substituted $C_{2-6}$ alkenyl group; and $R^4$ represents a hydrogen atom, an optionally substituted lower alkyl group, an optionally substituted $C_{3-8}$ cycloalkyl group, an optionally substituted aryl group, an optionally substituted heteroaryl group, an optionally substituted $C_{2-6}$ alkenyl group, an optionally substituted $C_{2-6}$ alkynyl group or an optionally substituted cyclic ether group; wherein when W is —$CH_2CH_2$—, then X is not a hydrogen atom or an alkyl group.

2. The purine compound or its pharmacologically acceptable salt thereof as claimed in claim 1, wherein W is —C≡C—.

3. The purine compound, or its pharmacologically acceptable salt thereof, as claimed in claim 1 or 2, wherein $R^2$ is formula —$NR^7R^8$, and $R^7$ and $R^8$ have the same meanings as defined above.

4. The purine compound as claimed in claim 1, or its pharmacologically acceptable salt thereof, wherein $R^3$ is an optionally substituted aryl group or an optionally substituted heteroaryl group.

5. The purine compound as claimed in claim 1, or its pharmacologically acceptable salt thereof, wherein $R^4$ is an optionally substituted lower alkyl group, an optionally substituted aryl group or an optionally substituted heteroaryl group.

6. The purine compound as claimed in claim 1, or its pharmacologically acceptable salt thereof, wherein $R^1$ is a formula:

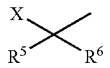

wherein X represents a hydroxyl group, an acyloxy group or an optionally substituted lower alkyl group; and $R^5$ and $R^6$ are the same as or different from and each represents an optionally substituted lower alkyl group or a ring being formed together with the carbon atom to which they are bonded which may have a hetero atom and may be substituted.

7. The purine compound as claimed in claim 1, or its pharmacologically acceptable salt thereof, wherein $R^1$ is a formula:

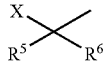

wherein X represents a hydroxyl group or a lower aliphatic acyloxy group; and $R^5$ and $R^6$ are the same as or different from each other and each represents an optionally substituted lower alkyl group or an optionally substituted $C_{3-8}$ cycloalkyl group being formed with the carbon atom to which they are bonded; and $R^2$ is a formula —$NR^7R^8$, wherein $R^7$ and $R^8$ are the same as or different from and each represents a hydrogen atom, a lower alkyl group or an acyl group.

8. The purine compound as claimed in claim 1, or its pharmacologically acceptable salt thereof, wherein $R^1$ is a formula:

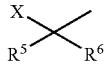

wherein X represents a hydroxyl group or a lower aliphatic acyloxy group; and $R^5$ and $R^6$ are the same as or different from each other and each represents an optionally substituted lower alkyl group or an optionally substituted $C_{3-8}$ cycloalkyl group being formed together with the carbon atom to which they are bonded; and $R^2$ is a formula —$NR^7R^8$, wherein both $R^7$ and $R^8$ represent hydrogen atoms.

9. The purine compound as claimed in claim 1, or its pharmacologically acceptable salt thereof, wherein $R^1$ is a formula:

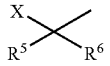

wherein X represents a hydroxyl group or a lower aliphatic acyloxy group; and $R^5$ and $R^6$ are the same as or different from and each represents a linear or branched lower alkyl group or cyclobutyl group, cyclopentyl group or cyclohexyl group being formed together with the carbon atom to which they are bonded, and the ring may be substituted with a hydroxyl group, a lower aliphatic acyloxy group, a linear or branched lower alkyl group, a lower alkoxy group or a halogen atom;

$R^2$ is a formula —$NR^7R^8$, wherein both $R^7$ and $R^8$ are hydrogen atoms;

$R^3$ is a phenyl group which may be substituted with hydroxyl group, a halogen atom, a linear or branched lower alkyl group, a lower alkoxy group, an acyl group, amino group, a mono- or di-lower alkylamino group or a cyano group; and $R^4$ is a lower alkyl group which may be substituted with a hydroxyl group, a halogen atom, a cyano group, an amino group, a mono- or di-lower alkylamino group, a lower alkoxy group, a carbamoyl group, a mono- or di-substituted carbamoyl group, a carboxyl group or a lower alkyloxycarboxyl group.

10. The purine compound, or its pharmacologically acceptable salt thereof, as claimed in claim 1, wherein $R^1$ is a formula:

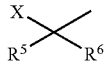

wherein X represents a hydroxyl group; and $R^5$ and $R^6$ are the same as or different from and each represents a lower alkyl group or a cyclobutyl group, a cyclopentyl group or a cyclohexyl group being formed with the carbon atom to which they are bonded;

$R^2$ is a formula —$NR^7R^8$, wherein both $R^7$ and $R^8$ are hydrogen atoms;

$R^3$ is an optionally halogen-substituted phenyl group; and $R^4$ is a lower alkyl group.

11. The purine compound, or its pharmacologically acceptable salt thereof, as claimed in claim 1 selected from the group consisting of:

1) 1-{2-[6-amino-8-(3-fluorophenyl)-9-methyl-9H-2-purinyl]-1-ethynyl}-1-cyclopentanol;
2) 1-{2-[6-amino-9-ethyl-8-(3-fluorophenyl)-9H-2-purinyl]-1-ethynyl}-1-cyclopentanol;
3) 1-{2-[6-amino-8-(3-fluorophenyl)-9-propyl-9H-2-purinyl]-1-ethynyl}-1-cyclopentanol;
4) 1-{2-[6-amino-8-(3-fluorophenyl)-9-methyl-9H-2-purinyl]-1-ethynyl}-1-cyclobutanol;
5) 1-{2-[6-amino-9-ethyl-8-(3-fluorophenyl)-9H-2-purinyl]-1-ethynyl}-1-cyclobutanol;
6) 1-{2-[6-amino-8-(3-fluorophenyl)-9-propyl-9H-2-purinyl]-1-ethynyl}-1-cyclobutanol;
7) 1-{2-[6-amino-9-dimethylaminophenyl-8-(3-fluorophenyl)-9H-2-purinyl]-1-ethynyl}-1-cyclohexanol;
8) 1-{2-[6-amino-8-(3,5-difluorophenyl)-9-methyl-9H-2-purinyl]-1-ethynyl}-1-cyclopentanol;
9) 1-[6-amino-8-(3-fluorophenyl)-9-propyl-9H-2-purinyl]-3-ethyl-1-pentyn-3-ol;
10) 4-[6-amino-9-ethyl-8-(3-fluorophenyl)-9H-2-purinyl]-2-methyl-3-butyn-2-ol;
11) 4-[6-amino-8-(3-fluorophenyl)-9-propyl-9H-2-purinyl]-2-methyl-3-butyn-2-ol;
12) 4-[6-amino-8-(3-fluorophenyl)-9-methyl-9H-2-purinyl]-2-methyl-3-butyn-2-ol; and
13) 1-{2-[6-amino-8-(3,5-difluorophenyl)-9-methyl-9H-2-purinyl]-1-ethynyl}-1-cyclobutanol.

12. A 2,6-dihalo-substituted purine compound represented by the formula (II):

(II)

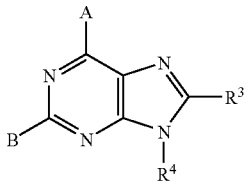

wherein A and B represent halogen atoms;

$R^3$ represents an optionally substituted $C_{3-8}$ cycloalkyl group, an optionally substituted aryl group or an optionally substituted heteroaryl group; and $R^4$ represents an optionally substituted linear or branched lower alkyl group, an optionally substituted aryl group or an optionally substituted heteroaryl group.

13. A method for the manufacturing of a 6-amino-2-ethynylene compound represented by the formula (V):

(V)

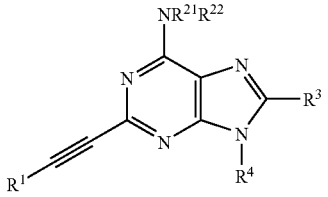

wherein $R^3$ represents an optionally substituted $C_{3-8}$ cycloalkyl group, an optionally substituted aryl group or an optionally substituted heteroaryl group; $R^4$ represents a linear or branched alkyl group, an optionally substituted aryl group or an optionally substituted heteroaryl group; $R^1$ represents:

1) formula:

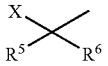

wherein X is a hydrogen atom, a hydroxyl group, an optionally substituted lower alkyl group, an optionally substituted lower alkoxy group, an optionally substituted aryl group, an optionally substituted heteroaryl group, an optionally substituted acyl group, an optionally substituted acyloxy group or an optionally substituted amino group; and $R^5$ and $R^6$ are the same as or different from and each represents a hydrogen atom, an optionally substituted lower alkyl group, an optionally substituted cycloalkyl group, an optionally substituted aryl group, an optionally substituted heteroaryl group, an optionally protected carboxyl group or an optionally substituted four- to six-membered ring having at least one hetero atom; optionally, $R^5$ and $R^6$ is either an oxygen atom or a sulfur atom together or are a ring which may have hetero atom being formed together with a carbon atom to which they are bonded; wherein the ring may be substituted; or 2) a five- or six-membered aromatic ring which may have substituent group and hetero, to give a 2-ethynylene-6-halopurine compound represented by the formula (IV):

(IV)

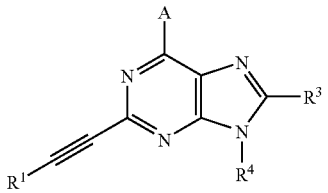

wherein A is a halogen atom, and $R^1$, $R^3$ and $R^4$ have the same meanings as defined above; and $R^{21}$ and $R^{22}$ are the same as or different from each other and each represents a hydrogen atom or an optionally substituted lower alkyl group or a saturated 3- or 8-membered ring being formed together with the nitrogen atom to which they are bonded and the ring containing said nitrogen atom optionally has another heteroatom of nitrogen or oxygen or is substituted; comprising the steps of:

a) reacting a 2,6-dihalo-substituted purine compound represented by the formula (II):

(II)

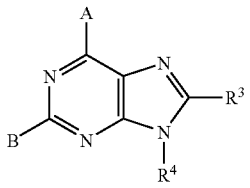

wherein A and B represent halogen atoms, and $R^3$ and $R^4$ are defined as above, with an ethynylene compound represented by the formula (III):

$R^1C{=}CH$ (III)

wherein in the formula (III) $R^1$ is defined as above in formula (V); and b) reacting the resulting compound with $HNR^{21}R^{22}$ to form said 6-amino-2-ethynylene compound represented by the formula (V).

14. A method for the manufacture of a 6-amino-2-ethynylene compound represented by the formula (V):

(V)

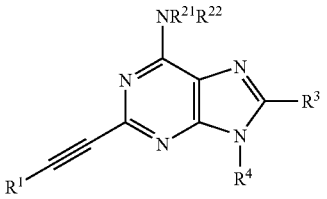

wherein $R^3$ represents an optionally substituted $C_{3-8}$ cycloalkyl group, an optionally substituted aryl group or an optionally substituted heteroaryl group; $R^4$ represents a linear or branched alkyl group, an optionally substituted aryl group or an optionally substituted heteroaryl group; $R^1$ represents:

1) formula:

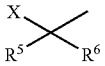

wherein X is a hydrogen atom, a hydroxyl group, an optionally substituted lower alkyl group, an optionally substituted lower alkoxy group, an optionally substituted aryl group, an optionally substituted heteroaryl group, an optionally substituted acyl group, an optionally substituted acyloxy group or an optionally substituted amino group; and $R^5$ and $R^6$ are the same as or different from and each represents a hydrogen atom, an optionally substituted lower alkyl group, an optionally substituted cycloalkyl group, an optionally substituted aryl group, an optionally substituted heteroaryl group, an optionally protected carboxyl group or an optionally substituted four- to six-membered ring having at least one hetero atom; optionally, $R^5$ and $R^6$ is either an oxygen atom or a sulfur atom together or are a ring which may have hetero atom being formed together with a carbon atom to which they are bonded; wherein the ring may be substituted; or 2) a five- or six-membered aromatic ring which may have substituent group and hetero, to give a 2-ethynylene-6-halopurine compound represented by the formula (IV):

(IV)

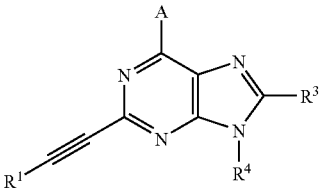

wherein A is a halogen atom, and $R^1$, $R^3$ and $R^4$ have the same meanings as defined above; and $R^{21}$ and $R^{22}$ are the same as or different from each other and each represents a hydrogen atom or an optionally substituted lower alkyl group or a saturated 3- or 8-membered ring being formed together with the nitrogen atom to which they are bonded and the ring containing said nitrogen atom optionally has another heteroatom or is substituted, comprising the steps of:

a) reacting a 2,6-dihalo-substituted purine compound represented by the formula (II):

(II)

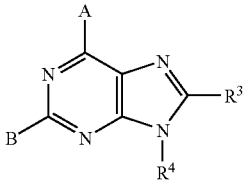

wherein A and B represent halogen atoms, and $R^3$ and $R^4$ are defined as above, with ammonia or a primary or secondary amine to give a 6-amino-2-halopurine compound represented by the formula (VI):

(VI)

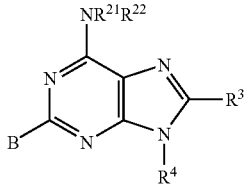

wherein B, $R^3$, $R^4$, $R^{21}$ and $R^{22}$ have the same meanings as defined above; and b) reacting the resulting compound with an ethynylene compound represented by the formula (III):

$$R^1—C\equiv H \quad \text{(III)}$$

wherein $R^1$ has the same meaning as defined above.

15. A preventive or therapeutic composition comprising:

the purine compound as claimed in claim 1, or its pharmacologically acceptable salt thereof, as an active ingredient, and a pharmaceutically acceptable carrier.

16. A method of treating a disease or condition selected from the group consisting of diabetes mellitus, diabetic complications, [hypoglycemia,] *hyperglycemia,* impaired glucose tolerance and obesity, said method comprising:

administering an effective amount of the purine compound of claim 1 to a patient in need thereof.

17. The method according to claim 16, wherein said disease or condition is impaired glucose tolerance.

18. The method according to claim 16, wherein said disease or condition is obesity.

19. The method according to claim 16, wherein said disease or condition is [hypoglycemia.] *hyperglycemia.*

20. The method according to claim 16, wherein said disease or condition is diabetes mellitus.

21. The method according to claim 16, wherein said disease or condition is diabetic complications.

22. A method of potentiating insulin sensitivity, said method comprising administering an effective amount of the purine compound of claim 1 to a patient in need thereof.

* * * * *